(12) United States Patent
Iafrate et al.

(10) Patent No.: US 10,450,597 B2
(45) Date of Patent: Oct. 22, 2019

(54) METHODS OF PREPARING NUCLEIC ACIDS FOR SEQUENCING

(71) Applicants: The General Hospital Corporation, Boston, MA (US); ArcherDX, Inc., Boulder, CO (US)

(72) Inventors: Anthony John Iafrate, Newton, MA (US); Long Phi Le, Boston, MA (US); Zongli Zheng, Boston, MA (US); Jason Myers, Golden, CO (US); Joshua Stahl, Boulder, CO (US)

(73) Assignees: THE GENERAL HOSPITAL CORPORATION, Boston, MA (US); ARCHERDX, INC., Boulder, CA (US)

( * ) Notice: Subject to any disclaimer, the term of this patent is extended or adjusted under 35 U.S.C. 154(b) by 274 days.

(21) Appl. No.: 14/605,363

(22) Filed: Jan. 26, 2015

(65) Prior Publication Data

US 2015/0211050 A1    Jul. 30, 2015

Related U.S. Application Data

(60) Provisional application No. 61/931,959, filed on Jan. 27, 2014.

(51) Int. Cl.
| | | |
|---|---|---|
| C12Q 1/68 | (2018.01) | |
| C12Q 1/6806 | (2018.01) | |
| C12Q 1/6809 | (2018.01) | |

(52) U.S. Cl.
CPC ......... *C12Q 1/6806* (2013.01); *C12Q 1/6809* (2013.01)

(58) Field of Classification Search
None
See application file for complete search history.

(56) References Cited

U.S. PATENT DOCUMENTS

| | | | |
|---|---|---|---|
| 4,868,104 A | 9/1989 | Kurn et al. | |
| 5,827,658 A | 10/1998 | Liang | |
| 6,087,101 A | 6/2000 | Gruelich et al. | |
| 6,172,214 B1 | 1/2001 | Brenner | |
| 6,576,448 B2 | 6/2003 | Weissman et al. | |
| 6,632,611 B2 | 10/2003 | Su et al. | |
| 6,833,246 B2 | 12/2004 | Balasubramanian | |
| 7,214,490 B2 | 5/2007 | Su et al. | |
| 7,244,559 B2 | 7/2007 | Rothberg et al. | |
| 7,273,730 B2 | 9/2007 | Du Breuil | |
| 7,824,856 B2 | 11/2010 | Monforte | |
| 9,487,828 B2 * | 11/2016 | Iafrate | C12C 1/6874 |
| 10,017,810 B2 | 7/2018 | Iafrate et al. | |
| 2002/0086317 A1 | 7/2002 | Nagayama et al. | |
| 2003/0104432 A1 | 6/2003 | Xu et al. | |
| 2003/0143553 A1 | 7/2003 | Sommer | |
| 2007/0172824 A1 * | 7/2007 | Chun | C12Q 1/686 435/6.11 |
| 2009/0203085 A1 * | 8/2009 | Kurn | C12C 1/686 435/91.2 |
| 2010/0286143 A1 | 11/2010 | Dias-Santagata et al. | |
| 2012/0122701 A1 | 5/2012 | Ryan et al. | |
| 2013/0005585 A1 * | 1/2013 | Anderson | C12N 15/10 506/2 |
| 2013/0231253 A1 | 9/2013 | Amorese et al. | |
| 2013/0303461 A1 | 11/2013 | Iafrate et al. | |
| 2015/0011396 A1 | 1/2015 | Schroeder et al. | |
| 2015/0140553 A1 | 5/2015 | Cushing et al. | |
| 2015/0252361 A1 | 9/2015 | Hayden et al. | |
| 2018/0127806 A1 | 5/2018 | Stahl et al. | |
| 2018/0127807 A1 | 5/2018 | Stahl et al. | |
| 2018/0155767 A1 | 6/2018 | Myers et al. | |

FOREIGN PATENT DOCUMENTS

| | | |
|---|---|---|
| AU | 2005203617 A1 | 9/2005 |
| WO | 97/23646 A1 | 7/1997 |
| WO | 97/23647 A1 | 7/1997 |
| WO | 98/28443 A1 | 7/1998 |
| WO | 99/42618 A1 | 8/1999 |
| WO | 00/43543 A1 | 7/2000 |
| WO | 00/70095 A2 | 11/2000 |
| WO | 01/12859 A2 | 2/2001 |
| WO | 01/20035 A2 | 3/2001 |
| WO | 2001/083696 A2 | 11/2001 |
| WO | 02/00938 A2 | 1/2002 |
| WO | 02/29117 A2 | 4/2002 |
| WO | 02/48402 A2 | 6/2002 |
| WO | 02/072772 A2 | 9/2002 |
| WO | 03/078645 A2 | 9/2003 |
| WO | 03/083435 A2 | 10/2003 |
| WO | 2004/011665 A2 | 2/2004 |
| WO | 2004/092418 A2 | 10/2004 |
| WO | 2005/065321 A2 | 7/2005 |
| WO | 2007/030759 A2 | 3/2007 |

(Continued)

OTHER PUBLICATIONS

Callaway, AS. et al. A sobemovirus coat protein gene complements long-distance movement of a coat protein-null dianthovirus. Virology, vol. 330, p. 186-195, 2004.*

Ali et al. "Sequence Analysis of TnphoA Insertion Sites in Vibrio cholera Mutants Defective in Rugose Polysaccharide Production", Infection and Immunity 68(12):6857-6864 (2000).

Baetens et al. "Applying Massive Parallel Sequencing to Molecular Diagnosis of Marfan and Loeys-Dietz Syndromes", Human Mutation 32:1053-1062 (2011).

Bohmer, "Novel application for isothermal nucleic acid sequence-based amplification (NASBA)", Journal of Virological Methods 158(1-2):199-201 (2009).

Chang et al., "Identification of a biomarker panel using a multiplex proximity ligation assay improves accuracy of pancreatic cancer diagnosis", Journal of Translational Medicine 7:105 (2009).

(Continued)

*Primary Examiner* — Suryaprabha Chunduru
(74) *Attorney, Agent, or Firm* — Nixon Peabody LLP; David S. Resnick; Nicole D. Kling

(57) ABSTRACT

Aspects of the technology disclosed herein relate to methods for preparing and analyzing nucleic acids. In some embodiments, methods for preparing nucleic acids for sequence analysis (e.g., using next-generation sequencing) are provided herein.

29 Claims, 5 Drawing Sheets

Specification includes a Sequence Listing.

(56) References Cited

FOREIGN PATENT DOCUMENTS

| WO | 2007/057652 A1 | 5/2007 |
|---|---|---|
| WO | 2007/136717 A1 | 11/2007 |
| WO | 2008/005459 A2 | 1/2008 |
| WO | 2008/093098 A2 | 8/2008 |
| WO | WO2001/083696 A2 * | 11/2008 |
| WO | 2009/102878 A2 | 8/2009 |
| WO | 2009/102896 A2 | 8/2009 |
| WO | 2009/117698 A2 | 9/2009 |
| WO | 2009/133466 A2 | 11/2009 |
| WO | 2009/148617 A2 | 12/2009 |
| WO | 2010/077288 A2 | 7/2010 |
| WO | 2010/083046 A2 | 7/2010 |
| WO | 2011/019964 A1 | 2/2011 |
| WO | 2011/032053 A1 | 3/2011 |
| WO | 2011/053987 A1 | 5/2011 |
| WO | 2011/156529 A2 | 12/2011 |
| WO | 2012/003374 A2 | 1/2012 |
| WO | 2012/040387 A1 | 3/2012 |
| WO | 2012/044956 A1 | 4/2012 |
| WO | 2012/064739 A2 | 5/2012 |
| WO | 2012/103154 A1 | 8/2012 |
| WO | 2013/059746 A1 | 4/2013 |
| WO | 2013/074833 A1 | 5/2013 |
| WO | 2013/112923 A1 | 8/2013 |
| WO | 2013/169339 A1 | 11/2013 |
| WO | 2013/191775 A2 | 12/2013 |
| WO | 2014/144092 A1 | 9/2014 |
| WO | 2014/150931 A1 | 9/2014 |
| WO | 2015/073711 A1 | 5/2015 |

OTHER PUBLICATIONS

Chen et al., "Allele-specific copy number profiling by next-generation DNA sequencing", Nucleic Acids Research 43(4):e23 (2015).

Chenchik, et al., "Full-Length cDNA Cloning and Determination of mRNA 5' and 3' Ends by Amplification of Adaptor-Ligated cDNA", BioTechniques 21(3):526-534 (1996).

Compton, "Nucleic acid sequence-based amplification", Nature 350(6313): 91-92 (1991).

Cushing et al., "RVD: a command-line program for ultrasensitive rare single nucleotide variant detection using targeted next-generation DNA resequencing", BMC Research Notes 6:206 (2013).

Dafforn et al., "Linear mRNA amplification from as little as 5 ng total RNA for global gene expression analysis", BioRechniques 37(5):854-857 (2004).

Dahl et al., "Multigene amplification and massively parallel sequencing for cancer mutation discovery", PNAS 104(22):9387-9392 (2007).

Zhang et al., "Detecting simultaneous changepoints in multiple sequences", Biometrika 97(3):631-645 (2010).

Zhang et al., "Titration-free 454 sequencing using Y adapters", Nature Protocols 6(9):1367-1376 (2011).

Lamant et al., "A New Fusion Gene TPM3-ALK in Anaplastic Large Cell Lymphoma Created by a (1;2)(q25;p23) Translocation", Blood 93(9):3088-3095 (1999).

Yuanxin et al., "T-linker-specific ligation PCR (T-linker PCR): an advanced PCR technique for chromosome walking or for isolation of tagged DNA ends", Nucleic Acids Research 31(12):e68 (2003).

Flaherty et al., "Ultrasensitive detection of rare mutations using next-generation targeted resequencing", Nucleic Acids Research 40(1):e2 (2012).

Fredriksson et al., "Multiplex amplification of all coding sequences within 10 cancer genes by Gene-Collector", Nucleic Acids Research 35(7):e47 (2007).

Fredriksson et al., "Multiplexed protein detection by proximity ligation for cancer biomarker validation", Nature Methods 4(4):327-329 (2007).

Grace et al., "Degradable dUMP Outer Primers in Merged Tandem (M/T)-Nested PCR: Low- and Single-Copy DNA Target Amplification", Analytical Biochemistry 263(1):85-92 (1998).

Green et al., "Hierarchy in somatic mutations arising during genomic evolution and progression of follicular lymphoma", Blood 121(9):1604-1611 (2013).

Grimes et al., "MendeLIMS: a web-based laboratory information management system for clinical genome sequencing", BMC Bioinformatics 15:290 (2014).

Guled et al., "Array comparative genomic hybridization analysis of olfactory neuroblastoma", Modern Pathology 21(6):770-778 (2008).

Head et al., "Method for improved Illumina sequencing library preparation using NuGEN Ovation RNA-Seq System", Biotechniques 50(3):177-181 (2011).

Hoeijmakers et al., "Linear amplification for deep sequencing", Nature Protocols 6(7):1026-1036 (2011).

Hoon et al., "Aptamer selection by high-throughput sequencing and informatic analysis", Biotechniques 51(6):413-416 (2011).

Hopmans et al., "A programmable method for massively parallel targeted sequencing", Nucleic Acids Research 42(10):e88 (2014).

Ji et al., "Data quality in genomics and microarrays", Nat Biotechnol. 24(9):1112-1113 (2006).

Ji et al., "Identification of a novel deletion mutant strain in *Saccharomyces cerevisiae* that results in a microsatellite instability phenotype", Biodiscovery 1:4 (2012).

Ji, "Improving bioinformatic pipelines for exome variant calling", Genome Medicine 4(1):7 (2012).

Ji et al., "Molecular Inversion Probe Analysis of Gene Copy Alterations Reveals Distinct Categories of Colorectal Carcinoma", Cancer Res. 66(16):7910-7919 (2006).

Ji et al., "Molecular inversion probe assay for allelic quantitation", Methods Mol Biol. 556:67-87 (2009).

Kim et al., "Genetic-based biomarkers and next-generation sequencing: the future of personalized care in colorectal cancer", Per Med. 8(3):331-345 (2011).

Kinde et al., "Detection and quantification of rare mutations with massively parallel sequencing", PNAS 108 (23):9530-95355 (2011).

Kurn et al., "Novel Isothermal, Linear Nucleic Acid Amplification Systems for Highly Multiplexed Applications", Clinical Chemistry 51(10):1973-1981 (2005).

Lam et al., "Performance comparison of whole-genome sequencing platforms", Nat Biotechnol. 30(1):78-82 (2011).

Lee et al., "Systematic genomic identification of colorectal cancer genes delineating advanced from early clinical stage and metastasis", BMC Medical Genomics 6:54 (2013).

Lin et al., "Reproducibility Probability Score—incorporating measurement variability across laboratories for gene selection", Nature Biotechnology 24(12):1476-1477 (2006).

Lishanski et al., "Branch migration inhibition in PCR-amplified DNA: homogeneous mutation detection", Nucleic Acids Research 28(9):e42 (2000).

MAQC Consortium, "The MicroArray Quality Control (MAQC) project shows inter- and intraplatform reproducibility of gene expression measurements", Nat Biotechnol. 24(9):1151-1161 (2006).

Miotke et al., "Correction to High Sensitivity Detection and Quantitation of DNA Copy Number and Single Nucleotide Variants with Single Color Droplet Digital PCR", Anal. Chem. 87:3114 (2015).

Miotke et al., "High Sensitivity Detection and Quantitation of DNA Copy Number and Single Nucleotide Variants with Single Color Droplet Digital PCR", Anal. Chem. 86(5):2618-2624 (2014).

Mugasa et al., "Nucleic Acid Sequence-Based Amplification with Oligochromatography for Detection of Trypanosoma brucei in Clinical Samples", Journal of Clinical Microbiology 47(3):630-635 (2009).

Muralidharan et al., "A cross-sample statistical model for SNP detection in short-read sequencing data", Nucleic Acids Research 40(1):e5 (2012).

Myllykangas et al., "Classification of human cancers based on DNA copy number amplification modeling", BMC Medical Genomics 1:15 (2008).

Myllykangas et al., "DNA copy number amplification profiling of human neoplasms", Oncogene 25(55):7324-7332 (2006).

Myllykangas et al., "Efficient targeted resequencing of human germline and cancer genomes by oligonucleotide-selective sequencing", Nat Biotechnol. 29(11):1024-1027 (2011).

(56) References Cited

OTHER PUBLICATIONS

Myllykangas et al., "Integrated gene copy number and expression microarray analysis of gastric cancer highlights potential target genes", Int. J. Cancer 123(4):817-825 (2008).

Myllykangas et al., "Manifestation, mechanisms and mysteries of gene amplifications", Cancer Letters 232(1):79-89 (2006).

Myllykangas et al., "Novel high-throughput sequencing strategies in genetic diagnostics", Duodecim. 129(2):141-148 (2013). English Abstract [Review Finnish].

Myllykangas et al., "Specificity, selection and significance of gene amplifications in cancer", Seminars in Cancer Biology 17(1):42-55 (2007).

Myllykangas et al., "Targeted deep resequencing of the human cancer genome using next-generation technologies", Biotechnol Genet Eng Rev. 27:135-158 (2010).

Myllykangas et al., "Targeted sequencing library preparation by genomic DNA circularization", BMC Biotechnology 11:122 (2011).

Nadauld et al., "Quantitative and Sensitive Detection of Cancer Genome Amplifications from Formalin Fixed Paraffin Embedded Tumors with Droplet Digital PCR", Transl Med (Sunnyvale) 2(2) (2012).

Natsoulis et al., "A Flexible Approach for Highly Multiplexed Candidate Gene Targeted Resequencing", PLoS One. 6(6):e21088 (2011).

Natsoulis et al., "Identification of Insertion Deletion Mutations from Deep Targeted Resequencing", J Data Mining Genomics Proteomics 4(3) (2013).

Newburger et al., "The Human OligoGenome Resource: a database of oligonucleotide capture probes for resequencing target regions across the human genome", Nucleic Acids Research 40(Database issue):D1137-D1143 (2012).

Scheinin et al., "CanGEM: mining gene copy number changes in cancer", Nucleic Acids Research 36(Database issue):D830-835 (2008).

Schiffman et al., "Molecular inversion probes reveal patterns of 9p21 deletion and copy number aberrations in childhood leukemia", Cancer Genet Cytogenet. 193(1):9-18 (2009).

Schiffman et al., "Oncogenic BRAF Mutation with CDKN2A Inactivation is Characteristic of a Subset of Pediatric Malignant Astrocytomas", Cancer Res. 70(2):512-519 (2010).

Shendure et al., "Next-generation DNA sequencing", Nature Biotechnology 26(10):1135-1145 (2008).

Singh et al., "Microarray-based comparison of three amplification methods for nanogram amounts of total RNA", Am J Physiol Cell Physiol. 288(5):C1179-C1189 (2005).

Sinkkonen et al., "Serial Analysis of Gene Expression in the Chicken Otocyst", JARO 12(6):697-710 (2011).

Tong et al., "Genome-scale identification of conditionally essential genes in E. coli by DNA microarrays", Biochemical and Biophysical Research Communications 322(1):347-354 (2004).

Turner et al., "Gene Expression Profiling of RNA Extracted from FFPE Tissues: NuGEN Technologies' Whole-Transcriptome Amplification System", Methods Mol Biol. 724:269-280 (2011).

Xiao et al., "Sequential Amplification of Flanking Sequences by Y-shaped Adaptor Dependent Extension Using Multiple Templates", 33(1):85-90 (2007).

Gould et al., "Analysis of sequence variation among smeDEF multi drug efflux pump genes and flanking DNA from defined 16S rRNA subgroups of clinical Stenotrophomonas maltophilia isolates." Journal of Antimicrobial Chemotherapy 54(2):348-353 (2004).

Liu et al., "High-efficiency thermal asymmetric interlaced PCR for amplification of unknown flanking sequences." Biotechniques Rapid Dispatches 43(5):649-656 (2007).

Wang et al. "Fusion primer and nested integrated PCR (FPNI-PCR): a new high-efficiency strategy for rapid chromosome walking or flanking sequence cloning." BMC Biotechnology 11(1):109 (2011).

Callaway et al., "A Sobemovirus coat protein gene complements long-distance movement of a coat protein-null Dianthovirus." Virology 330(1):186-195 (2004).

Frohman et al., "Rapid production of full-length cDNAs from rare transcripts: amplification using a single gene-specific oligonucleotide primer." PNAS 85(23):8998-9002 (1988).

Kim et al., "FISH-negative cryptic PML-RARA rearrangement detected by long-distance polymerase chain reaction and sequencing analyses: a case study and review of the literature." Cancer Genetics and Cytogenetics 203(2):278-283 (2010).

* cited by examiner

METHODS OF PREPARING NUCLEIC ACIDS FOR SEQUENCING

RELATED APPLICATIONS

This application claims the benefit under 35 U.S.C. § 119 of U.S. provisional application 61/931,959 filed Jan. 27, 2014, the entire contents of which is incorporated herein by reference.

SEQUENCE LISTING

The instant application contains a Sequence Listing which has been submitted electronically in ASCII format and is hereby incorporated by reference in its entirety. Said ASCII copy, created on Mar. 13, 2015, is named 030258-079365-US SL.txt and is 31,392 bytes in size.

TECHNICAL FIELD

The technology described herein relates to methods of preparing and analyzing nucleic acids.

BACKGROUND

Target enrichment prior to next-generation sequencing is more cost-effective than whole genome, whole exome, and whole transcriptome sequencing and therefore more practical for broad implementation; both for research discovery and clinical applications. For example, high coverage depth afforded by target enrichment approaches enables a wider dynamic range for allele counting (in gene expression and copy number assessment) and detection of low frequency mutations, a critical feature for evaluating somatic mutations in cancer. Examples of current enrichment protocols for next generation sequencing include hybridization-based capture assays (TruSeq Capture, Illumina; SureSelect Hybrid Capture, Agilent) and polymerase chain reaction (PCR)-based assays (HaloPlex, Agilent; AmpliSeq, Ion Torrent; TruSeq Amplicon, Illumina; emulsion/digital PCR, Raindance). Hybridization-based approaches capture not only the targeted sequences covered by the capture probes but also near off-target bases that consume sequencing capacity. In addition, these methods are relatively time-consuming, labor-intensive, and suffer from a relatively low level of specificity.

SUMMARY

Aspects of the technology disclosed herein relate to methods for preparing and analyzing nucleic acids. In some embodiments, methods for preparing nucleic acids for sequence analysis (e.g., using next-generating sequencing) are provided herein. In some embodiments, technology described herein is directed to methods of determining nucleotide sequences of nucleic acids. In some embodiments, the methods described herein relate to enriching target nucleic acids prior to sequencing.

Aspects of the technology disclosed herein relate to methods of determining the nucleotide sequence contiguous to a known target nucleotide sequence. In some embodiments, the methods involve (a) contacting a target nucleic acid molecule comprising the known target nucleotide sequence with an initial target-specific primer under hybridization conditions; (b) performing a template-dependent extension reaction that is primed by a hybridized initial target-specific primer and that uses the target nucleic acid molecule as a template; (c) contacting the product of step (b) with a population of tailed random primers under hybridization conditions; (d) performing a template-dependent extension reaction that is primed by a hybridized tailed random primer and that uses the portion of the target nucleic acid molecule downstream of the site of hybridization as a template; (e) amplifying a portion of the target nucleic acid molecule and the tailed random primer sequence with a first tail primer and a first target-specific primer; (f) amplifying a portion of the amplicon resulting from step (e) with a second tail primer and a second target-specific primer; and (g) sequencing the amplified portion from step (f) using a first and second sequencing primer. In some embodiments, the population of tailed random primers comprises single-stranded oligonucleotide molecules having a 5' nucleic acid sequence identical to a first sequencing primer and a 3' nucleic acid sequence comprising from about 6 to about 12 random nucleotides. In some embodiments, the first target-specific primer comprises a nucleic acid sequence that can specifically anneal to the known target nucleotide sequence of the target nucleic acid at the annealing temperature. In some embodiments, the second target-specific primer comprises a 3' portion comprising a nucleic acid sequence that can specifically anneal to a portion of the known target nucleotide sequence comprised by the amplicon resulting from step (e), and a 5' portion comprising a nucleic acid sequence that is identical to a second sequencing primer and the second target-specific primer is nested with respect to the first target-specific primer. In some embodiments, the first tail primer comprises a nucleic acid sequence identical to the tailed random primer. In some embodiments, the second tail primer comprises a nucleic acid sequence identical to a portion of the first sequencing primer and is nested with respect to the first tail primer.

In some embodiments, the methods involve (a) contacting a target nucleic acid molecule comprising the known target nucleotide sequence with a population of tailed random primers under hybridization conditions; (b) performing a template-dependent extension reaction that is primed by a hybridized tailed random primer and that uses the portion of the target nucleic acid molecule downstream of the site of hybridization as a template; (c) contacting the product of step (b) with an initial target-specific primer under hybridization conditions; (d) performing a template-dependent extension reaction that is primed by a hybridized initial target-specific primer and that uses the target nucleic acid molecule as a template; (e) amplifying a portion of the target nucleic acid molecule and the tailed random primer sequence with a first tail primer and a first target-specific primer; (f) amplifying a portion of the amplicon resulting from step (e) with a second tail primer and a second target-specific primer; and (g) sequencing the amplified portion from step (f) using a first and second sequencing primer. In some embodiments, the population of tailed random primers comprises single-stranded oligonucleotide molecules having a 5' nucleic acid sequence identical to a first sequencing primer and a 3' nucleic acid sequence comprising from about 6 to about 12 random nucleotides. In some embodiments, the first target-specific primer comprises a nucleic acid sequence that can specifically anneal to the known target nucleotide sequence of the target nucleic acid at the annealing temperature. In some embodiments, the second target-specific primer comprises a 3' portion comprising a nucleic acid sequence that can specifically anneal to a portion of the known target nucleotide sequence comprised by the amplicon resulting from step (c), and a 5' portion comprising a nucleic acid sequence that is identical to a second sequencing primer and the second target-specific primer is nested with respect to the first target-specific primer. In some embodiments, the first tail primer comprises a nucleic acid sequence identical to the tailed random primer. In some embodiments, the second tail primer comprises a nucleic acid sequence identical to a portion of the first sequencing primer and is nested with respect to the first tail primer.

In some embodiments, the methods further involve a step of contacting the sample and/or products with RNase after extension of the initial target-specific primer. In some embodiments, the tailed random primer can form a hair-pin loop structure. In some embodiments, the initial target-specific primer and the first target-specific primer are identical. In some embodiments, the tailed random primer further comprises a barcode portion comprising 6-12 random nucleotides between the 5' nucleic acid sequence identical to a first sequencing primer and the 3' nucleic acid sequence comprising 6-12 random nucleotides.

In some embodiments, the methods involve (a) contacting a target nucleic acid molecule comprising the known target nucleotide sequence with a population of tailed random primers under hybridization conditions; (b) performing a template-dependent extension reaction that is primed by a hybridized tailed random primer and that uses the portion of the target nucleic acid molecule downstream of the site of hybridization as a template; (c) amplifying a portion of the target nucleic acid molecule and the tailed random primer sequence with a first tail primer and a first target-specific primer; (d) amplifying a portion of the amplicon resulting from step (c) with a second tail primer and a second target-specific primer; and (e) sequencing the amplified portion from step (d) using a first and second sequencing primer. In some embodiments, the population of tailed random primers comprises single-stranded oligonucleotide molecules having a 5' nucleic acid sequence identical to a first sequencing primer; a middle barcode portion comprising; and a 3' nucleic acid sequence comprising from about 6 to about 12 random nucleotides. In some embodiments, the first target-specific primer comprises a nucleic acid sequence that can specifically anneal to the known target nucleotide sequence of the target nucleic acid at the annealing temperature. In some embodiments, the second target-specific primer comprises a 3' portion comprising a nucleic acid sequence that can specifically anneal to a portion of the known target nucleotide sequence comprised by the amplicon resulting from step (c), and a 5' portion comprising a nucleic acid sequence that is identical to a second sequencing primer and the second target-specific primer is nested with respect to the first target-specific primer. In some embodiments, the first tail primer comprises a nucleic acid sequence identical to the tailed random primer. In some embodiments, the second tail primer comprises a nucleic acid sequence identical to a portion of the first sequencing primer and is nested with respect to the first tail primer. In some embodiments, the each tailed random primer further comprises a spacer nucleic acid sequence between the 5' nucleic acid sequence identical to a first sequencing primer and the 3' nucleic acid sequence comprising about 6 to about 12 random nucleotides. In certain embodiments, the unhybridized primers are removed from the reaction after an extension step. In some embodiments, the second tail primer is nested with respect to the first tail primer by at least 3 nucleotides. In certain embodiments, the first target-specific primer further comprises a 5' tag sequence portion comprising a nucleic acid sequence of high GC content which is not substantially complementary to or substantially identical to any other portion of any of the primers. In some embodiments, the second tail primer is identical to the full-length first sequencing primer. In certain embodiments, the portions of the target-specific primers that specifically anneal to the known target will anneal specifically at a temperature of about 65° C. in a PCR buffer. In some embodiments, the sample comprises genomic DNA. In some embodiments, the sample comprises RNA and the method further comprises a first step of subjecting the sample to a reverse transcriptase regimen. In certain embodiments, the nucleic acids present in the sample have not been subjected to shearing or digestion. In some embodiments, the sample comprises single-stranded gDNA or cDNA. In certain embodiments, the reverse transcriptase regimen comprises the use of random hexamers. In some embodiments, a gene rearrangement comprises the known target sequence. In certain embodiments, the gene rearrangement is present in a nucleic acid selected from the group consisting of: genomic DNA; RNA; and cDNA. In some embodiments, the gene rearrangement comprises an oncogene. In certain embodiments, the gene rearrangement comprises a fusion oncogene. In some embodiments, the nucleic acid product is sequenced by a next-generation sequencing method. In certain embodiments, the next-generation sequencing method comprises a method selected from the group consisting of: Ion Torrent, Illumina, SOLiD, 454; Massively Parallel Signature Sequencing solid-phase, reversible dye-terminator sequencing; and DNA nanoball sequencing. In certain embodiments, the first and second sequencing primers are compatible with the selected next-generation sequencing method. In some embodiments, the method comprises contacting the sample, or separate portions of the sample, with a plurality of sets of first and second target-specific primers. In certain embodiments, the method comprises contacting a single reaction mixture comprising the sample with a plurality of sets of first and second target-specific primers. In some embodiments, the plurality of sets of first and second target-specific primers specifically anneal to known target nucleotide sequences comprised by separate genes. In certain embodiments, at least two sets of first and second target-specific primers specifically anneal to different portions of a known target nucleotide sequence. In some embodiments, at least two sets of first and second target-specific primers specifically anneal to different portions of a single gene comprising a known target nucleotide sequence. In certain embodiments, at least two sets of first and second target-specific primers specifically anneal to different exons of a gene comprising a known nucleotide target sequence. In some embodiments, the plurality of first target-specific primers comprise identical 5' tag sequence portions. In certain embodiments, each tailed random primer in a population of tailed random primers further comprises an identical sample barcoding portion. In some embodiments, multiple samples are each contacted with a separate population of tailed random primers with a sample barcoding portion; wherein each population of tailed random primers has a distinct sample barcoding portion; and wherein the samples are pooled after step (b). In certain embodiments, each amplification step comprises a set of cycles of a PCR amplification regimen from 5 cycles to 20 cycles in length. In some embodiments, the target-specific primers and the tail primers are designed such that they will specifically anneal to their complementary sequences at an annealing temperature of from about 61 to 72° C. In some embodiments, the target-specific primers and the tail primers are designed such that they will specifically anneal to their complementary sequences at an annealing temperature of about 65° C. In certain embodiments, the target nucleic acid molecule is from a sample, optionally which is a biological sample obtained from a subject. In some embodiments, the sample is obtained from a subject in need of treatment for a disease associated with a genetic alteration. In certain embodiments, the disease is cancer. In some embodiments, the sample comprises a population of tumor cells. In certain embodiments, the sample is a tumor biopsy. In some embodiments, the cancer is lung cancer. In certain embodiments, a disease-associated gene comprises the known target sequence. In some embodiments, a gene rearrangement product in the sample comprises the known target sequence. In certain embodiments, the gene rearrangement product is an oncogene.

Aspects of the technology disclosed herein relate to methods of preparing nucleic acids for analysis. In some embodiments, the methods involve method (a) contacting a nucleic acid template comprising a first strand of a target nucleic acid with a complementary target-specific primer that comprises a target-specific hybridization sequence, under conditions to promote template-specific hybridization and extension of the target-specific primer; and (b) contacting a nucleic acid template comprising a second strand that is complementary to the first strand of the target nucleic acid with a plurality of different primers that share a common sequence that is 5' to different hybridization sequences, under conditions to promote template-specific hybridization and extension of at least one of the plurality of different primers, in which an extension product is generated to contain both a sequence that is characteristic of the target-specific primer and a sequence that is characteristic of the at least one of the plurality of different primers. In some embodiments, the target nucleic acid is a ribonucleic acid. In certain embodiments, the target nucleic acid is a deoxyribonucleic acid. In some embodiments, steps (a) and (b) are performed sequentially. In certain embodiments, the nucleic acid template in step (a) comprises an extension product resulting from the hybridization and extension of the at least one of the plurality of different primers in step (b). In some embodiments, the nucleic acid template in step (b) comprises an extension product resulting from the hybridization and extension of the target-specific primer in step (a). In certain embodiments, the target nucleic acid is a messenger RNA encoded from a chromosomal segment that comprises a genetic rearrangement. In some embodiments, the target nucleic acid is a chromosomal segment that comprises a portion of a genetic rearrangement. In certain embodiments, the genetic rearrangement is an inversion, deletion, or translocation. In some embodiments, the methods further involve amplifying the extension product. In certain embodiments, the methods further involve contacting the extension product or amplified extension product with an immobilized oligonucleotide under conditions in which hybridization occurs between the extension product and immobilized oligonucleotide. In certain embodiments, the target nucleic acid comprises a target portion having a known sequence and a flanking portion having an unknown sequence. In some embodiments, different hybridization sequences are complementary to the flanking portion. In certain embodiments, the target-specific hybridization sequence is complementary to the target portion. In some embodiments, the target-specific primer further comprises, 5' to the target-specific hybridization sequence, at least one of an index sequence, a barcode sequence and an adaptor sequence. In certain embodiments, the common sequence comprises at least one of an index sequence, barcode sequence and an adaptor sequence. In some embodiments, the adaptor sequence is a cleavable adaptor sequence for immobilizing oligonucleotides in a flow cell.

DETAILED DESCRIPTION

Figure 1A:
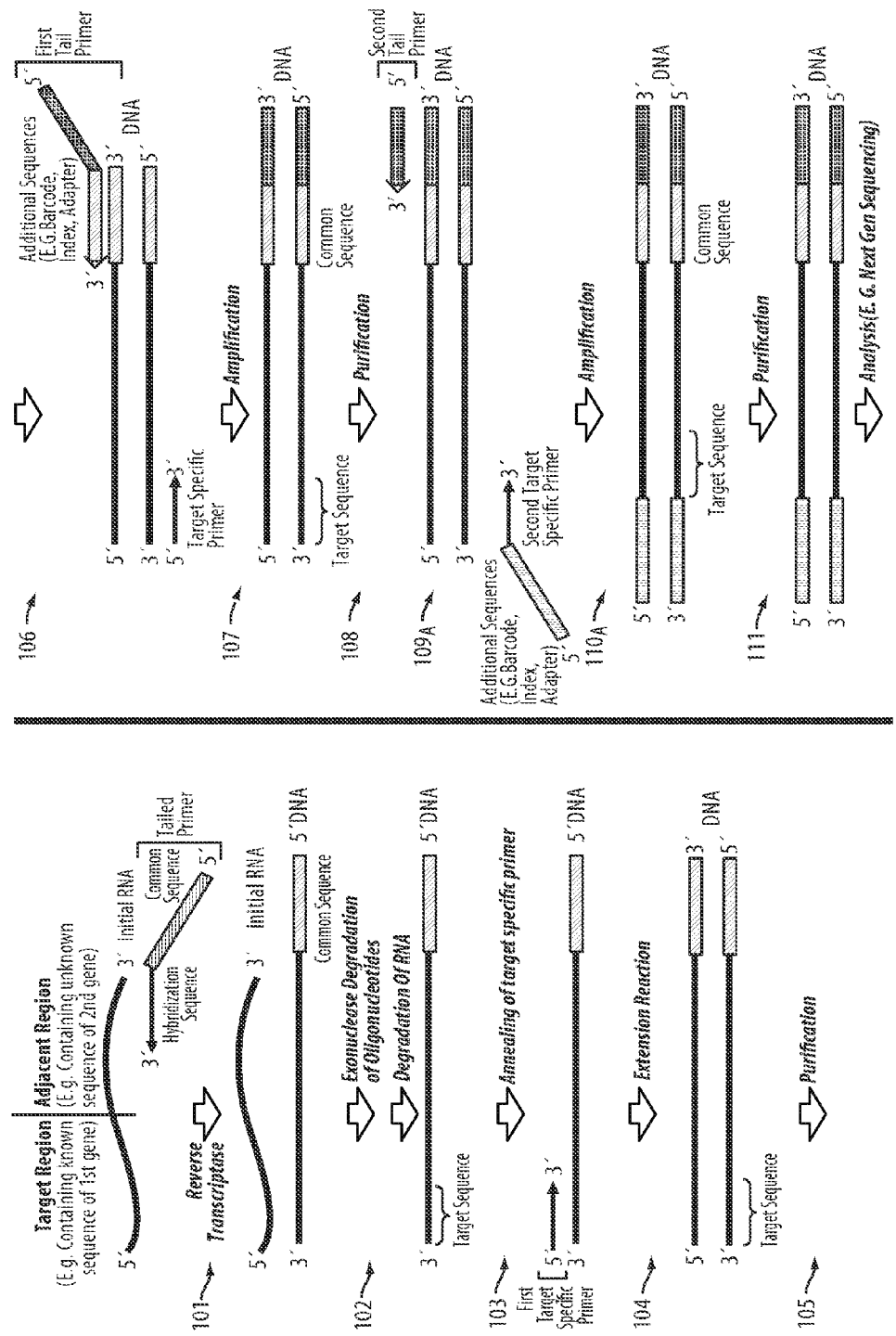
FIGS. 1A and 1B depict non-limiting embodiments of a work flow for amplifying and sequencing target nucleic acids that are flanked by a 3' unknown fusion partner, as described herein.

Aspects of the technology disclosed herein relate to methods for preparing and analyzing nucleic acids. In some embodiments, methods provided herein are useful for determining unknown nucleotide sequences contiguous to (adjacent to) a known target nucleotide sequence. Traditional sequencing methods generate sequence information randomly (e.g. "shotgun" sequencing) or between two known sequences which are used to design primers. In contrast, methods described herein, in some embodiments, allow for determining the nucleotide sequence (e.g. sequencing) upstream or downstream of a single region of known sequence with a high level of specificity and sensitivity. Accordingly, in some embodiments, methods provided herein are useful for determining the sequence of fusions (e.g., fusion mRNAs) that result from gene arrangements (e.g., rearrangements that give rise to cancer or other disorders). In some embodiments, methods provided herein for preparing nucleic acids for analysis (e.g., for sequencing) involve a first round of extension using a target-specific primer that targets a known sequence of a target nucleic acid (e.g., a known sequence of a $1^{st}$ gene) followed by a second round of extension that involves the use of a heterogenous population of tailed primers (e.g., tailed random primers) that include tailed primers that have hybridization sequences that are complementary with an unknown sequence adjacent to the known sequence in the target nucleic acid. In some embodiments, the tail region of tailed primers includes barcode or index sequences that facilitate multiplex amplification and enrichment of target nucleic acids.

In some aspects of the technology disclosed herein methods are provided of preparing nucleic acids for analysis that involve (a) contacting a nucleic acid template comprising a first strand of a target nucleic acid with a complementary target-specific primer that comprises a target-specific hybridization sequence, under conditions to promote template-specific hybridization and extension of the target-specific primer and (b) contacting a nucleic acid template comprising a second strand that is complementary to the first strand of the target nucleic acid with a plurality of different primers that share a common sequence that is 5' to different hybridization sequences, under conditions to promote template-specific hybridization and extension of at least one of the plurality of different primers, in which an extension product is generated to contain both a sequence that is characteristic of the target-specific primer and a sequence that is characteristic of the at least one of the plurality of different primers. In some embodiments, steps (a) and (b) above are performed sequentially. In some embodiments, the nucleic acid template in step (a) comprises an extension product resulting from the hybridization and extension of the at least one of the plurality of different primers in step (b). In some embodiments, the nucleic acid template in step (b) comprises an extension product resulting from the hybridization and extension of the target-specific primer in step (a).

In some embodiments, methods are provided for preparing nucleic acids that have a target region 5' to an adjacent region (e.g., an adjacent region of unknown sequence). In some embodiments, methods provided herein can be accomplished using one or more rounds of PCR.

Figure 1B:
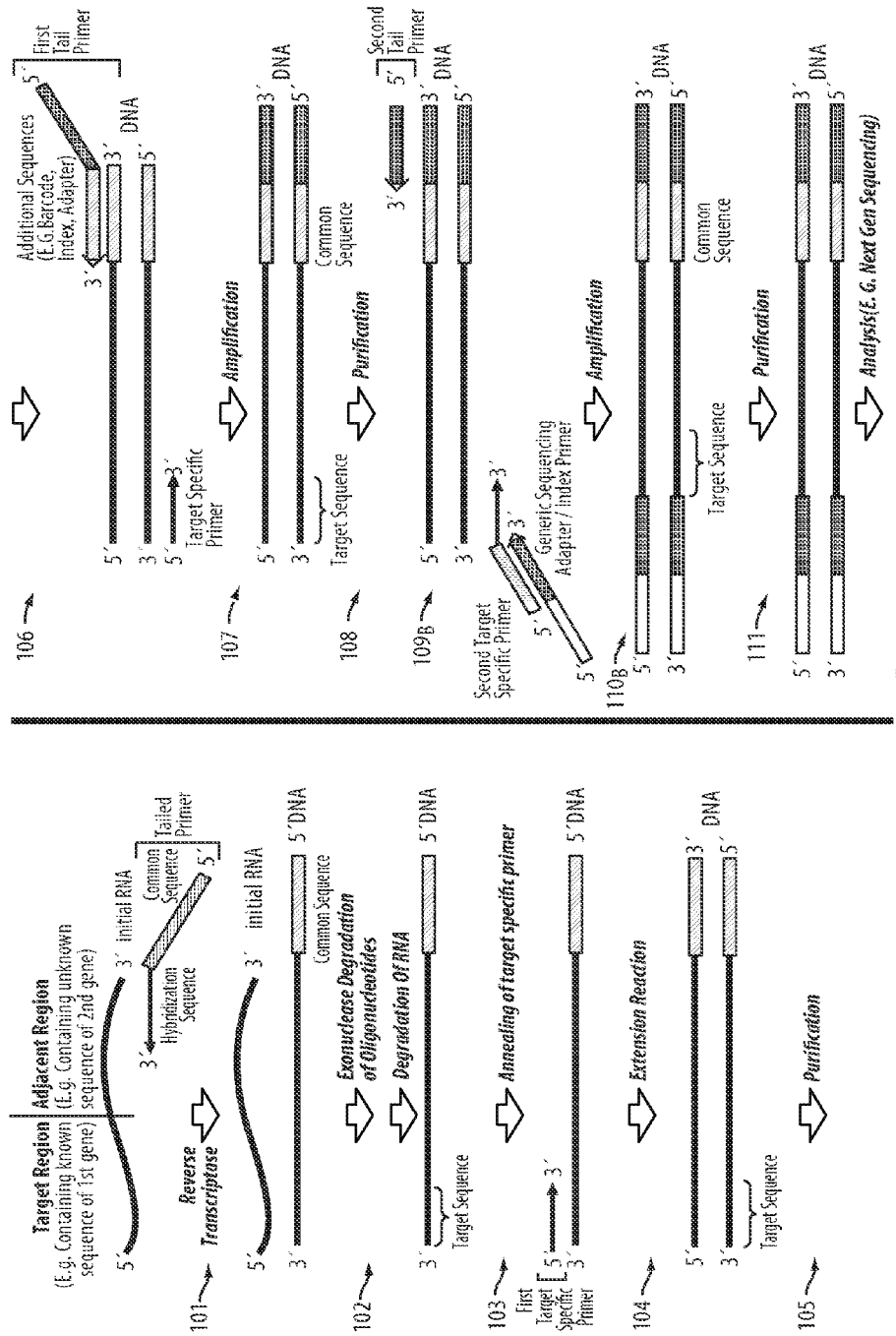

For example, FIGS. 1A-B present schematics of exemplary methods of amplifying target nucleic acids that have a known target region 5' to an adjacent region (e.g., for purposes of sequencing the adjacent region). At step 101, initial RNA is obtained or provided in a sample and is used as a template. RNA template is exposed to a plurality of tailed primers (e.g., tailed random primers) that comprise a common sequence that is 5' to different hybridization sequences and shared between all of the tailed primers of the population. In some embodiments, at least one primer hybridizes to an RNA molecule and primes a reverse transcriptase reaction to produce a complementary DNA strand. In step 102, unhybridized oligonucleotides are degraded (e.g., enzymatically, e.g., by an exonuclease). In step 102, RNA template is degraded from the complementary DNA strand.

In some embodiments, a tailed primer is provided that hybridizes to the poly-A tail of an RNA molecule. In some embodiments, the sequence of a primer is provided that hybridizes to the poly-A tail comprises a poly-dT (e.g., a 3' positioned stretch of 2 dTs, 3 dTs, 4 dTs, 5 dTs, 6 dTs, 7 dTs, 8 dTs, 9 dTs, 10 dTs, or more.). In some embodiments, a plurality of tailed primers are provided each of which comprises a common sequence. In some embodiments, a plurality of tailed primers is provided each of which further comprises a barcode or index sequence.

It should be appreciated that in methods disclosed herein an RNA template may be degraded by any appropriate method, including, for example, by enzymatic degradation (e.g., using RNaseH, Uracyl glycosylase, etc.), by hydrolysis (e.g., by exposing the RNA to relatively high pH conditions (e.g., pH 10, pH 11, pH 12), etc. In some embodiments, hydrolyzing RNA by exposure to relatively high pH is advantageous because it is relatively inexpensive (compared with certain other methods, e.g., certain enzymatic methods) and because it destroys both RNA and DNA:RNA hybrids. In some embodiments, RNA is degraded by hydrolysis caused by exposure to relatively high pH conditions at a relatively high temperature (e.g., temperature greater than 60° C. (e.g., 60° C. to 95° C.)). In some embodiments, the use of relatively high temperatures is advantageous because it heat inactivates enzymes used in prior preparative steps (e.g., RT enzymes). In some embodiments, an initial nucleic acid may be DNA that is obtained or provided in a sample and is used as a template. In such embodiments, steps 101 and 102 may be omitted.

In step 103, DNA molecules produced by reverse transcription are contacted by one or more initial target-specific primers which may or may not be the same as the first target-specific primer. In step 104, hybridization of the initial target-specific primer to a portion of the target nucleic acid (the "target sequence") primes an extension reaction using a DNA molecule as a template to produce a complementary DNA strand. Extension products are purified in step 105. However, in some embodiments, DNA produced in step 104 may be amplified directly, e.g., by PCR, without purification.

In step 106, DNA molecules are contacted by a first target-specific primer and a first tail primer. The first target-specific primer hybridizes to a portion of the target nucleic acid. In some embodiments, pools of different first target-specific primers can be used that hybridize to different portions of a target nucleic acid. In some embodiments, use of different target specific primers can be advantegous because it allows for generation of different extension products having overlapping but staggered sequences relative to a target nucleic acid. In some embodiments, different extension products can be sequenced to produce overlapping sequence reads. In some embodiments, overlapping sequence reads can be evaluated to assess accuracy of sequence information, fidelity of nucleic acid amplification, and/or to increase confidence in detecting mutations, such as detecting locations of chromosomal rearrangements (e.g., fusion breakpoints). In some embodiments, pools of different first target-specific primers can be used that hybridize to different portions of different target nucleic acids present in sample. In some embodiments, use of pools of different target-specific primers is advantageous because it facilitates processing (e.g., amplification) and analysis of different target nucleic acids in parallel. In some embodiments, up to 2, up to 3, up to 4, up to 5, up to 6, up to 7, up to 8, up to 9, up to 10, up to 15, up to 20, up to 100 or more pools of different first target-specific primers are used. In some embodiments, 2 to 5, 2 to 10, 5 to 10, 5 to 15, 10 to 15, 10 to 20, 10 to 100, 50 to 100, or more pools of different first target-specific primers are used.

In FIGS. 1A and 1B, a first tail primer hybridizes to at least a portion of a DNA molecule provided by the tail portion of the tailed primer of step 101. In some embodiments, the first tail primer hybridizes to the common sequence provided by the tail of the one or more primers of step 101. In some embodiments, a nested target specific primer (nested with respect to the target specific primer of step 103) is used in step 106. In some embodiments, a first tail primer may comprise an additional sequence 5' to the hybridization sequence that may include barcode, index, adapter sequences, or sequencing primer sites, for example. In step 107, hybridization of the first target-specific primer and the first tail nucleic acid molecule allows for amplification of a product in a polymerase chain reaction (PCR). In some embodiments, amplified products are purified in step 108.

In some embodiments, the ssDNA product of step 103 is amplified directly (e.g., by PCR) rather than performing the extension reaction of step 104 and purification of step 105. Similarly, in some embodiments of any of the methods disclosed herein, ssDNA products may be amplified directly (e.g., by PCR) rather than performing an extension reaction to produce dsDNA prior to purification and/or PCR. In some embodiments, first and second tail primers can be incorporated during a PCR. In some embodiments, primers (e.g., first tail primers, target specific primers) are used in a PCR or extension reaction and then excess primer is removed using a single stranded nuclease. Subsequent rounds of PCR or extension may be performed using different primers (e.g., second tail primers or nested primers or a second target specific primer) to incorporate different sequences into the resulting products.

In some embodiments, an exonuclease (e.g., ExoI) may be used to degrade single-stranded DNA. In some embodiments, an exonuclease is used to degrade ssDNA and the amplified product is processed directly according to steps $109_{A-B}$ and $110_{A-B}$, without purification at step 108.

In FIG. 1A, at step $109_A$, amplified DNA products of step 107 (e.g., as purified in step 108) are contacted with a second target-specific primer and a second tail primer. In some embodiments, the second target-specific primer hybridizes to a sequence that is present within the template DNA molecule 3' of the sequence of the first target-specific primer such that the reactions are nested. In some embodiments, nesting of the second target-specific primer relative to the first target-specific primer may improve specificity of the hybridization reaction. In some embodiments, the second target-specific primer may comprise an additional sequence 5' to the hybridization sequence that may include barcode, index, adapter sequences, or sequencing primer sites, for example. In step $110_A$, the amplified DNA products of step 107 (e.g., as purified in step 108) are amplified by PCR in which the extensions are primed by the second target-specific primer and a second tail primer. In some embodiments, a portion of the amplified product from step 107 is further amplified. In some embodiments, a third primer is used that hybridizes to the common tail in the second target specific primer and adds additional sequences such as a barcodes, adapters, etc.

In some embodiments, the second target-specific primer comprises a nucleotide sequence 5' to the target-specific sequence that comprises a barcode, index, or adapter sequences. In some embodiments, the second tail primer hybridizes to a sequence that is present within the template DNA molecule 3' of the sequence of the first tail primer such that the reactions are nested. In such embodiments, a portion of the product from step 106 is amplified. In some embodiments, the second tail primer may comprise additional sequences 5' to the hybridization sequence that may include barcode, index, adapter sequences or sequencing primer sites. Hybridization of the second target-specific primer and the second tail primer allows for exponential amplification of a portion of the target nucleic acid molecule in a PCR reaction.

In some embodiment, the first target-specific primer of step 106 may be used with a second target-specific primer. In such embodiments, hybridization of the first target-specific primer and the second target-specific primer allows for amplification of product in a polymerase chain reaction (PCR). In some embodiments, steps 108-110 may be omitted. The amplification products are purified in reaction 111 and ready for analysis. For example, products purified in step 111 can be sequenced (e.g., using a next generation sequencing platform.) In some embodiments the first target-specific primer or second target-specific primer may comprise additional sequences 5' to a hybridization sequence that may include barcode, index, adapter sequences or sequencing primer sites.

In some embodiments, as depicted in FIG. 1B, in step $109_B$, DNA products of step 107 (e.g., as purified in step 108) are contacted with a second target-specific primer and a second tail primer. The second target-specific primer is further contacted by an additional primer (e.g., a primer having 3' sequencing adapter/index sequences) that hybridizes with the common sequence of the second target-specific primer. In some embodiments the additional primer may comprise additional sequences 5' to the hybridization sequence that may include barcode, index, adapter sequences or sequencing primer sites. In some embodiments, the additional primer is a generic sequencing adapter/index primer. In some embodiments, the second target-specific primer may be nested relative to the target-specific primer used in step 107. In step $110_B$, the DNA products of step 107 (e.g., as purified in step 108) are amplified by PCR in which the extensions are primed by the second target-specific primer and a second tail primer. Hybridization of the second target-specific primer, the additional primer, and the second tail primer allows for exponential amplification of a portion of the target nucleic acid molecule in a PCR reaction. In such embodiments, a portion of the amplified product from step 108 is amplified.

In some embodiment, the first tail primer of step 106 may be used with a second target-specific primer. In such embodiments, hybridization of the first tail primer and the second target-specific primer allows for amplification of product in a polymerase chain reaction (PCR), optionally with an additional primer (e.g., a primer having 3' sequencing adapter/index sequences) that hybridizes with the common sequence of the second target-specific primer. In some embodiments, steps 108-110 may be omitted.

The products are purified in reaction 111 and ready for analysis. For example, products purified in step 111 can be sequenced (e.g., using a next generation sequencing platform).

In some embodiments, steps 101-104, 106-107, and 109-110 are performed consecutively in a single reaction tube without any intervening purification steps. In some embodiments, all of the components involved in steps 101-104, 106-107, 109-110 are present at the outset and throughout the reaction. In some embodiments, steps 101-104 are performed consecutively in a single reaction tube. In some embodiments, all of the components involved in steps 101-104 are present at the outset and throughout the reaction. In some embodiments, steps 106-107 are performed consecutively in a single reaction tube. In some embodiments, all of the components involved in steps 106-107 are present at the outset and throughout the reaction. In some embodiments, steps $109_A$-$110_A$ or $109_B$-$110_B$ are performed consecutively in a single reaction tube. In some embodiments, all of the components involved in steps $109_A$-$110_A$ or $109_B$-$110_B$ are present at the outset and throughout the reaction.

Figure 2A:
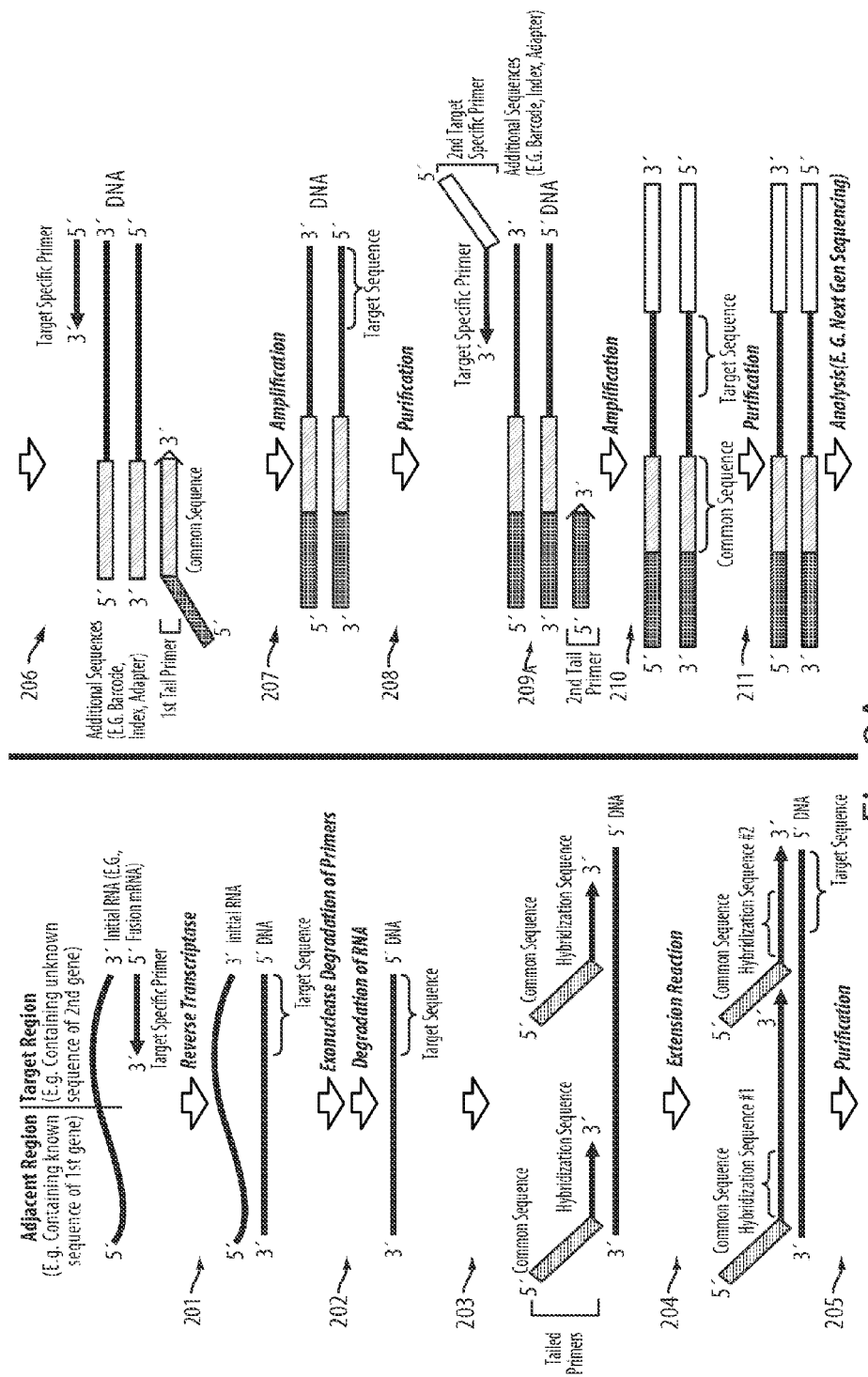
FIGS. 2A and 2B depict non-limiting embodiments of a work flow for amplifying sequencing target nucleic acids that are flanked by a 5' unknown fusion partner, as described herein.
Figure 2B:
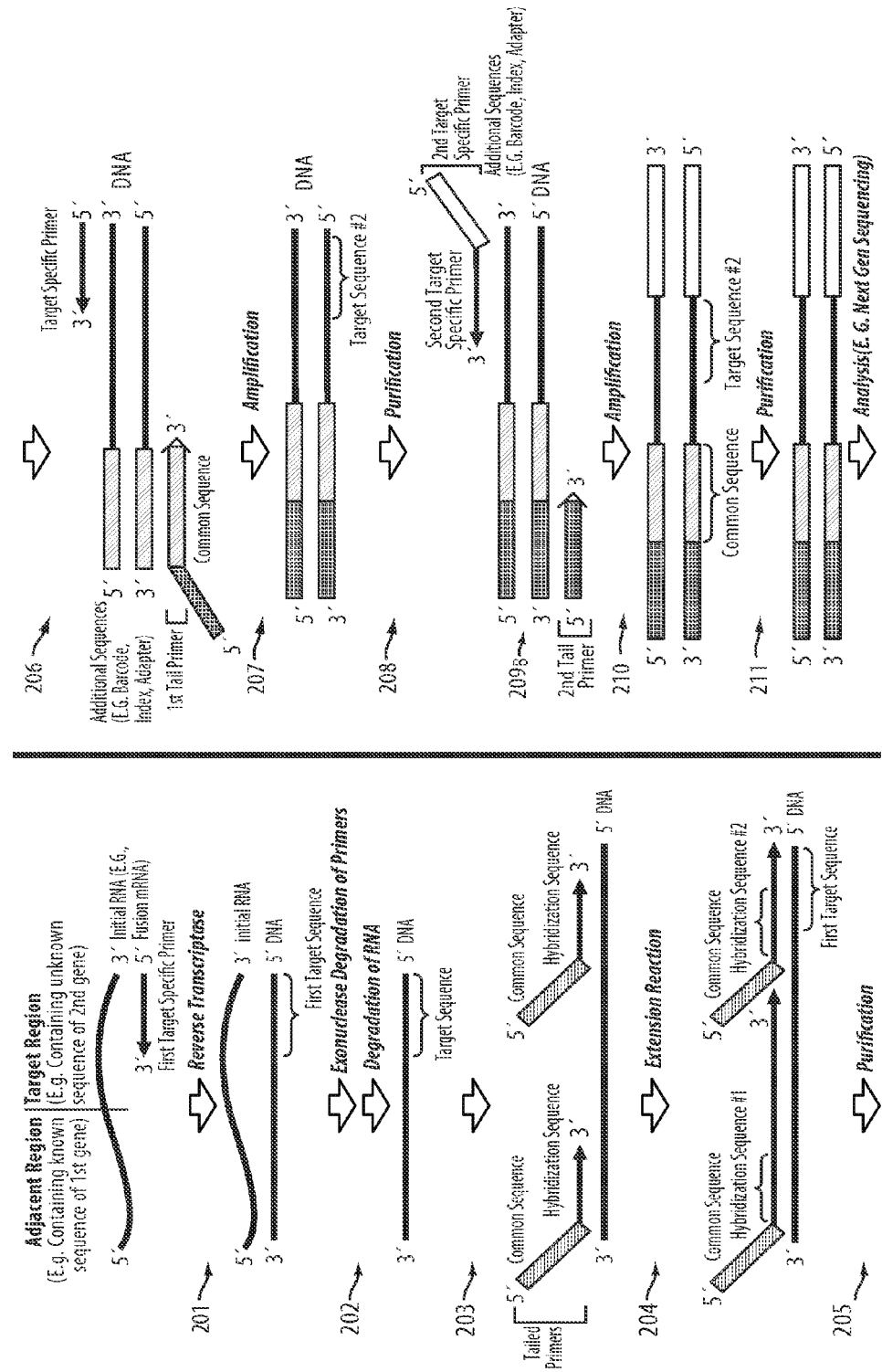

In some embodiments, methods are provided for preparing nucleic acids that have a target region 3' to an adjacent region (e.g., an adjacent region of unknown sequence content). For example, FIG. 2 presents a schematic of an exemplary method of amplifying and sequencing target nucleic acids that have a known target region 3' to an adjacent region. In FIGS. 2A-B, an initial RNA (e.g., a fusion mRNA) is obtained or provided in a sample and is used as a template for the proceeding method. At step 201, the RNA template is exposed to one or more initial target-specific primers that hybridize to one or more target nucleotide sequences and function to prime a reverse transcription reaction such that a complementary DNA molecule is produced using the initial RNA as a template. In some embodiments, an initial target-specific primer hybridizes to the poly-A tail of an RNA template. In some embodiments, the sequence of the primer that hybridizes to the poly-A tail comprises a poly-dT (e.g., a 3' positioned stretch of 2 dTs, 3 dTs, 4 dTs, 5 dTs, 6 dTs, 7 dTs, 8 dTs, 9 dTs, 10 dTs, or more). In step 202 the unhybridized primers are degraded (e.g., enzymatically, e.g., by an exonuclease). In step 202, RNA template is degraded from the complementary DNA strand (e.g., enzymatically, e.g., by RNaseH).

In step 203, DNA molecules that were generated by reverse transcription are contacted by a heterogenous population of tailed primers (e.g., tailed random primers). In some embodiments, the tail portion of each of the tailed primers is a shared or common sequence, identical between all primers of the population of tailed primers. In some embodiments, at least one primer comprises a hybridization sequence that is complementary to and hybridizes to the target acid template. In step 204, tailed primers that are hybridized with the template nucleic acid are extended in a template-dependent extension reaction to produce complementary DNA strands that incorporate the tailed primer sequence and the template sequence. The resulting double stranded DNA product is purified in step 205.

In step 206, DNA products purified in step 205 are contacted with a first target-specific primer and a first tail primer. The first target-specific primer hybridizes to a target sequence (region) of the DNA. The first tail primer hybridizes to a portion of the DNA molecule characteristic of the tail of the tailed primers of step 203. In some embodiments, the first tail primer hybridizes to the common sequence provided by the tail of the one or more primers of step 203. In some embodiments, a first tail primer comprises a barcode or index sequence. In step 207 hybridization of the first target-specific primer and the first tail primer facilitates exponential amplification of a portion of the target nucleic acid molecule in an amplification reaction (e.g., a PCR reaction). In some embodiments, the first tail primer may comprise additional sequences 5' to the hybridization sequence that may include barcode, index, adapter sequences or sequencing primer sites. Amplified products are purified in step 208. In some embodiments, the purification in step 208 is skipped. For example, in some embodiments, primers (e.g., second target specific primers and $2^{nd}$ tail primers) are used in a PCR or extension reaction and then excess primer is removed using a single stranded DNA nuclease. Subsequent rounds of PCR or extension may be performed using different primers to incorporate different sequences into the resulting products.

In some embodiments, as depicted in FIG. 2A at step 209$_A$, DNA molecules produced in step 207 (e.g., as purified in step 208) are contacted with a second target-specific primer and a second tail primer. In some embodiments, the second target-specific primer is nested relative to the target specific primer used in step 207. In some embodiments, at least a portion of the product from step 209$_A$ is amplified.

In some embodiments, the second target-specific primer comprises a nucleotide sequence 5' to the target-specific sequence that comprises a barcode, index, or adapter sequences. In some embodiments, the second tail primer hybridizes to a sequence that is present within the template DNA molecule 3' of the sequence of the first tail primer such that the reactions are nested. In some embodiments, at least a portion of the product from step 209$_A$ is amplified.

In some embodiments, first tail primer of step 206 may be used with a second target-specific primer. In such embodiments, hybridization of the first tail primer and the second target-specific primer allows for amplification of product in a polymerase chain reaction (PCR). In such embodiments, steps 208-210 may be omitted.

In some embodiments, as depicted in FIG. 2B at step 209$_B$, DNA molecules produced in step 207 (e.g., as purified in step 208) are contacted with a second target-specific primer and a second tail primer wherein the second target-specific primer hybridizes to a target sequence that is present within the template DNA molecule 3' of the sequence of the first target-specific primer such that the reactions are nested. In some embodiments, at least a portion of the product from step 209$_B$ is amplified.

In some embodiments, the second target-specific primer is further contacted by an additional primer (e.g., a primer having 3' sequencing adapter/index sequences) that hybridizes with the common sequence of the second target-specific primer. In some embodiments the additional primer may comprise additional sequences 5' to the hybridization sequence that may include barcode, index, adapter sequences or sequencing primer sites. In some embodiments, the additional primer is a generic sequencing adapter/index primer. In such embodiments, hybridization of the second target-specific primer, the additional primer, and a second tail primer allows for exponential amplification of a portion of the target nucleic acid molecule in a PCR reaction.

In some embodiments, the second target-specific primer comprises a nucleotide sequence 5' to the target-specific sequence that comprises a barcode, index, or adapter sequences. In some embodiments, the second tail primer hybridizes to a sequence that is present within the template DNA molecule 3' of the sequence of the first tail primer such that the reactions are nested. In some embodiments, at least a portion of the product from step 209$_B$ is amplified.

In some embodiments, the second tail primer may comprise additional sequence 5' to the hybridization sequence that may include barcode, index, adapter sequences or sequencing primer sites. In step 210, hybridization of the second target-specific primer and the second tail primer facilitates exponential amplification of a portion of the target nucleic acid molecule in an amplification reaction (e.g., a PCR reaction). The amplification product of step 210 is purified in reaction 211 and ready for analysis. For example, products purified in step 211 can be sequenced (e.g., using a next generation sequencing platform.)

In some embodiments, steps 201-204 are performed consecutively in a single reaction tube. In some embodiments, all of the components involve in steps 201-204 are present at the outset and throughout the reaction. In some embodiments, steps 206-207 are performed consecutively in a single reaction tube. In some embodiments, all of the components involve in steps 206-207 are present at the outset and throughout the reaction. In some embodiments, steps 209$_A$-210 or 209$_B$-210 are performed consecutively in a single reaction tube. In some embodiments, all of the components involve in steps 209$_A$-210 or 209$_B$-210 are present at the outset and throughout the reaction.

In some embodiments, methods provided herein involve use of random sequences as molecular barcodes. In some embodiments, molecular barcodes are built into primers (e.g., RT primers, target-specific primers, extension sequence primers) such that each individual molecule produced by a primer obtains a unique barcode tag. Thus, in some embodiments, the molecular barcode tag permits a determination of whether a sequenced molecular is unique. In some embodiments, molecular barcodes may be used to silence sequencing errors, improve confidence calling of fusions or other mutations, and improved detection limits.

Figure 3:
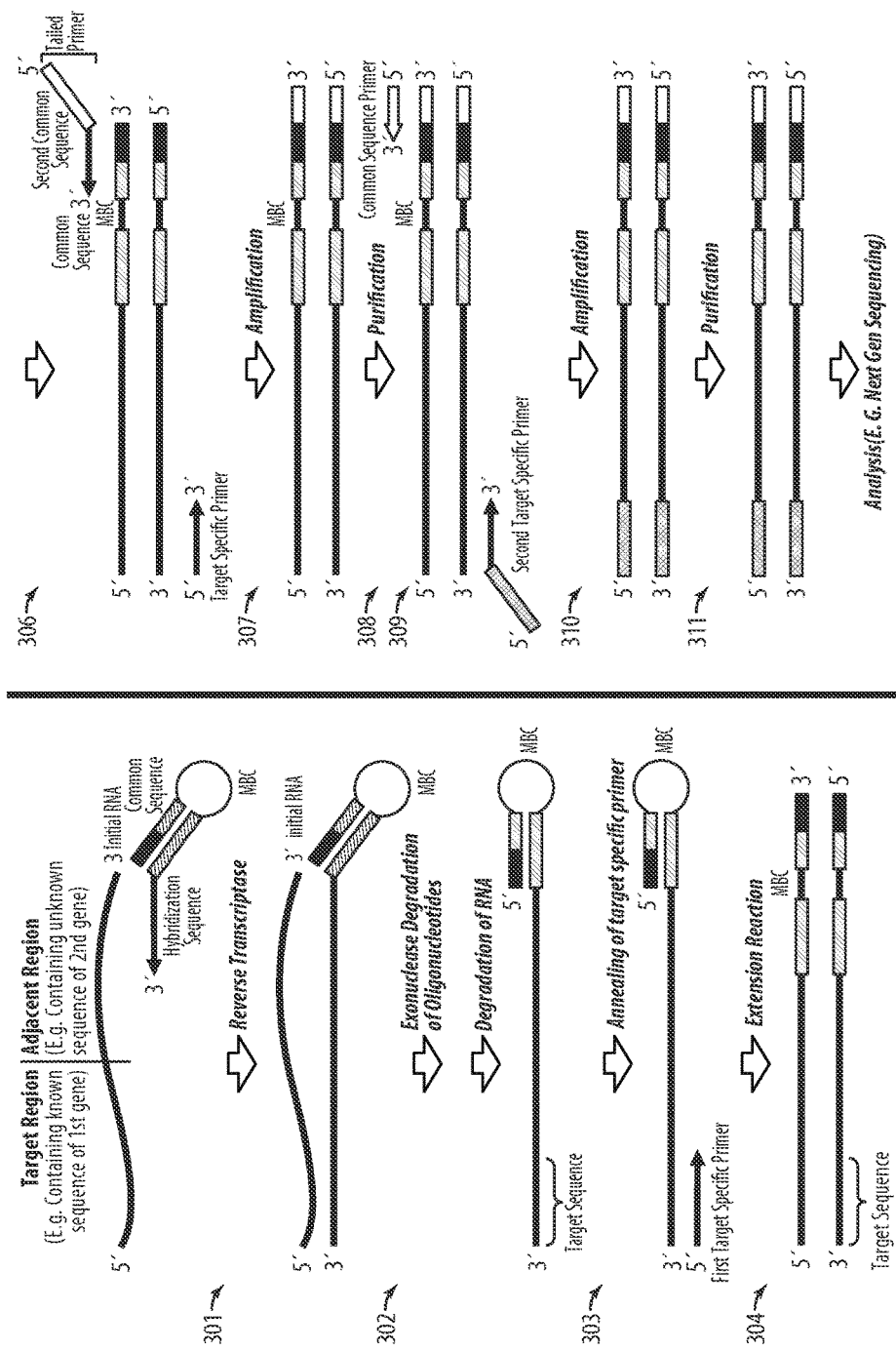
FIG. 3 depicts a non-limiting embodiment of a work flow for amplifying sequencing target nucleic acids that are flanked by a 3' unknown fusion pattern using an oligonucleotide comprising a hairpin, as described herein.

In some embodiments, methods are provided for preparing nucleic acids that have a target region 5' to an adjacent region (e.g., an adjacent region of unknown sequence) using an oligonucleotide comprising a hairpin. In some embodiments, the oligonucleotide may have a structure that is not a hairpin, for example, the oligonucleotide may be linear. For example, FIG. 3 presents a schematic of an exemplary method for amplifying target nucleic acids that have a known target region 5' to an adjacent region (for purposes of sequencing the adjacent region). At step 301, an initial RNA is obtained or provided in a sample and is used as a template for the proceeding method. The RNA template is exposed to a plurality of hairpin primers (e.g., random primers with a hairpin tail) that comprise a hairpin sequence that is 5' to different hybridization sequences and shared between all of the primers of the population. The hairpin sequence comprises two complementary common sequences that flank a molecular barcode sequence (MBC). The complementary common sequences base pair to form the stem-loop hairpin structure and protect the MBC sequence. In some embodiments, the plurality of primers is in another structure (not a hairpin) and comprises two complementary common sequences that flank a molecular barcode sequence (MBC). In some embodiments, at least one primer hybridizes to the RNA molecule and primes a reverse transcriptase reaction to produce a complementary DNA strand. In some embodiments, a primer hybridizes to the poly-A tail of the RNA molecule. In some embodiments, the sequence of the primer that hybridizes to the poly-A tail comprises a poly-dT (e.g., a 3' positioned stretch of 2 dTs, 3 dTs, 4 dTs, 5 dTs, 6 dTs, 7 dTs, 8 dTs, 9 dTs, 10 dTs, or more.). In step 302, any unhybridized oligonucleotides are enzymatically degraded (e.g., by an exonuclease). Also in step 302, the RNA template is enzymatically degraded from the complementary DNA strand (e.g., by RNaseH).

In step 303, DNA molecules produced by reverse transcription are contacted by one or more initial target-specific primers which may or may not be the same as the first target-specific primer. In step 304, hybridization of the first target-specific primer to a portion of the target nucleic acid primes an extension reaction using the DNA molecule as a template to produce a complementary DNA strand. In some embodiments, synthesis of the complementary DNA strand may reduce or eliminate hairpin formation of the complementary common sequences. Extension products are purified in step 305.

In step 306, DNA molecules are contacted by a first target-specific primer and a tailed primer. The first target-specific primer hybridizes to a portion of the target nucleic acid. The first tail primer hybridizes to a portion of the DNA molecule provided by the common sequence involve in hairpin formation step 301. In some embodiments, a nested target-specific primer (e.g., nested with respect to the target-specific primer of step 303) is used in step 306. In some embodiments, the first tailed primer may comprise an additional sequence 5' to the hybridization sequence that may include barcode, index, adapter sequences, or sequencing primer sites, for example. In step 307, hybridization of each of the first target-specific primer and the tailed primer allows for amplification of a portion of the target nucleic acid molecule in a polymerase chain reaction (PCR). In some embodiments, amplified products are purified in step 308.

In step 309, amplified DNA products (e.g., those purified in step 308) are contacted with a second target-specific primer and a common sequence primer. In some embodiments, the second target-specific primer hybridizes to a sequence that is present within the template DNA molecule 3' of the sequence of the first target-specific primer such that the reactions are nested. In some embodiments, the common sequence primer hybridizes with a sequence provided by the first tail primer in step 306. In some embodiments, in step 310, DNA products purified in step 308 are amplified by PCR in which the extensions are primed by a second target-specific primer and a common sequence primer. In some embodiments, amplified product from step 308 may be amplified.

In some embodiments, the second target-specific primer comprises a nucleotide sequence 5' to the target-specific sequence that comprises a barcode, index, or adapter sequences. In some embodiments, the second tail primer hybridizes to a sequence that is present within the template DNA molecule 3' of the sequence of the first tail primer such that the reactions are nested. In such embodiments, a portion of the product from step 308 is amplified. In some embodiments, the common sequence primer may comprise additional sequences 5' to the hybridization sequence that may include barcode, index, adapter sequences or sequencing primer sites. Hybridization of the second target-specific primer and the common sequence primer allows for exponential amplification of a portion of the target nucleic acid molecule in a PCR reaction. In some embodiments, products are purified in reaction 311 useful for analysis. For example, products purified in step 311 can be sequenced (e.g., using a next generation sequencing platform.)

In some embodiments, all of the components involved in steps 301-311 are present at the outset and throughout the reaction. In some embodiments, steps 301-304, 306-307, and 309-310 are performed consecutively in a single reaction tube without any intervening purification steps. In some embodiments, steps 301-304 are performed consecutively in a single reaction tube. In some embodiments, all of the components involve in steps 301-304 are present at the outset and throughout the reaction. In some embodiments, steps 306-307 are performed consecutively in a single reaction tube. In some embodiments, all of the components involve in steps 306-307 are present at the outset and throughout the reaction. In some embodiments, steps 309-310 are performed consecutively in a single reaction tube. In some embodiments, all of the components involve in steps 309-310 are present at the outset and throughout the reaction.

In some embodiments, methods are provided herein that involve determining the nucleotide sequence contiguous to (adjacent to) a known target nucleotide sequence. In some embodiments, methods comprise contacting a target nucleic acid molecule comprising the known target nucleotide sequence with an initial target-specific primer under suitable hybridization conditions. In some embodiments, the methods further comprise maintaining the target nucleic acid molecule under conditions that promote extension of the hybridized initial target-specific primer (e.g., using the target nucleic acid molecule as a template), thereby producing a first extension product. In some embodiments, the methods further comprise contacting the extension product with a population of tailed random primers under suitable hybridization conditions. In some embodiments, the methods further comprise maintaining the extension product under conditions that promote extension of a hybridized tailed random primer using the portion of the target nucleic acid molecule downstream of the site of hybridization as a template, thereby producing a second extension product. In some embodiments, the methods further comprise amplifying a portion of the target nucleic acid molecule and the tailed random primer sequence with a first tail primer and a first target-specific primer, thereby producing a first amplicon. In some embodiments, the methods further comprise amplifying a portion of the amplicon with a second tail primer and a second target-specific primer, thereby producing a second amplicon.

In some embodiments, one or more target-specific primers used in the methods may be nested with respect to one or more other target-specific primers. For example, in some embodiments, a second target-specific primer is internal to a first target-specific primer. In some embodiments, target-specific primers are the same. In some embodiments, target-specific primers are nested but overlapping with respect to target complementarity. In some embodiments, target-specific primers are nested and non-overlapping. In some embodiments, combinations of identical and nested target specific primers are used in the same or different amplification steps. In some embodiments, nesting of primers increases target specificity. In some embodiments, the methods further comprise sequencing the second amplicon using a first and second sequencing primer. In some embodiments, the population of tailed random primers comprises single-stranded oligonucleotide molecules having a 5' nucleotide sequence identical to a first sequencing primer and a 3' nucleotide comprising from random nucleotides (e.g., about 6 to about 12 random nucleotides). In some embodiments, the first target-specific primer comprises a nucleic acid sequence that can specifically anneal to the known nucleotide sequence of the target nucleic acid at an appropriate annealing temperature. In some embodiments, the second target-specific primer comprises a 3' portion comprising a nucleic acid sequence that can specifically anneal to a portion of the known target nucleotide sequence comprised by the first amplicon, and a 5' portion comprising a nucleic acid sequence that is identical to a second sequencing primer and the second target-specific primer is nested with respect to the first target-specific primer. In some embodiments, the first tail primer comprises a nucleic acid sequence identical to the common sequence of the tail of the tailed random primer. In some embodiments, the common sequence on the tailed random primer is the exact match of the common sequence on the first tail primer. In some embodiments, the second tail primer comprises a nucleic acid sequence identical to a portion of the first sequencing primer and is nested with respect to the first tail primer.

As used herein, the term "target nucleic acid" refers to a nucleic acid molecule of interest (e.g., an nucleic acid to be analyzed). In some embodiments, a target nucleic acid comprises both a target nucleotide sequence (e.g., a known or predetermined nucleotide sequence) and an adjacent nucleotide sequence which is to be determined (which may be referred to as an unknown sequence). A target nucleic acid can be of any appropriate length. In some embodiments, a target nucleic acid is double-stranded. In some embodiments, the target nucleic acid is DNA. In some embodiments, the target nucleic acid is genomic or chromosomal DNA (gDNA). In some embodiments, the target nucleic acid can be complementary DNA (cDNA). In some embodiments, the target nucleic acid is single-stranded. In some embodiments, the target nucleic acid can be RNA, e.g., mRNA, rRNA, tRNA, long non-coding RNA, microRNA.

As used herein, the term "known target nucleotide sequence" refers to a portion of a target nucleic acid for which the sequence (e.g. the identity and order of the nucleotide bases of the nucleic acid) is known. For example, in some embodiments, a known target nucleotide sequence is a nucleotide sequence of a nucleic acid that is known or that has been determined in advance of an interrogation of an adjacent unknown sequence of the nucleic acid. A known target nucleotide sequence can be of any appropriate length.

In some embodiments, a target nucleotide sequence (e.g., a known target nucleotide sequence) has a length of 10 or more nucleotides, 30 or more nucleotides, 40 or more nucleotides, 50 or more nucleotides, 100 or more nucleotides, 200 or more nucleotides, 300 or more nucleotides, 400 or more nucleotides, 500 or more nucleotides. In some embodiments, a target nucleotide sequence (e.g., a known target nucleotide sequence) has a length in range of 10 to 100 nucleotides, 10 to 500 nucleotides, 10 to 1000 nucleotides, 100 to 500 nucleotides, 100 to 1000 nucleotides, 500 to 1000 nucleotides, 500 to 5000 nucleotides.

In some embodiments, methods are provided herein for determining sequences of contiguous (or adjacent) portions of a nucleic acid. As used herein, the term "nucleotide sequence contiguous to" refers to a nucleotide sequence of a nucleic acid molecule (e.g., a target nucleic acid) that is immediately upstream or downstream of another nucleotide sequence (e.g., a known nucleotide sequence). In some embodiments, a nucleotide sequence contiguous to a known target nucleotide sequence may be of any appropriate length. In some embodiments, a nucleotide sequence contiguous to a known target nucleotide sequence comprises 1 kb or less of nucleotide sequence, e.g. 1 kb or less of nucleotide sequence, 750 bp or less of nucleotide sequence, 500 bp or less of nucleotide sequence, 400 bp or less of nucleotide sequence, 300 bp or less of nucleotide sequence, 200 bp or less of nucleotide sequence, 100 bp or less of nucleotide sequence. In some embodiments, in which a sample comprises different target nucleic acids comprising a known target nucleotide sequence (e.g. a cell in which a known target nucleotide sequence occurs multiple times in its genome, or on separate, non-identical chromosomes), there may be multiple sequences which comprise "a nucleotide sequence contiguous to" the known target nucleotide sequence. As used herein, the term "determining a (or the) nucleotide sequence," refers to determining the identity and relative positions of the nucleotide bases of a nucleic acid.

In some embodiments of methods disclosed herein one or more tailed random primers are hybridized to a nucleic acid template (e.g., a template comprising a strand of a target nucleic acid). In some embodiments, a target nucleic acid is present in or obtained from a sample comprising a plurality of nucleic acids, one or more of which plurality do not comprise the target nucleic acid. In some embodiments, one or more primers (e.g., one or more tailed random primers) hybridize to substantially all of the nucleic acids in a sample. In some embodiments, one or more primers (e.g., one or more tailed random primers) hybridize to nucleic acids that comprise a target nucleic acid and to nucleic acids that do not comprise the target nucleotide sequence.

Aspects of certain methods disclosed herein relate to contacting a nucleic acid template with a plurality of different primers that share a common sequence that is 5' (or upstream) to different hybridization sequences. In some embodiments the plurality of different primers may be referred to as a population of different primers. In some embodiments, the common sequence may be referred to as a tail, as such the primers are referred to as "tailed primers." In some embodiments, different hybridization sequences of a population comprise nucleotide sequences that occur randomly or pseudorandomly within the population. In some embodiments, nucleotide sequences that occur randomly within a population contain no recognizable regularities, such that, for each nucleotide of each sequence in the population, there is an equal likelihood that the nucleotide comprises a base that is complementary with A, T, G, or C. In such embodiments, it should be appreciated that each nucleotide comprising a base that is complementary with A, T, G, or C may be a naturally occurring nucleotide, a non-naturally occurring nucleotide or a modified nucleotide.

As used herein, a "common sequence" or "shared sequence" refers to a nucleotide sequence that is present in each nucleic acid of a population of nucleic acids. In some embodiments, the common sequence is in a range of about 4 to 75, 4 to 50, 4 to 30, or 4 to 20 nucleotides in length. In some embodiments, the common sequence is 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 nucleotides in length.

As used herein, the term "tailed random primer" refers to a single-stranded nucleic acid molecule having a 5' nucleotide sequence (e.g., a 5' nucleotide sequence identical or complementary to a first sequencing primer) and a 3' nucleic acid sequence, in which the 3' nucleotide comprises random nucleotides (e.g., from about 3 to about 15 random nucleotides, about 6 to about 12 random nucleotides). In some embodiments, the 3' nucleotide sequence comprising random nucleotides is at least 6 nucleotides in length, e.g. 6 nucleotides or more, 7 nucleotides or more, 8 nucleotides or more, 9 nucleotides or more, 10 nucleotides or more, 11 nucleotides or more, 12 nucleotides or more, 13 nucleotides or more, 14 nucleotides or more, 15 nucleotides or more, 20 nucleotides or more, 25 nucleotides or more in length. In some embodiments, the 3' nucleotide sequence comprising random nucleotides is 3 to 6 nucleotides in length, 3 to 9 nucleotides in length, 3 to 12 nucleotides in length, 5 to 9 nucleotides in length, 6 to 12 nucleotides in length, 3 to 25 nucleotides in length, 6 to 15 nucleotides in length, or 6 to 25 nucleotides in length. In some embodiments, a tailed random primer can further comprise a spacer between the 5' nucleotide sequence and the 3' nucleotide sequence comprising about 6 to about 12 random nucleotides. In some embodiments, the spacer is a molecular barcode, e.g., that independently tags a template nucleic acid (e.g., a template RNA). In some embodiments, the spacer may be 3 to 6 nucleotides in length, 3 to 12 nucleotides in length, 3 to 25 nucleotides in length, 3 to 45 nucleotides in length, 6 to 12 nucleotides in length, 8 to 16 nucleotides in length, 6 to 25 nucleotides in length, or 6 to 45 nucleotides in length. In some embodiments, for a populations of primers, the spacer is composed of random nucleotides (e.g., in which each of N is independently selected from A, G, C, and T). In some embodiments, the spacer (e.g., a molecular barcode(MBC)) is flanked by two common regions that are complementary. In some embodiments, the complementary common regions base pair to form the stem of a hairpin having a loop portion that comprises the MBC (e.g., as depicted in FIG. 3). In some embodiments, this hairpin configuration protects the MBC from annealing to other targets inhibiting the RT reaction of the extension reaction in the case of 5' fusions. In some embodiments, a population of tailed random primers can comprise individual primers with varying 3' sequences. In some embodiments, a population of tailed random primers can comprise individual primers with identical 5' nucleotide sequences, e.g., they are all compatible with the same sequencing primer. In some embodiments, a population of tailed random primers can comprise individual primers with varying 5' nucleotide sequences, e.g. an first individual primer is compatible with a first sequencing primer and a second individual primer is compatible with a second sequencing primer.

As used herein, a "hybridization sequence" refers to a sequence of a nucleic acid, such as a portion of a primer, that that has sufficient complementary with a sequence of another nucleic acid (e.g., a template molecule, a target sequence) to enable hybridization between nucleic acid. In some embodiments, the hybridization sequence is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides in length. In some embodiments, the hybridization sequence is in a range of 5 to 50 nucleotides in length, 5 to 40 nucleotides in length, 5 to 35 nucleotides in length, 5 to 30 nucleotides in length, 5 to 25 nucleotides in length, 5 to 20 nucleotides in length, 5 to 15 nucleotides in length, 5 to 10 nucleotides in length, 10 to 40 nucleotides in length, 10 to 30 nucleotides in length, or 10 to 20 nucleotides in length.

In some embodiments, methods described herein comprises an extension regimen or step. In such embodiments, extension may proceed from one or more hybridized tailed random primers, using the nucleic acid molecules which the primers are hybridized to as templates. Extension steps are described herein. In some embodiments, one or more tailed random primers can hybridize to substantially all of the nucleic acids in a sample, many of which may not comprise a known target nucleotide sequence. Accordingly, in some embodiments, extension of random primers may occur due to hybridization with templates that do not comprise a known target nucleotide sequence.

In some embodiments, methods described herein may involve a polymerase chain reaction (PCR) amplification regimen, involving one or more amplification cycles. As used herein, the term "amplification regimen" refers to a process of specifically amplifying (increasing the abundance of) a nucleic acid of interest. In some embodiments, exponential amplification occur when products of a previous polymerase extension serve as templates for successive rounds of extension. In some embodiments, a PCR amplification regimen according to methods disclosed herein may comprise at least one, and in some cases at least 5 or more iterative cycles. In some embodiments each iterative cycle comprises steps of: 1) strand separation (e.g., thermal denaturation); 2) oligonucleotide primer annealing to template molecules; and 3) nucleic acid polymerase extension of the annealed primers. In should be appreciated that any suitable conditions and times involved in each of these steps may be used. In some embodiments, conditions and times selected may depend on the length, sequence content, melting temperature, secondary structural features, or other factors relating to the nucleic acid template and/or primers used in the reaction. In some embodiments, an amplification regimen according to methods described herein is performed in a thermal cycler, many of which are commercially available.

In some embodiments, a nucleic acid extension reaction involves the use of a nucleic acid polymerase. As used herein, the phrase "nucleic acid polymerase" refers an enzyme that catalyzes the template-dependent polymerization of nucleoside triphosphates to form primer extension products that are complementary to the template nucleic acid sequence. A nucleic acid polymerase enzyme initiates synthesis at the 3' end of an annealed primer and proceeds in the direction toward the 5' end of the template. Numerous nucleic acid polymerases are known in the art and commercially available. One group of nucleic acid polymerases are thermostable, i.e., they retain function after being subjected to temperatures sufficient to denature annealed strands of complementary nucleic acids, e.g. 94° C., or sometimes higher. A non-limiting example of a protocol for amplification involves using a polymerase (e.g., Phoenix Taq, VeraSeq) under the following conditions: 98° C. for 30 s, following by 14-22 cycles comprising melting at 98° C. for 10 s, followed by annealing at 68° C. for 30 s, followed by extension at 72° C. 3 min, followed by holding of the reaction at 4° C. However, other appropriate reaction conditions may be used. In some embodiments, annealing/extension temperatures may be adjusted to account for differences in salt concentration (e.g., 3° C. higher to higher salt concentrations). In some embodiments, slowing the ramp rate (e.g., 1° C./s, 0.5° C./s, 0.28° C./s, 0.1° C./s or slower), for example, from 98° C. to 65° C., improves primer performance and coverage uniformity in highly multiplexed samples.

In some embodiments, a nucleic acid polymerase is used under conditions in which the enzyme performs a template-dependent extension. In some embodiments, the nucleic acid polymerase is DNA polymerase I, Taq polymerase, Pheonix Taq polymerase, Phusion polymerase, T4 polymerase, T7 polymerase, Klenow fragment, Klenow exo-, phi29 polymerase, AMV reverse transcriptase, M-MuLV reverse transcriptase, HIV-1 reverse transcriptase, VeraSeq ULtra polymerase, VeraSeq HF 2.0 polymerase, EnzScript or another appropriate polymerase. In some embodiments, a nucleic acid polymerase is not a reverse transcriptase. In some embodiments, a nucleic acid polymerase acts on a DNA template. In some embodiments, the nucleic acid polymerase acts on an RNA template. In some embodiments, an extension reaction involves reverse transcription performed on an RNA to produce a complementary DNA molecule (RNA-dependent DNA polymerase activity). In some embodiments, a reverse transcriptase is a mouse molony murine leukemia virus (M-MLV) polymerase, AMV reverse transcriptase, RSV reverse transcriptase, HIV-1 reverse transcriptase, HIV-2 reverse transcriptase or another appropriate reverse transcriptase.

In some embodiments, a nucleic acid amplification reaction involves cycles including a strand separation step generally involving heating of the reaction mixture. As used herein, the term "strand separation" or "separating the strands" means treatment of a nucleic acid sample such that complementary double-stranded molecules are separated into two single strands available for annealing to an oligonucleotide primer. In some embodiments, strand separation according to methods described herein is achieved by heating the nucleic acid sample above its melting temperature ($T_m$). In some embodiments, for a sample containing nucleic acid molecules in a reaction preparation suitable for a nucleic acid polymerase, heating to 94° C. is sufficient to achieve strand separation. In some embodiments, a suitable reaction preparation contains one or more salts (e.g., 1 to 100 mM KCl, 0.1 to 10 $MgCl_2$), at least one buffering agent (e.g., 1 to 20 mM Tris-HCL), and a carrier (e.g., 0.01 to 0.5% BSA). A non-limiting example of a suitable buffer comprises 50 mM KCl, 10 mM Tris-HCl (pH 8.8@25° C.), 0.5 to 3 mM $MgCl_2$, and 0.1% BSA.

In some embodiments, a nucleic acid amplification involves annealing primers to nucleic acid templates having a strands characteristic of a target nucleic acid. In some embodiments, a strand of a target nucleic acid can serve as a template nucleic acid.

As used herein, the term "anneal" refers to the formation of one or more complementary base pairs between two nucleic acids. In some embodiments, annealing involve two complementary or substantially complementary nucleic acids strands hybridizing together. In some embodiments, in the context of an extension reaction annealing involves the hybridize of primer to a template such that a primer extension substrate for a template-dependent polymerase enzyme is formed. In some embodiments, conditions for annealing (e.g., between a primer and nucleic acid template) may vary based of the length and sequence of a primer. In some embodiments, conditions for annealing are based upon a $T_m$ (e.g., a calculated $T_m$) of a primer. In some embodiments, an annealing step of an extension regimen involves reducing the temperature following strand separation step to a temperature based on the $T_m$ (e.g., a calculated $T_m$) for a primer, for a time sufficient to permit such annealing. In some embodiments, a $T_m$ can be determined using any of a number of algorithms (e.g., OLIGO™ (Molecular Biology Insights Inc. Colorado) primer design software and VENTRO NTI™ (Invitrogen, Inc. California) primer design software and programs available on the internet, including Primer3, Oligo Calculator, and NetPrimer (Premier Biosoft; Palo Alto, Calif.; and freely available on the world wide web (e.g., at premierbiosoft.com/netprimer/netprlaunch/Help/xnetpr-launch.html). In some embodiments, the $T_m$ of a primer can be calculated using following formula, which is used by NetPrimer software and is described in more detail in Frieir et al. PNAS 1986 83:9373-9377 which is incorporated by reference herein in its entirety.

$$T_m = \Delta H/(\Delta S + R^* \ln(C/4)) + 16.6 \log([K^+]/(1+0.7[K^+])) - 273.15$$

wherein, $\Delta H$ is enthalpy for helix formation; $\Delta S$ is entropy for helix formation; R is molar gas constant (1.987 cal/° C.*mol); C is the nucleic acid concentration; and $[K^+]$ is salt concentration. For most amplification regimens, the annealing temperature is selected to be about 5° C. below the predicted $T_m$, although temperatures closer to and above the $T_m$ (e.g., between 1° C. and 5° C. below the predicted $T_m$ or between 1° C. and 5° C. above the predicted $T_m$) can be used, as can, for example, temperatures more than 5° C. below the predicted $T_m$ (e.g., 6° C. below, 8° C. below, 10° C. below or lower). In some embodiments, the closer an annealing temperature is to the $T_m$, the more specific is the annealing. In some embodiments, the time used for primer annealing during an extension reaction (e.g., within the context of a PCR amplification regimen) is determined based, at least in part, upon the volume of the reaction (e.g., with larger volumes involving longer times). In some embodiments, the time used for primer annealing during an extension reaction (e.g., within the context of a PCR amplification regimen) is determined based, at least in part, upon primer and template concentrations (e.g., with higher relative concentrations of primer to template involving less time than lower relative concentrations). In some embodiments, depending upon volume and relative primer/template concentration, primer annealing steps in an extension reaction (e.g., within the context of an amplification regimen) can be in the range of 1 second to 5 minutes, 10 seconds and 2 minutes, or 30 seconds to 2 minutes. As used herein, "substantially anneal" refers to an extent to which complementary base pairs form between two nucleic acids that, when used in the context of a PCR amplification regimen, is sufficient to produce a detectable level of a specifically amplified product.

As used herein, the term "polymerase extension" refers to template-dependent addition of at least one complementary nucleotide, by a nucleic acid polymerase, to the 3' end of an primer that is anneal to a nucleic acid template. In some embodiments, polymerase extension adds more than one nucleotide, e.g., up to and including nucleotides corresponding to the full length of the template. In some embodiments, conditions for polymerase extension are based, at least in part, onthe identity of the polymerase used. In some embodiments, the temperature used for polymerase extension is based upon the known activity properties of the enzyme. In some embodiments, in which annealing temperatures are below the optimal temperatures for the enzyme, it may be acceptable to use a lower extension temperature. In some embodiments, enzymes may retain at least partial activity below their optimal extension temperatures. In some embodiments, a polymerase extension (e.g., performed thermostable polymerases) (e.g., Taq polymerase and variants thereof) is performed at 65° C. to 75° C. or 68° C. to 72° C. In some embodiments, methods provided herein involve polymerase extension of primers that are anneal to nucleic acid templates at each cycle of a PCR amplification regimen. In some embodiments, a polymerase extension is performed using a polymerase that has relatively strong strand displacement activity. In some embodiments, polymerases having strong strand displacement are useful for preparing nucleic acids for purposes of detecting fusions (e.g., 5' fusions).

In some embodiments, primer extension is performed under conditions that permit the extension of annealed oligonucleotide primers. As used herein, the term "conditions that permit the extension of an annealed oligonucleotide such that extension products are generated" refers to the set of conditions including, for example temperature, salt and co-factor concentrations, pH, and enzyme concentration under which a nucleic acid polymerase catalyzes primer extension. In some embodiments, such conditions are based, at least in part, on the nucleic acid polymerase being used. In some embodiments, a polymerase may perform a primer extension reaction in a suitable reaction preparation. In some embodiments, a suitable reaction preparation contains one or more salts (e.g., 1 to 100 mM KCl, 0.1 to 10 $MgCl_2$), at least one buffering agent (e.g., 1 to 20 mM Tris-HCL), a carrier (e.g., 0.01 to 0.5% BSA) and one or more NTPs (e.g, 10 to 200 uM of each of dATP, dTTP, dCTP, and dGTP). non-limiting set of conditions is 50 mM KCl, 10 mM Tris-HCl (pH 8.8@25° C.), 0.5 to 3 mM $MgCl_2$, 200 uM each dNTP, and 0.1% BSA at 72° C., under which a polymerase (e.g., Taq polymerase) catalyzes primer extension. In some embodiments, conditions for initiation and extension may include the presence of one, two, three or four different deoxyribonucleoside triphosphates (e.g., selected from dATP, dTTP, dCTP, and dGTP) and a polymerization-inducing agent such as DNA polymerase or reverse transcriptase, in a suitable buffer. In some embodiments, a "buffer" may include solvents (e.g., aqueous solvents) plus appropriate cofactors and reagents which affect pH, ionic strength, etc.).

In some embodiments, nucleic acid amplification involve up to 5, up to 10, up to 20, up to 30, up to 40 or more rounds (cycles) of amplification. In some embodiments, nucleic acid amplification may comprise a set of cycles of a PCR amplification regimen from 5 cycles to 20 cycles in length. In some embodiments, an amplification step may comprise a set of cycles of a PCR amplification regimen from 10 cycles to 20 cycles in length. In some embodiments, each amplification step can comprise a set of cycles of a PCR amplification regimen from 12 cycles to 16 cycles in length. In some embodiments, an annealing temperature can be less than 70° C. In some embodiments, an annealing temperature can be less than 72° C. In some embodiments, an annealing temperature can be about 65° C. In some embodiments, an annealing temperature can be from about 61 to about 72° C.

In various embodiments, methods and compositions described herein relate to performing a PCR amplification regimen with one or more of the types of primers described herein. As used herein, "primer" refers to an oligonucleotide capable of specifically annealing to a nucleic acid template and providing a 3' end that serves as a substrate for a template-dependent polymerase to produce an extension product which is complementary to the template. In some embodiments, a primer useful in methods described herein is single-stranded, such that the primer and its complement can anneal to form two strands. Primers according to methods and compositions described herein may comprise a hybridization sequence (e.g., a sequence that anneals with a nucleic acid template) that is less than or equal to 300 nucleotides in length, e.g., less than or equal to 300, or 250, or 200, or 150, or 100, or 90, or 80, or 70, or 60, or 50, or 40, or 30 or fewer, or 20 or fewer, or 15 or fewer, but at least 6 nucleotides in length. In some embodiments, a hybridization sequence of a primer may be 6 to 50 nucleotides in length, 6 to 35 nucleotides in length, 6 to 20 nucleotides in length, 10 to 25 nucleotides in length.

Any suitable method may be used for synthesizing oligonucleotides and primers. In some embodiments, commercial sources offer oligonucleotide synthesis services suitable for providing primers for use in methods and compositions described herein, e.g. INVITROGEN™ Custom DNA Oligos; Life Technologies; Grand Island, N.Y. or custom DNA Oligos from IDT; Coralville, Iowa).

In some embodiments, after an extension from a tailed random primer has occurred, the extension product and template can be amplified in a first amplification step. In some embodiments, amplification may involve a set of PCR amplification cycles using a first target-specific primer and a first tail primer. In some embodiments, the amplification may result in at least part of the tailed random primer sequence present in the extension product being amplified. In some embodiments, the amplification may result in all of the tailed random primer sequence present in the extension product being amplified.

As used herein, the term "first target-specific primer" refers to a single-stranded oligonucleotide comprising a nucleic acid sequence that can specifically anneal under suitable annealing conditions to a nucleic acid template that has a strand characteristic of a target nucleic acid.

In some embodiments, a primer (e.g., a target specific primer) can comprise a 5' tag sequence portion. In some embodiments, multiple primers (e.g., all first-target specific primers) present in a reaction can comprise identical 5' tag sequence portions. In some embodiments, in a multiplex PCR reaction, different primer species can interact with each other in an off-target manner, leading to primer extension and subsequently amplification by DNA polymerase. In such embodiments, these primer dimers tend to be short, and their efficient amplification can overtake the reaction and dominate resulting in poor amplification of desired target sequence. Accordingly, in some embodiments, the inclusion of a 5' tag sequence in primers (e.g., on target specific primer(s)) may result in formation of primer dimers that contain the same complementary tails on both ends. In some embodiments, in subsequent amplification cycles, such primer dimers would denature into single-stranded DNA primer dimers, each comprising complementary sequences on their two ends which are introduced by the 5' tag. In some embodiments, instead of primer annealing to these single stranded DNA primer dimers, an intra-molecular hairpin (a panhandle like structure) formation may occur due to the proximate accessibility of the complementary tags on the same primer dimer molecule instead of an inter-molecular interaction with new primers on separate molecules. Accordingly, in some embodiments, these primer dimers may be inefficiently amplified, such that primers are not exponentially consumed by the dimers for amplification; rather the tagged primers can remain in high and sufficient concentration for desired specific amplification of target sequences. In some embodiments, accumulation of primer dimers may be undesirable in the context of multiplex amplification because they compete for and consume other reagents in the reaction.

In some embodiments, a 5' tag sequence can be a GC-rich sequence. In some embodiments, a 5' tag sequence may comprise at least 50% GC content, at least 55% GC content, at least 60% GC content, at least 65% GC content, at least 70% GC content, at least 75% GC content, at least 80% GC content, or higher GC content. In some embodiments, a tag sequence may comprise at least 60% GC content. In some embodiments, a tag sequence may comprise at least 65% GC content.

In some embodiments, a target-specific primer (e.g., a second target-specific primer) is a single-stranded oligonucleotide comprising a 3' portion comprising a nucleic acid sequence that can specifically anneal to a portion of a known target nucleotide sequence of an amplicon of an amplification reaction, and a 5' portion comprising a tag sequence (e.g., a nucleotide sequence that is identical to or complementary to a sequencing primer (e.g., a second sequencing primer).

In some embodiments, a second target-specific primer of an amplification regimen is nested with respect to a first target-specific primer of the amplification regimen. In some embodiments, the second target-specific primer is nested with respect to the first target-specific primer by at least 3 nucleotides, e.g. by 3 or more, 4 or more, 5 or more, 6 or more, 7 or more, 8 or more, 9 or more, 10 or more, or 15 or more nucleotides. In some embodiments, all of the target-specific primers (e.g., second target-specific primers) used in an amplification regimen comprise the same 5' portion. In some embodiments, the 5' portion target-specific primer can be configured to suppress primer dimers as described herein.

In some embodiments, first and second target-specific primers are used in an amplification regimen that are substantially complementary to the same strand of a target nucleic acid. In some embodiments, portions of the first and second target-specific primers that specifically anneal to a target sequence (e.g., a known target sequence) can comprise a total of at least 20 unique bases of the known target nucleotide sequence, e.g. 20 or more unique bases, 25 or more unique bases, 30 or more unique bases, 35 or more unique bases, 40 or more unique bases, or 50 or more unique bases. In some embodiments, portions of first and second target-specific primers that specifically anneal to a target sequence (e.g., a known target sequence) can comprise a total of at least 30 unique bases of the known target nucleotide sequence.

As used herein, the term "first tail primer" refers to a nucleic acid molecule comprising a nucleic acid sequence identical to the tail portion of tailed primer.

As used herein, the term "second tail primer" refers to a nucleic acid molecule comprising a nucleic acid sequence identical to a portion of a first sequencing primer, adapter, index primer, etc. and is optionally nested with respect to a first tailed primer. In some embodiments, the second tail primer sits outside of the first tail primer to facilitate addition of appropriate index tags, adapters (e.g., for use in a sequencing platform), etc. In some embodiments, a second tailed primer is identical to a sequencing primer. In some embodiments, a second tailed primer is complementary to a sequencing primer.

In some embodiments, a second tail primer is nested with respect to a first tail primer. In some embodiments, a second tail primer is not nested with respect to a first tail primer. In some embodiments, tail primers of an amplification regimen are nested with respect to one another by at least 3 nucleotides, e.g. by 3 nucleotides, by 4 nucleotides, by 5 nucleotides, by 6 nucleotides, by 7 nucleotides, by 8 nucleotides, by 9 nucleotides, by 10 nucleotides or more.

In some embodiments, a first tail primer comprises a nucleic acid sequence identical to or complementary to the extension product of step (b) strand which is not comprised by the second tail primer and which is located closer to the 5' end of the tailed random primer than any of the sequence identical to or complementary to the second tail primer. Thus, in some embodiments, a second tail primer sits outside of a region added by a random tail primer (5' end), e.g., within the 5' tail added by the first tail primers.

In some embodiments, a first tail primer can comprise a nucleic acid sequence identical to or complementary to a stretch (e.g., of about 20 nucleotides) of the 5'-most nucleotides of a tailed random primer, and a second tail primer can comprise a nucleic acid sequence identical to or complementary to about 30 bases of a tailed random primer, with a 5' nucleotides that is at least 3 nucleotides 3' of the 5' terminus of the tailed random primer.

In some embodiments, use of nested tail primers minimizes or eliminates the production of final amplicons that are amplifiable (e.g. during bridge PCR or emulsion PCR) but cannot be sequenced, a situation that can arise during hemi-nested methods. In some embodiments, hemi-nested approaches using a primer identical to a sequencing primer can result in the carry-over of undesired amplification products from a first PCR step to a second PCR step and may yield artificial sequencing reads. In some embodiments, the use of two tail primers, as described herein can reduce, and in some embodiments eliminate, these problems.

In some embodiments, in a first PCR amplification cycle of a first amplification step, a first target-specific primer can specifically anneal to a template strand of any nucleic acid comprising the known target nucleotide sequence. In some embodiments, depending upon the orientation with which the first target-specific primer was designed, sequence upstream or downstream of the known target nucleotide sequence, and complementary to the template strand will be synthesized. In some embodiments, in which an extension product is formed that comprises the hybridization sequence with which the first target-specific primer forms complementary base pairs, a double-stranded amplification product can be formed that comprises the first target-specific primer (and the sequence complementary thereto), the target nucleotide sequence downstream of the first target-specific primer (and the sequence complementary thereto), and the tailed random primer sequence (and the sequence complementary thereto). In such embodiments, in subsequent PCR amplification cycles, both the first target-specific primer and the first tail primer are capable of specifically annealling to appropriate strands of the amplification product and the sequence between the known nucleotide target sequence and the tailed random primer can be amplified.

In some embodiments, of methods described herein, a portion of an amplified product (an amplicon) is amplified in further rounds of amplification. In some embodiments, the further rounds of amplification may involve PCR amplification cycles performed using a second target-specific primer and a first sequencing primer or a second tail primer. In some embodiments, a PCR amplification cycles may involve the use of PCR parameters identical to, or which differ from, those of one or more other (e.g., prior) of PCR amplification cycles. In some embodiments, PCR amplification regimens can have the same or different annealing temperatures or the same or different extension step time lengths.

In some embodiments, methods described herein allow for determining the nucleotide sequence contiguous to a known target nucleotide sequence on either or both flanking regions of the known target nucleotide sequence. Regardless of whether the target nucleic acid normally exists as a single-stranded or double-stranded nucleic acid, sequence information may be represented in a single-stranded format (Strand A), from 5' to 3'. In some embodiments, if the sequence 5' to a known target nucleotide sequence of Strand A is to be determined, gene-specific primers can be complementary to (anneal to) Strand A. If the sequence 3' to a known target nucleotide sequence of Strand A is to be determined, the gene-specific primers can be identical to Strand A, such that they will anneal to the complementary strand of a double-stranded target nucleic acid.

In some embodiments, methods described herein, relating to the use of a first and second gene-specific primer can result in assays with a superior on-target rate, e.g. 70-90%. In some embodiments, the assays and methods described herein can have a target specificity rate of at least 85%.

In some embodiments, primers disclosed herein (e.g., target-specific primers, tail primers) are designed such that they will specifically anneal to their complementary sequences at an annealing temperature of from about 61 to 72° C., e.g. from about 61 to 69° C., from about 63 to 69° C., from about 63 to 67° C., from about 64 to 66° C. In some embodiments, primers disclosed herein are designed such that they will specifically anneal to their complementary sequences at an annealing temperature of less than 72° C. In some embodiments, primers disclosed herein are designed such that they will specifically anneal to their complementary sequences at an annealing temperature of less than 70° C. In some embodiments, primers disclosed herein are designed such that they will specifically anneal to their complementary sequences at an annealing temperature of less than 68° C. In some embodiments, primers disclosed herein are designed such that they will specifically anneal to their complementary sequences at an annealing temperature of about 65° C.

In some embodiments, portions of the target-specific primers that specifically anneal to the known target nucleotide sequence will anneal specifically at a temperature of about 61 to 72° C., e.g. from about 61 to 69° C., from about 63 to 69° C., from about 63 to 67° C., from about 64 to 66° C. In some embodiments, portions of the target-specific primers that specifically anneal to the known target nucleotide sequence will anneal specifically at a temperature of about 65° C. in a PCR buffer.

In some embodiments, primers described herein do not comprise modified bases (e.g. the primers can not comprise a blocking 3' amine). However, in some embodiments, primers described herein do comprise modified or non-naturally occurring bases. In some embodiments, primers may be modified with a label capable of providing a detectable signal, either directly or indirectly. Non-limiting examples of such labels include radioisotopes, fluorescent molecules, biotin, and others. In some embodiments, primers disclosed herein may include contain a biotin linker or other suitable linker (e.g., for conjugating the primer to a support). In some embodiments, primer may contain a target sequence of an endonucleases such that cleavage with the appropriate enzyme. In other embodiments, the 5' end of a primer may include a sequence that is complementary with a nucleic acid bound to a bead or other support, e.g., a flow cell substrate. Primers may or may not comprise modified internucleoside linkages.

In some embodiments, of methods described herein, nucleic acids (e.g., amplified nucleic acids, extension products, target nucleic acids) can be sequenced. In some embodiments, sequencing can be performed by a next-generation sequencing method. As used herein "next-generation sequencing" refers to oligonucleotide sequencing technologies that have the capacity to sequence oligonucleotides at speeds above those possible with conventional sequencing methods (e.g. Sanger sequencing), due to performing and reading out thousands to millions of sequencing reactions in parallel. Non-limiting examples of next-generation sequencing methods/platforms include Massively Parallel Signature Sequencing (Lynx Therapeutics); 454 pyrosequencing (454 Life Sciences/Roche Diagnostics); solid-phase, reversible dye-terminator sequencing (Solexa/Illumina): SOLiD technology (Applied Biosystems); Ion semiconductor sequencing (ION Torrent); DNA nanoball sequencing (Complete Genomics); and technologies available from Pacific Biosciences, Intelligen Bio-systems, Oxford Nanopore Technologies, and Helicos Biosciences. In some embodiments, the sequencing primers can comprise portions compatible with the selected next-generation sequencing method. Next-generation sequencing technologies and the constraints and design parameters of associated sequencing primers are well known in the art (see, e.g. Shendure, et al., "Next-generation DNA sequencing," Nature, 2008, vol. 26, No. 10, 1135-1145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11(3):333-43; Zhang et al., "The impact of next-generation sequencing on genomics", J Genet Genomics, 2011, 38(3): 95-109; (Nyren, P. et al. Anal Biochem 208: 17175 (1993); Bentley, D. R. Curr Opin Genet Dev 16:545-52 (2006); Strausberg, R. L., et al. Drug Disc Today 13:569-77 (2008); U.S. Pat. No. 7,282,337; 7,279,563; 7,226,720; 7,220,549; 7,169,560; 6,818,395; 6,911,345; US Pub. Nos. 2006/0252077; 2007/0070349; and 20070070349; which are incorporated by reference herein in their entireties).

In some embodiments, the sequencing step involve the use of a first and second sequencing primers. In some embodiments, the first and second sequencing primers are selected to be compatible with a next-generation sequencing method as described herein.

Methods of aligning sequencing reads to known sequence databases of genomic and/or cDNA sequences are well known in the art and software is commercially available for this process. In some embodiments, reads (less the sequencing primer nucleotide sequence) which do not map, in their entirety, to wild-type sequence databases can be genomic rearrangements or large indel mutations. In some embodiments, reads (less the sequencing primer nucleotide sequence) comprising sequences which map to multiple locations in the genome can be genomic rearrangements.

In some embodiments, primers may contain additional sequences such as an identifier sequence (e.g., a barcode, an index), sequencing primer hybridization sequences (e.g., Rd1), and adapter sequences. In some embodiments the adapter sequences are sequences used with a next generation sequencing system. In some embodiments, the adapter sequences are P5 and P7 sequences for Illumina-based sequencing technology. In some embodiments, the adapter sequence are P1 and A compatible with Ion Torrent sequencing technology.

In some embodiments, as used herein, a "barcode," "molecular barcode," "molecular barcode tag" and "index" may be used interchangeably. generally referring to a nucleotide sequence of a nucleic acid that is useful as an identifier, such as, for example, a source identifier, location identifier, date or time identifier (e.g., date or time of sampling or processing), or other identifier of the nucleic acid. In some embodiments, such barcode or index sequences are useful for identifying different aspects of a nucleic acid that is present in a population of nucleic acids. In some embodiments, barcode or index sequences may provide a source or location identifier for a target nucleic acid. For example, a barcode or index sequence may serve to identify a patient from whom a nucleic acid is obtained. In some embodiments, barcode or index sequences enable sequencing of multiple different samples on a single reaction (e.g., performed in a single flow cell). In some embodiments, an index sequence can be used to orientate a sequence imager for purposes of detecting individual sequencing reactions. In some embodiments, a barcode or index sequence may be 2 to 25 nucleotides in length, 2 to 15 nucleotides in length, 2 to 10 nucleotides in length, 2 to 6 nucleotides in length. In some embodiments, a barcode or index comprise at least 2, 3, 4, 5, 6, 7, 8, 9, 10, 11, 12, 13, 14, 15, 16, 17, 18, 19, 20, 21, 22, 23, 24, or at least 25 nucleotides.

In some embodiments, when a population of tailed random primers is used in accordance with methods described herein, multiple distinguishable amplification products can be present after amplification. In some embodiments, because tailed random primers hybridize at various positions throughout nucleic acid molecules of a sample, a set of target-specific primers can hybridize (and amplify) the extension products created by more than 1 hybridization event, e.g. one tailed random primer may hybridize at a first distance (e.g., 100 nucleotides) from a target-specific primer hybridization site, and another tailed random primer can hybridize at a second distance (e.g., 200 nucleotides) from a target-specific primer hybridization site, thereby resulting in two amplification products (e.g., a ~100 bp amplification product and a ~200 bp amplification product). In some embodiments, these multiple amplification products can each be sequenced in. In some embodiments, sequencing of these multiple amplification products is advantageous because it provides multiple overlapping sequence reads that can be compare with one another to detect sequence errors introduced during amplification or sequencing processes. In some embodiments, individual amplification products can be aligned and where they differ in the sequence present at a particular base, an artifact or error of PCR and/or sequencing may be present.

In some embodiments, target nucleic acids and/or amplification products thereof can be isolated from enzymes, primers, or buffer components before and/or after any of appropriate step of a method. Any suitable methods for isolating nucleic acids may be usede. In some embodiments, the isolation can comprise Solid Phase Reversible Immobilization (SPRI) cleanup. Methods for SPRI cleanup are well known in the art and kits are commercially available, e.g. Agencourt AMPure XP-PCR Purification (Cat No. A63880, Beckman Coulter; Brea, Calif.). In some embodiments, enzymes can be inactivated by heat treatment.

In some embodiments, unhybridized primers can be removed from a nucleic acid preparation using appropriate methods (e.g., purification, digestion, etc.). In some embodiments, a nuclease (e.g., exonuclease I) is used to remove primer from a preparation. In some embodiments, such nucleases are heat inactivated subsequent to primer digestion. Once the nucleases are inactivated a further set of primers may be added together with other appropriate components (e.g., enzymes, buffers) to perform a further amplification reaction.

In some embodiments, a target nucleic acid genomic DNA or a portion thereof. In some embodiments, a target nucleic acid can be ribonucleic acid (RNA), e.g. mRNA, or a portion thereof. In some embodiments, a target nucleic acid can be a cDNA or a portion thereof.

Many of the sequencing methods suitable for use in methods described herein provide sequencing runs with optimal read lengths of tens to hundreds of nucleotide bases (e.g. Ion Torrent technology can produce read lengths of 200-400 bp). Target nucleic acids may or may not be substantially longer than this optimal read length. In some embodiments, in order for an amplified nucleic acid portion to be of a suitable length for use in a particular sequencing technology, the average distance between the known target nucleotide sequence and an end of the target nucleic acid to which a tailed random primer is hybridizable should be as close to the optimal read length of the selected technology as possible. In some embodiments, if the optimal read-length of a given sequencing technology is 200 bp, then the nucleic acid molecules amplified in accordance with methods described herein should have an average length of about 800 bp, about 700 bp, about 600 bp, about 500 bp, about 400 bp, about 300 bp, about 200 bp or less.

Nucleic acids used herein (e.g., prior to sequencing) can be sheared, e.g. mechanically or enzymatically sheared, to generate fragments of any desired size. Non-limiting examples of mechanical shearing processes include sonication, nebulization, and AFA™ shearing technology available from Covaris (Woburn, Mass.). In some embodiments, a nucleic acid can be mechanically sheared by sonication.

In some embodiments, a target nucleic acid is not sheared or digested. In some embodiments, nucleic acid products of preparative steps (e.g., extension products, amplification products) are not sheared or enzymatically digested.

In some embodiments, when a target nucleic acid an RNA, the sample can be subjected to a reverse transcriptase regimen to generate DNA template and the DNA template can then be sheared. In some embodiments, target RNA can be sheared before performing a reverse transcriptase regimen. In some embodiments, a sample comprising target RNA can be used in methods described herein using total nucleic acids extracted from either fresh or degraded specimens; without the need of genomic DNA removal for cDNA sequencing; without the need of ribosomal RNA depletion for cDNA sequencing; without the need of mechanical or enzymatic shearing in any of the steps; by subjecting the RNA for double-stranded cDNA synthesis using random hexamers.

In some embodiments, a known target nucleic acid can contain a fusion sequence resulting from a gene rearrangement. In some embodiments, methods described herein are suited for determining the presence and/or identity of a gene rearrangement. In some embodiments, identity of one portion of a gene rearrangement is previously known (e.g., the portion of a gene rearrangement that is to be targeted by the gene-specific primers) and the sequence of the other portion may be determined using methods disclosed herein. In some embodiments, a gene rearrangement can involves an oncogene. In some embodiments, a gene rearrangement can comprise a fusion oncogene.

In some embodiments, a target nucleic acid is present in or obtained from an appropriate sample (e.g., a food sample, environmental sample, biological sample e.g., blood sample, etc.). In some embodiments, the is a biological sample obtained from a subject. In some embodiments a sample can be a diagnostic sample obtained from a subject. In some embodiments, a sample can further comprise proteins, cells, fluids, biological fluids, preservatives, and/or other substances. By way of non-limiting example, a sample can be a cheek swab, blood, serum, plasma, sputum, cerebrospinal fluid, urine, tears, alveolar isolates, pleural fluid, pericardial fluid, cyst fluid, tumor tissue, tissue, a biopsy, saliva, an aspirate, or combinations thereof. In some embodiments, a sample can be obtained by resection or biopsy.

In some embodiments, the sample can be obtained from a subject in need of treatment for a disease associated with a genetic alteration, e.g. cancer or a hereditary disease. In some embodiments, a known target sequence is present in a disease-associated gene.

In some embodiments, a sample is obtained from a subject in need of treatment for cancer. In some embodiments, the sample comprises a population of tumor cells, e.g. at least one tumor cell. In some embodiments, the sample comprises a tumor biopsy, including but not limited to, untreated biopsy tissue or treated biopsy tissue (e.g. formalin-fixed and/or paraffin-embedded biopsy tissue).

In some embodiments, the sample is freshly collected. In some embodiments, the sample is stored prior to being used in methods and compositions described herein. In some embodiments, the sample is an untreated sample. As used herein, "untreated sample" refers to a biological sample that has not had any prior sample pre-treatment except for dilution and/or suspension in a solution. In some embodiments, a sample is obtained from a subject and preserved or processed prior to being utilized in methods and compositions described herein. By way of non-limiting example, a sample can be embedded in paraffin wax, refrigerated, or frozen. A frozen sample can be thawed before determining the presence of a nucleic acid according to methods and compositions described herein. In some embodiments, the sample can be a processed or treated sample. Exemplary methods for treating or processing a sample include, but are not limited to, centrifugation, filtration, sonication, homogenization, heating, freezing and thawing, contacting with a preservative (e.g. anti-coagulant or nuclease inhibitor) and any combination thereof. In some embodiments, a sample can be treated with a chemical and/or biological reagent. Chemical and/or biological reagents can be employed to protect and/or maintain the stability of the sample or nucleic acid comprised by the sample during processing and/or storage. In addition, or alternatively, chemical and/or biological reagents can be employed to release nucleic acids from other components of the sample. By way of non-limiting example, a blood sample can be treated with an anti-coagulant prior to being utilized in methods and compositions described herein. Suitable methods and processes for processing, preservation, or treatment of samples for nucleic acid analysis may be used in the method disclosed herein. In some embodiments, a sample can be a clarified fluid sample, for example, by centrifugation. In some embodiments, a sample can be clarified by low-speed centrifugation (e.g. 3,000×g or less) and collection of the supernatant comprising the clarified fluid sample.

In some embodiments, a nucleic acid present in a sample can be isolated, enriched, or purified prior to being utilized in methods and compositions described herein. Suitable methods of isolating, enriching, or purifying nucleic acids from a sample may be used. For example, kits for isolation of genomic DNA from various sample types are commercially available (e.g. Catalog Nos. 51104, 51304, 56504, and 56404; Qiagen; Germantown, Md.). In some embodiments, methods described herein relate to methods of enriching for target nucleic acids, e.g., prior to a sequencing of the target nucleic acids. In some embodiments, a sequence of one end of the target nucleic acid to be enriched is not known prior to sequencing. In some embodiments, methods described herein relate to methods of enriching specific nucleotide sequences prior to determining the nucleotide sequence using a next-generation sequencing technology. In some embodiments, methods of enriching specific nucleotide sequences do not comprise hybridization enrichment.

Methods described herein can be employed in a multiplex format. In embodiments of methods described herein, multiplex applications can include determining the nucleotide sequence contiguous to one or more known target nucleotide sequences. As used herein, "multiplex amplification" refers to a process involve simultaneous amplification of more than one target nucleic acid in one reaction vessel. In some embodiments, methods involve subsequent determination of the sequence of the multiplex amplification products using one or more sets of primers. Multiplex can refer to the detection of between about 2-1,000 different target sequences in a single reaction. As used herein, multiplex refers to the detection of any range between 2-1,000, e.g., between 5-500, 25-1000, or 10-100 different target sequences in a single reaction, etc. The term "multiplex" as applied to PCR implies that there are primers specific for at least two different target sequences in the same PCR reaction.

In some embodiments, target nucleic acids in a sample, or separate portions of a sample, can be amplified with a plurality of primers (e.g., a plurality of first and second target-specific primers). In some embodiments, the plurality of primers (e.g., a plurality of first and second target-specific primers) can be present in a single reaction mixture, e.g. multiple amplification products can be produced in the same reaction mixture. In some embodiments, the plurality of primers (e.g., a plurality of sets of first and second target-specific primers) can specifically anneal to known target sequences comprised by separate genes. In some embodiments, at least two sets of primers (e.g., at least two sets of first and second target-specific primers) can specifically anneal to different portions of a known target sequence. In some embodiments, at least two sets of primers (e.g., at least two sets of first and second target-specific primers) can specifically anneal to different portions of a known target sequence comprised by a single gene. In some embodiments, at least two sets of primers (e.g., at least two sets of first and second target-specific primers) can specifically anneal to different exons of a gene comprising a known target sequence. In some embodiments, the plurality of primers (e.g., first target-specific primers) can comprise identical 5' tag sequence portions.

In embodiments of methods described herein, multiplex applications can include determining the nucleotide sequence contiguous to one or more known target nucleotide sequences in multiple samples in one sequencing reaction or sequencing run. In some embodiments, multiple samples can be of different origins, e.g. from different tissues and/or different subjects. In such embodiments, primers (e.g., tailed random primers) can further comprise a barcode portion. In some embodiments, a primer (e.g., a tailed random primer) with a unique barcode portion can be added to each sample and ligated to the nucleic acids therein; the samples can subsequently be pooled. In such embodiments, each resulting sequencing read of an amplification product will comprise a barcode that identifies the sample containing the template nucleic acid from which the amplification product is derived.

In some embodiments of methods described herein, a determination of the sequence contiguous to a known oligonucleotide target sequence can provide information relevant to treatment of disease. Thus, in some embodiments, methods disclosed herein can be used to aid in treating disease. In some embodiments, a sample can be from a subject in need of treatment for a disease associated with a genetic alteration. In some embodiments, a known target sequence a sequence of a disease-associated gene, e.g. an oncogene. In some embodiments, a sequence contiguous to a known oligonucleotide target sequence and/or the known oligonucleotide target sequence can comprise a mutation or genetic abnormality which is disease-associated, e.g. a SNP, an insertion, a deletion, and/or a gene rearrangement. In some embodiments, a sequence contiguous to a known target sequence and/or a known target sequence present in a sample comprised sequence of a gene rearrangement product. In some embodiments, a gene rearrangement can be an oncogene, e.g. a fusion oncogene.

Certain treatments for cancer are particularly effective against tumors comprising certain oncogenes, e.g. a treatment agent which targets the action or expression of a given fusion oncogene can be effective against tumors comprising that fusion oncogene but not against tumors lacking the fusion oncogene. Methods described herein can facilitate a determination of specific sequences that reveal oncogene status (e.g. mutations, SNPs, and/or rearrangements). In some embodiments, methods described herein can further allow the determination of specific sequences when the sequence of a flanking region is known, e.g. methods described herein can determine the presence and identity of gene rearrangements involving known genes (e.g., oncogenes) in which the precise location and/or rearrangement partner are not known before methods described herein are performed.

In some embodiments, technology described herein relates to a method of treating cancer. Accordingly, in some embodiments, methods provided herein may involve detecting, in a tumor sample obtained from a subject in need of treatment for cancer, the presence of one or more oncogene rearrangements; and administering a cancer treatment which is effective against tumors having any of the detected oncogene rearrangements. In some embodiments, technology described herein relates to a method of determining if a subject in need of treatment for cancer will be responsive to a given treatment. Accordingly, in some embodiments, methods provided herein may involve detecting, in a tumor sample obtained from a subject, the presence of an oncogene rearrangement, in which the subject is determined to be responsive to a treatment targeting an oncogene rearrangement product if the presence of the oncogene rearrangement is detected.

In some embodiments, a subject is in need of treatment for lung cancer. In some embodiments, e.g. when the sample is obtained from a subject in need of treatment for lung cancer, the known target sequence can comprise a sequence from a gene selected from the group of ALK, ROS1, and RET. Accordingly, in some embodiments, gene rearrangements result in fusions involving the ALK, ROS1, or RET. Non-limiting examples of gene arrangements involving ALK, ROS1, or RET are described in, e.g., Soda et al. Nature 2007 448561-6: Rikova et al. Cell 2007 131:1190-1203; Kohno et al. Nature Medicine 2012 18:375-7; Takouchi et al. Nature Medicine 2012 18:378-81; which are incorporated by reference herein in their entireties. However, it should be appreciated that the precise location of a gene rearrangement, and the identity of the second gene involved in the rearrangement may not be known in advance. Accordingly, in methods described herein, the presence and identity of such rearrangements can be detected without having to know the location of the rearrangement or the identity of the second gene involved in the gene rearrangement.

In some embodiments, the known target sequence can comprise sequence from a gene selected from the group of: ALK, ROS1, and RET.

In some embodiments, the presence of a gene rearrangement of ALK in a sample obtained from a tumor in a subject can indicate that the tumor is susceptible to treatment with a treatment selected from the group consisting of: an ALK inhibitor; crizotinib (PF-02341066); AP26113; LDK378; 3-39; AF802; IPI-504; ASP3026; AP-26113; X-396; GSK-1838705A; CH5424802; diamino and aminopyrimidine inhibitors of ALK kinase activity such as NVP-TAE684 and PF-02341066 (see, e.g. Galkin et al, Proc Natl Acad Sci USA, 2007, 104:270-275; Zou et al. Cancer Res, 2007, 67:4408-4417; Hallberg and Palmer F1000 Med Reports 2011 3:21; and Sakamoto et al. Cancer Cell 2011 19:679-690) and molecules disclosed in WO 04/079326. All of the foregoing references are incorporated by reference herein in their entireties. An ALK inhibitor can include any agent that reduces the expression and/or kinase activity of ALK or a portion thereof, including, e.g. oligonucleotides, small molecules, and/or peptides that reduce the expression and/or activity of ALK or a portion thereof. As used herein "anaplastic lymphoma kinase" or "ALK" refers to a transmembrane tyROS line kinase typically involved in neuronal regulation in the wildtype form. The nucleotide sequence of the ALK gene and mRNA are known for a number of species, including human (e.g. SEQ ID NO: 2 (mRNA), NCBI Gene ID: 238).

In some embodiments, the presence of a gene rearrangement of ROS1 in a sample obtained from a tumor in a subject can indicate that the tumor is susceptible to treatment with a treatment selected from the group consisting of: a ROS1 inhibitor and an ALK inhibitor as described herein above (e.g. crizotinib). A ROS1 inhibitor can include any agent that reduces the expression and/or kinase activity of ROS1 or a portion thereof, including, e.g. oligonucleotides, small molecules, and/or peptides that reduce the expression and/or activity of ROS1 or a portion thereof. As used herein "c-ros oncogene 1" or "ROS1" (also referred to in the art as ros-1) refers to a transmembrane tyrosine kinase of the sevenless subfamily and which interacts with PTPN6. Nucleotide sequences of the ROS1 gene and mRNA are known for a number of species, including human (e.g. SEQ ID NO: 1 (mRNA), NCBI Gene ID: 238).

In some embodiments, the presence of a gene rearrangement of RET in a sample obtained from a tumor in a subject can indicate that the tumor is susceptible to treatment with a treatment selected from the group consisting of: a RET inhibitor; DP-2490, DP-3636, SU5416; BAY 43-9006, BAY 73-4506 (regorafenib), ZD6474, NVP-AST487, sorafenib, RPI-1, XL184, vandetanib, sunitinib, imatinib, pazopanib, axitinib, motesanib, gefitinib, and withaferin A (see, e.g. Samadi et al. Surgery 2010 148:1228-36; Cuccuru et al. JNCI 2004 13:1006-1014; Akeno-Stuart et al. Cancer Research 2007 67:6956; Grazma et al. J Clin Oncol 2010 28:15 s 5559; Mologni e tal. J Mol Endocrinol 2006 37:199-212; Calmomagno et al. Journal NCI 2006 98:326-334; Mologni. Curr Med Chem 2011 18:162-175 and the compounds disclosed in WO 06/034833; US Patent Publication 2011/0201598 and U.S. Pat. No. 8,067,434). All of the foregoing references are incorporated by reference herein in their entireties. A RET inhibitor can include any agent that reduces the expression and/or kinase activity of RET or a portion thereof, including, e.g. oligonucleotides, small molecules, and/or peptides that reduce the expression and/or activity of RET or a portion thereof. As used herein "rearranged during transfection" or "RET" refers to a receptor tyrosine kinase of the cad herein superfamily which is involved in neural crest development and recognizes glial cell line-derived neurotrophic factor family signaling molecules. Nucleotide sequences of the RET gene and mRNA are known for a number of species, including human (e.g. SEQ ID NOs: 3-4 (mRNA), NCBI Gene ID: 5979).

Further non-limiting examples of applications of methods described herein include detection of hematological malignancy markers and panels thereof (e.g. including those to detect genomic rearrangements in lymphomas and leukemias), detection of sarcoma-related genomic rearrangements and panels thereof; and detection of IGH/TCR gene rearrangements and panels thereof for lymphoma testing.

In some embodiments, methods described herein relate to treating a subject having or diagnosed as having, e.g. cancer with a treatment for cancer. Subjects having cancer can be identified by a physician using current methods of diagnosing cancer. For example, symptoms and/or complications of lung cancer which characterize these conditions and aid in diagnosis are well known in the art and include but are not limited to, weak breathing, swollen lymph nodes above the collarbone, abnormal sounds in the lungs, dullness when the chest is tapped, and chest pain. Tests that may aid in a diagnosis of, e.g. lung cancer include, but are not limited to, x-rays, blood tests for high levels of certain substances (e.g. calcium), CT scans, and tumor biopsy. A family history of lung cancer, or exposure to risk factors for lung cancer (e.g. smoking or exposure to smoke and/or air pollution) can also aid in determining if a subject is likely to have lung cancer or in making a diagnosis of lung cancer.

Cancer can include, but is not limited to, carcinoma, including adenocarcinoma, lymphoma, blastoma, melanoma, sarcoma, leukemia, squamous cell cancer, small-cell lung cancer, non-small cell lung cancer, gastrointestinal cancer, Hodgkin's and non Hodgkin's lymphoma, pancreatic cancer, glioblastoma, basal cell carcinoma, biliary tract cancer, bladder cancer, brain cancer including glioblastomas and medulloblastomas; breast cancer, cervical cancer, choriocarcinoma; colon cancer, colorectal cancer, endometrial carcinoma, endometrial cancer; esophageal cancer, gastric cancer; various types of head and neck cancers, intraepithelial neoplasms including Bowen's disease and Paget's disease; hematological neoplasms including acute lymphocytic and myelogenous leukemia; Kaposi's sarcoma, hairy cell leukemia; chromic myelogenous leukemia, AIDS-associated leukemias and adult T-cell leukemia lymphoma; kidney cancer such as renal cell carcinoma, T-cell acute lymphoblastic leukemia/lymphoma, lymphomas including Hodgkin's disease and lymphocytic lymphomas; liver cancer such as hepatic carcinoma and hepatoma, Merkel cell carcinoma, melanoma, multiple myeloma; neuroblastomas; oral cancer including squamous cell carcinoma; ovarian cancer including those arising from epithelial cells, sarcomas including leiomyosarcoma, rhabdomyosarcoma, liposarcoma, fibROS 1 arcoma, and osteosarcoma; pancreatic cancer; skin cancer including melanoma, stromal cells, germ cells and mesenchymal cells; pROS ltate cancer, rectal cancer; vulval cancer, renal cancer including adenocarcinoma; testicular cancer including germinal tumors such as seminoma, non-seminoma (teratomas, choriocarcinomas), stromal tumors, and germ cell tumors; thyroid cancer including thyroid adenocarcinoma and medullar carcinoma; esophageal cancer, salivary gland carcinoma, and Wilms' tumors. In some embodiments, the cancer can be lung cancer.

In some embodiments, methods described herein comprise administering an effective amount of compositions described herein, e.g. a treatment for cancer to a subject in order to alleviate a symptom of a cancer. As used herein, "alleviating a symptom of a cancer" is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic. The term "effective amount" as used herein refers to the amount of a treatment needed to alleviate at least one or more symptom of the disease or disorder, and relates to a sufficient amount of pharmacological composition to provide the desired effect. The term "therapeutically effective amount" therefore refers to an amount that is sufficient to effect a particular anti-cancer effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation. The effects of any particular dosage can be monitored by a suitable bioassay. The dosage can be determined by a physician and adjusted, as appropriate, to suit observed effects of the treatment.

Non-limiting examples of a treatment for cancer can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1 and calicheamicin omega1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. In addition, methods of treatment can further include the use of radiation or radiation therapy. Further, methods of treatment can further include the use of surgical treatments.

In some embodiments, methods described herein can be applicable for resequencing, e.g. for confirming particularly relevant, low-quality, and/or complex sequences obtained by non-directed sequencing of a large amount of nucleic acids. By way of non-limiting examples, methods described herein can allow the directed and/or targeted resequencing of targeted disease gene panels (e.g. 10-100 genes), resequencing to confirm variants obtained in large scale sequencing projects, whole exome resequencing, and/or targeted resequencing for detection of single nucleotide variants, multiple nucleotide variants, insertions, deletions, copy number changes, and methylation status.

In some embodiments, methods described herein can allow microbiota sequencing, ancient sample sequencing, and/or new variant virus genotyping.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein generally to mean a decrease by a statistically significant amount. However, for avoidance of doubt, "reduced", "reduction", "decrease", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference level), or any decrease between 10-100% as compared to a reference level. In the context of a marker or symptom is meant a statistically significant decrease in such level. The decrease can be, for example, at least 10%, at least 20%, at least 30%, at least 40% or more, and is preferably down to a level accepted as within the range of normal for an individual without such disorder.

The terms "increased", "increase", "enhance", or "activate" are all used herein to generally mean an increase by a statically significant amount; for the avoidance of doubt, the terms "increased", "increase", "enhance", or "activate" mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of, e.g. lung cancer. A subject can be male or female.

A subject can be one who has been previously diagnosed with or identified as suffering from or having a condition in need of treatment (e.g. cancer) or one or more complications related to such a condition, and optionally, have already undergone treatment for the condition or the one or more complications related to the condition. Alternatively, a subject can also be one who has not been previously diagnosed as having the condition (e.g. cancer) or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, a "disease associated with a genetic alteration" refers to any disease which is caused by, at least in part, by an alteration in the genetic material of the subject as compared to a healthy wildtype subject, e.g. a deletion, an insertion, a SNP, a gene rearrangement. A disease can be caused by, at least in part, an alteration in the genetic material of the subject if the alteration increases the risk of the subject developing the disease, increases the subject's susceptibility to a disease (including infectious diseases, or diseases with an infectious component), causes the production of a disease-associated molecule, or causes cells to become diseased or abnormal (e.g. loss of cell cycle regulation in cancer cells). Diseases can be associated with multiple genetic alterations, e.g. cancers.

As used herein, the term "nucleic acid" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA or cDNA. Other suitable nucleic acid molecules are RNA, including mRNA.

The term "isolated" or "partially purified" as used herein refers, in the case of a nucleic acid, to a nucleic acid separated from at least one other component (e.g., nucleic acid or polypeptide) that is present with the nucleic acid as found in its natural source and/or that would be present with the nucleic acid when expressed by a cell. A chemically synthesized nucleic acid or one synthesized using in vitro transcription/translation is considered "isolated."

As used herein, the term "complementary" refers to the ability of nucleotides to form hydrogen-bonded base pairs. In some embodiment, complementary refers to hydrogen-bonded base pair formation preferences between the nucleotide bases G, A, T, C and U, such that when two given polynucleotides or polynucleotide sequences anneal to each other, A pairs with T and G pairs with C in DNA, and G pairs with C and A pairs with U in RNA. As used herein, "substantially complementary" refers to a nucleic acid molecule or portion thereof (e.g. a primer) having at least 90% complementarity over the entire length of the molecule or portion thereof with a second nucleotide sequence, e.g. 90% complementary, 95% complementary, 98% complementary, 99% complementary, or 100% complementary. As used herein, "substantially identical" refers to a nucleic acid molecule or portion thereof having at least 90% identity over the entire length of a the molecule or portion thereof with a second nucleotide sequence, e.g. 90% identity, 95% identity, 98% identity, 99% identity, or 100% identity.

As used herein, "specific" when used in the context of a primer specific for a target nucleic acid refers to a level of complementarity between the primer and the target such that there exists an annealing temperature at which the primer will anneal to and mediate amplification of the target nucleic acid and will not anneal to or mediate amplification of non-target sequences present in a sample.

As used herein, "amplified product", "amplification product", or "amplicon" refers to oligonucleotides resulting from an amplificationreaction that are copies of a portion of a particular target nucleic acid template strand and/or its complementary sequence, which correspond in nucleotide sequence to the template nucleic acid sequence and/or its complementary sequence. An amplification product can further comprise sequence specific to the primers and which flanks sequence which is a portion of the target nucleic acid and/or its complement. An amplified product, as described herein will generally be double-stranded DNA, although reference can be made to individual strands thereof.

As used herein, a "portion" of a nucleic acid molecule refers to contiguous set of nucleotides comprised by that molecule. A portion can comprise all or only a subset of the nucleotides comprised by the molecule. A portion can be double-stranded or single-stranded.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. lung cancer. The term "treating" includes reducing or alleviating at least one adverse effect or symptom of a condition, disease or disorder associated with a condition. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

The term "statistically significant" or "significantly" refers to statistical significance and generally means a two standard deviation (2SD) below normal, or lower, concentration of the marker.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9). Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); and Davis et al., Basic Methods in Molecular Biology, Elsevier Science Publishing, Inc., New York, USA (1995) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, methodologies described in such publications that might be used in connection with technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if appropriate, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Technology described herein is further illustrated by the following examples which in no way should be construed as being further limiting.

Some embodiments of the technology described herein can be defined according to any of the following numbered paragraphs:

1. A method of determining the nucleotide sequence contiguous to a known target nucleotide sequence, the method comprising;
    (a) contacting a target nucleic acid molecule comprising the known target nucleotide sequence with an initial target-specific primer under hybridization conditions;
    (b) performing a template-dependent extension reaction that is primed by a hybridized initial target-specific primer and that uses the target nucleic acid molecule as a template;
    (c) contacting the product of step (b) with a population of tailed random primers under hybridization conditions;
    (d) performing a template-dependent extension reaction that is primed by a hybridized tailed random primer and that uses the portion of the target nucleic acid molecule downstream of the site of hybridization as a template;
    (e) amplifying a portion of the target nucleic acid molecule and the tailed random primer sequence with a first tail primer and a first target-specific primer;
    (f) amplifying a portion of the amplicon resulting from step (e) with a second tail primer and a second target-specific primer;
    (g) sequencing the amplified portion from step (f) using a first and second sequencing primer;
  wherein the population of tailed random primers comprises single-stranded oligonucleotide molecules having a 5' nucleic acid sequence identical to a first sequencing primer and a 3' nucleic acid sequence comprising from about 6 to about 12 random nucleotides;
  wherein the first target-specific primer comprises a nucleic acid sequence that can specifically anneal to the known target nucleotide sequence of the target nucleic acid at the annealing temperature;
wherein the second target-specific primer comprises a 3' portion comprising a nucleic acid sequence that can specifically anneal to a portion of the known target nucleotide sequence comprised by the amplicon resulting from step (e), and a 5' portion comprising a nucleic acid sequence that is identical to a second sequencing primer and the second target-specific primer is nested with respect to the first target-specific primer;
wherein the first tail primer comprises a nucleic acid sequence identical to the tailed random primer; and
wherein the second tail primer comprises a nucleic acid sequence identical to a portion of the first sequencing primer and is nested with respect to the first tail primer.

2. A method of determining the nucleotide sequence contiguous to a known target nucleotide sequence, the method comprising;
   (a) contacting a target nucleic acid molecule comprising the known target nucleotide sequence with a population of tailed random primers under hybridization conditions;
   (b) performing a template-dependent extension reaction that is primed by a hybridized tailed random primer and that uses the portion of the target nucleic acid molecule downstream of the site of hybridization as a template;
   (c) contacting the product of step (b) with an initial target-specific primer under hybridization conditions;
   (d) performing a template-dependent extension reaction that is primed by a hybridized initial target-specific primer and that uses the target nucleic acid molecule as a template;
   (e) amplifying a portion of the target nucleic acid molecule and the tailed random primer sequence with a first tail primer and a first target-specific primer;
   (f) amplifying a portion of the amplicon resulting from step (e) with a second tail primer and a second target-specific primer;
   (g) sequencing the amplified portion from step (f) using a first and second sequencing primer;
wherein the population of tailed random primers comprises single-stranded oligonucleotide molecules having a 5' nucleic acid sequence identical to a first sequencing primer and a 3' nucleic acid sequence comprising from about 6 to about 12 random nucleotides;
wherein the first target-specific primer comprises a nucleic acid sequence that can specifically anneal to the known target nucleotide sequence of the target nucleic acid at the annealing temperature;
wherein the second target-specific primer comprises a 3' portion comprising a nucleic acid sequence that can specifically anneal to a portion of the known target nucleotide sequence comprised by the amplicon resulting from step (c), and a 5' portion comprising a nucleic acid sequence that is identical to a second sequencing primer and the second target-specific primer is nested with respect to the first target-specific primer;
wherein the first tail primer comprises a nucleic acid sequence identical to the tailed random primer; and
wherein the second tail primer comprises a nucleic acid sequence identical to a portion of the first sequencing primer and is nested with respect to the first tail primer.

3. The method of any of paragraphs 1-2, further comprising a step of contacting the sample and products with RNase after extension of the initial target-specific primer.

4. The method of any of paragraphs 1-3, wherein the tailed random primer can form a hair-pin loop structure.

5. The method of any of paragraphs 1-4, wherein the initial target-specific primer and the first target-specific primer are identical.

6. The method of any of paragraphs 1-5, wherein the tailed random primer further comprises a barcode portion comprising 6-12 random nucleotides between the 5' nucleic acid sequence identical to a first sequencing primer and the 3' nucleic acid sequence comprising 6-12 random nucleotides.

7. A method of determining the nucleotide sequence contiguous to a known target nucleotide sequence, the method comprising;
   (a) contacting a target nucleic acid molecule comprising the known target nucleotide sequence with a population of tailed random primers under hybridization conditions;
   (b) performing a template-dependent extension reaction that is primed by a hybridized tailed random primer and that uses the portion of the target nucleic acid molecule downstream of the site of hybridization as a template;
   (c) amplifying a portion of the target nucleic acid molecule and the tailed random primer sequence with a first tail primer and a first target-specific primer;
   (d) amplifying a portion of the amplicon resulting from step (c) with a second tail primer and a second target-specific primer;
   (e) sequencing the amplified portion from step (d) using a first and second sequencing primer;
wherein the population of tailed random primers comprises single-stranded oligonucleotide molecules having a 5' nucleic acid sequence identical to a first sequencing primer; a middle barcode portion comprising; and a 3' nucleic acid sequence comprising from about 6 to about 12 random nucleotides;
wherein the first target-specific primer comprises a nucleic acid sequence that can specifically anneal to the known target nucleotide sequence of the target nucleic acid at the annealing temperature;
wherein the second target-specific primer comprises a 3' portion comprising a nucleic acid sequence that can specifically anneal to a portion of the known target nucleotide sequence comprised by the amplicon resulting from step (c), and a 5' portion comprising a nucleic acid sequence that is identical to a second sequencing primer and the second target-specific primer is nested with respect to the first target-specific primer;
wherein the first tail primer comprises a nucleic acid sequence identical to the tailed random primer; and
wherein the second tail primer comprises a nucleic acid sequence identical to a portion of the first sequencing primer and is nested with respect to the first tail primer.

8. The method of paragraph 7, wherein the each tailed random primer further comprises a spacer nucleic acid sequence between the 5' nucleic acid sequence identical to a first sequencing primer and the 3' nucleic acid sequence comprising about 6 to about 12 random nucleotides.

9. The method of paragraph 7 or 8, wherein the unhybridized primers are removed from the reaction after an extension step.
10. The method of any of paragraphs 7-9, wherein the second tail primer is nested with respect to the first tail primer by at least 3 nucleotides.
11. The method of any of paragraphs 7-10, wherein the first target-specific primer further comprises a 5' tag sequence portion comprising a nucleic acid sequence of high GC content which is not substantially complementary to or substantially identical to any other portion of any of the primers.
12. The method of any of paragraphs 7-11, wherein the second tail primer is identical to the full-length first sequencing primer.
13. The method of any of paragraphs 7-12, wherein the portions of the target-specific primers that specifically anneal to the known target will anneal specifically at a temperature of about 65° C. in a PCR buffer.
14. The method of any of paragraphs 7-13, wherein the sample comprises genomic DNA.
15. The method of any of paragraphs 7-14, wherein the sample comprises RNA and the method further comprises a first step of subjecting the sample to a reverse transcriptase regimen.
16. The method of any of paragraphs 7-15, wherein the nucleic acids present in the sample have not been subjected to shearing or digestion.
17. The method of any of paragraphs 7-16, wherein the sample comprises single-stranded gDNA or cDNA. 18. The method of any of paragraphs 7-17, wherein the reverse transcriptase regimen comprises the use of random hexamers.
19. The method of any of paragraphs 7-18, wherein a gene rearrangement comprises the known target sequence.
20. The method of paragraph 19, wherein the gene rearrangement is present in a nucleic acid selected from the group consisting of: genomic DNA; RNA; and cDNA.
21. The method of any of paragraphs 19-20, wherein the gene rearrangement comprises an oncogene.
22. The method of paragraph 21, wherein the gene rearrangement comprises a fusion oncogene.
23. The method of any of paragraphs 7-22, wherein the nucleic acid product is sequenced by a next-generation sequencing method.
24. The method of paragraph 23, wherein the next-generation sequencing method comprises a method selected from the group consisting of:
Ion Torrent, Illumina, SOLiD, 454; Massively Parallel Signature Sequencing solid-phase, reversible dye-terminator sequencing; and DNA nanoball sequencing.
25. The method of any of paragraphs 7-24, wherein the first and second sequencing primers are compatible with the selected next-generation sequencing method.
26. The method of any of paragraphs 7-25, wherein the method comprises contacting the sample, or separate portions of the sample, with a plurality of sets of first and second target-specific primers.
27. The method of any of paragraphs 7-26, wherein the method comprises contacting a single reaction mixture comprising the sample with a plurality of sets of first and second target-specific primers.
28. The method of any of paragraphs 7-27, wherein the plurality of sets of first and second target-specific primers specifically anneal to known target nucleotide sequences comprised by separate genes.
29. The method of any of paragraphs 7-28, wherein at least two sets of first and second target-specific primers specifically anneal to different portions of a known target nucleotide sequence.
30. The method of any of paragraphs 7-29, wherein at least two sets of first and second target-specific primers specifically anneal to different portions of a single gene comprising a known target nucleotide sequence.
31. The method of any of paragraphs 7-30, wherein at least two sets of first and second target-specific primers specifically anneal to different exons of a gene comprising a known nucleotide target sequence.
32. The method of any of paragraphs 7-31, wherein the plurality of first target-specific primers comprise identical 5' tag sequence portions.
33. The method of any of paragraphs 7-32, wherein each tailed random primer in a population of tailed random primers further comprises an identical sample barcoding portion.
34. The method of paragraph 33, wherein multiple samples are each contacted with a separate population of tailed random primers with a sample barcoding portion; wherein each population of tailed random primers has a distinct sample barcoding portion; and wherein the samples are pooled after step (b).
35. The method of any of paragraphs 7-34, wherein each amplification step comprises a set of cycles of a PCR amplification regimen from 5 cycles to 20 cycles in length.
36. The method of any of paragraphs 7-35, wherein the target-specific primers and the tail primers are designed such that they will specifically anneal to their complementary sequences at an annealing temperature of from about 61 to 72° C.
37. The method of any of paragraphs 7-36, wherein the target-specific primers and the tail primers are designed such that they will specifically anneal to their complementary sequences at an annealing temperature of about 65° C.
38. The method of any of paragraphs 7-37, wherein the target nucleic acid molecule is from a sample, optionally which is a biological sample obtained from a subject.
39. The method of paragraph 38, wherein the sample is obtained from a subject in need of treatment for a disease associated with a genetic alteration.
40. The method of paragraph 39, wherein the disease is cancer.
41. The method of paragraph 38, wherein the sample comprises a population of tumor cells.
42. The method of paragraph 38, wherein the sample is a tumor biopsy.
43. The method paragraph 40, wherein the cancer is lung cancer.
44. The method of any of paragraphs 7-43, wherein a disease-associated gene comprises the known target sequence.
45. The method of 38, wherein a gene rearrangement product in the sample comprises the known target sequence.
46. The method of paragraph 45, wherein the gene rearrangement product is an oncogene.
47. A method of preparing nucleic acids for analysis, the method comprising:
(a) contacting a nucleic acid template comprising a first strand of a target nucleic acid with a complementary target-specific primer that comprises a target-specific hybridization sequence, under conditions to promote template-specific hybridization and extension of the target-specific primer; and
    (b) contacting a nucleic acid template comprising a second strand that is complementary to the first strand of the target nucleic acid with a plurality of different primers that share a common sequence that is 5' to different hybridization sequences, under conditions to promote template-specific hybridization and extension of at least one of the plurality of different primers,
  wherein an extension product is generated to contain both a sequence that is characteristic of the target-specific primer and a sequence that is characteristic of the at least one of the plurality of different primers.
48. The method of paragraph 47, wherein the target nucleic acid is a ribonucleic acid.
49. The method of paragraph 47, wherein the target nucleic acid is a deoxyribonucleic acid.
50. The method of any of paragraphs 47 to 49 wherein steps (a) and (b) are performed sequentially.
51. The method of any of paragraphs 47 to 50, wherein the nucleic acid template in step (a) comprises an extension product resulting from the hybridization and extension of the at least one of the plurality of different primers in step (b).
52. The method of any one of paragraphs 47 to 50, wherein the nucleic acid template in step (b) comprises an extension product resulting from the hybridization and extension of the target-specific primer in step (a).
53. The method of paragraph 48, wherein the target nucleic acid is a messenger RNA encoded from a chromosomal segment that comprises a genetic rearrangement.
54. The method of paragraph 49, wherein the target nucleic acid is a chromosomal segment that comprises a portion of a genetic rearrangement.
55. The method of paragraph 8, wherein the genetic rearrangement is an inversion, deletion, or translocation.
56. The method of any one of paragraphs 47 to 55 further comprising amplifying the extension product.
57. The method of any one of paragraphs 47 to 55 further comprising contacting the extension product or amplified extension product with an immobilized oligonucleotide under conditions in which hybridization occurs between the extension product and immobilized oligonucleotide.
58. The method of any preceding paragraph wherein the target nucleic acid comprises a target portion having a known sequence and a flanking portion having an unknown sequence.
59. The method of paragraph 58, wherein different hybridization sequences are complementary to the flanking portion.
60. The method of paragraph 58 or 59, wherein the target-specific hybridization sequence is complementary to the target portion.
61. The method of any of paragraphs 47 to 60, wherein the target-specific primer further comprises, 5' to the target-specific hybridization sequence, at least one of an index sequence, a barcode sequence and an adaptor sequence.
62. The method of any of paragraphs 47 to 60, wherein the common sequence comprises at least one of an index sequence, barcode sequence and an adaptor sequence.
63. The method of any of paragraphs 1-62, wherein the adaptor sequence is a cleavable adaptor sequence for immobilizing oligonucleotides in a flow cell.

Some embodiments of the technology described herein can be defined according to any of the following numbered paragraphs:

1. A method of preparing nucleic acids for analysis, the method comprising:
    (a) contacting a nucleic acid template comprising a first strand of a target nucleic acid with a complementary target-specific primer that comprises a target-specific hybridization sequence, under conditions to promote template-specific hybridization and extension of the target-specific primer; and
    (b) contacting a nucleic acid template comprising a second strand that is complementary to the first strand of the target nucleic acid with a plurality of different primers that share a common sequence that is 5' to different hybridization sequences, under conditions to promote template-specific hybridization and extension of at least one of the plurality of different primers,
  wherein an extension product is generated to contain both a sequence that is characteristic of the target-specific primer and a sequence that is characteristic of the at least one of the plurality of different primers.
2. The method of paragraph 1, wherein the target nucleic acid is a ribonucleic acid.
3. The method of paragraph 1, wherein the target nucleic acid is a deoxyribonucleic acid.
4. The method of any of paragraphs 1 to 3 wherein steps (a) and (b) are performed sequentially.
5. The method of any of paragraphs 1 to 4, wherein the nucleic acid template in step (a) comprises an extension product resulting from the hybridization and extension of the at least one of the plurality of different primers in step (b).
6. The method of any one of paragraphs 1 to 4, wherein the nucleic acid template in step (b) comprises an extension product resulting from the hybridization and extension of the target-specific primer in step (a).
7. The method of paragraph 2, wherein the target nucleic acid is a messenger RNA encoded from a chromosomal segment that comprises a genetic rearrangement.
8. The method of paragraph 3, wherein the target nucleic acid is a chromosomal segment that comprises a portion of a genetic rearrangement.
9. The method of paragraph 8, wherein the genetic rearrangement is an inversion, deletion, or translocation.
10. The method of any one of paragraphs 1 to 9 further comprising amplifying the extension product.
11. The method of any one of paragraphs 1 to 9 further comprising contacting the extension product or amplified extension product with an immobilized oligonucleotide under conditions in which hybridization occurs between the extension product and immobilized oligonucleotide.
12. The method of any preceding paragraph wherein the target nucleic acid comprises a target portion having a known sequence and a flanking portion having an unknown sequence.
13. The method of paragraph 12, wherein different hybridization sequences are complementary to the flanking portion.
14. The method of paragraph 12 or 13, wherein the target-specific hybridization sequence is complementary to the target portion.

15. The method of any of paragraphs 1 to 14, wherein the target-specific primer further comprises, 5' to the target-specific hybridization sequence, at least one of an index sequence, a barcode sequence and an adaptor sequence.
16. The method of any of paragraphs 1 to 14, wherein the common sequence comprises at least one of an index sequence, barcode sequence and an adaptor sequence.
17. The method of paragraph 15 or 16, wherein the adaptor sequence is a cleavable adaptor sequence for immobilizing oligonucleotides in a flow cell.
18. A method of determining the nucleotide sequence contiguous to a known target nucleotide sequence, the method comprising;
    (a) contacting a target nucleic acid molecule comprising the known target nucleotide sequence with an initial target-specific primer under hybridization conditions;
    (b) performing a template-dependent extension reaction that is primed by a hybridized initial target-specific primer and that uses the target nucleic acid molecule as a template;
    (c) contacting the product of step (b) with a population of tailed random primers under hybridization conditions;
    (d) performing a template-dependent extension reaction that is primed by a hybridized tailed random primer and that uses the portion of the target nucleic acid molecule downstream of the site of hybridization as a template;
    (e) amplifying a portion of the target nucleic acid molecule and the tailed random primer sequence with a first tail primer and a first target-specific primer;
    (f) amplifying a portion of the amplicon resulting from step (e) with a second tail primer and a second target-specific primer;
    (g) sequencing the amplified portion from step (f) using a first and second sequencing primer;
    wherein the population of tailed random primers comprises single-stranded oligonucleotide molecules having a 5' nucleic acid sequence identical to a first sequencing primer and a 3' nucleic acid sequence comprising from about 6 to about 12 random nucleotides;
    wherein the first target-specific primer comprises a nucleic acid sequence that can specifically anneal to the known target nucleotide sequence of the target nucleic acid at the annealing temperature;
    wherein the second target-specific primer comprises a 3' portion comprising a nucleic acid sequence that can specifically anneal to a portion of the known target nucleotide sequence comprised by the amplicon resulting from step (e), and a 5' portion comprising a nucleic acid sequence that is identical to a second sequencing primer and the second target-specific primer is nested with respect to the first target-specific primer;
    wherein the first tail primer comprises a nucleic acid sequence identical to the tailed random primer; and
    wherein the second tail primer comprises a nucleic acid sequence identical to a portion of the first sequencing primer and is nested with respect to the first tail primer.
19. A method of determining the nucleotide sequence contiguous to a known target nucleotide sequence, the method comprising;
    (a) contacting a target nucleic acid molecule comprising the known target nucleotide sequence with a population of tailed random primers under hybridization conditions;
    (b) performing a template-dependent extension reaction that is primed by a hybridized tailed random primer and that uses the portion of the target nucleic acid molecule downstream of the site of hybridization as a template;
    (c) contacting the product of step (b) with an initial target-specific primer under hybridization conditions;
    (d) performing a template-dependent extension reaction that is primed by a hybridized initial target-specific primer and that uses the target nucleic acid molecule as a template;
    (e) amplifying a portion of the target nucleic acid molecule and the tailed random primer sequence with a first tail primer and a first target-specific primer;
    (f) amplifying a portion of the amplicon resulting from step (e) with a second tail primer and a second target-specific primer;
    (g) sequencing the amplified portion from step (f) using a first and second sequencing primer;
    wherein the population of tailed random primers comprises single-stranded oligonucleotide molecules having a 5' nucleic acid sequence identical to a first sequencing primer and a 3' nucleic acid sequence comprising from about 6 to about 12 random nucleotides;
    wherein the first target-specific primer comprises a nucleic acid sequence that can specifically anneal to the known target nucleotide sequence of the target nucleic acid at the annealing temperature;
    wherein the second target-specific primer comprises a 3' portion comprising a nucleic acid sequence that can specifically anneal to a portion of the known target nucleotide sequence comprised by the amplicon resulting from step (c), and a 5' portion comprising a nucleic acid sequence that is identical to a second sequencing primer and the second target-specific primer is nested with respect to the first target-specific primer;
    wherein the first tail primer comprises a nucleic acid sequence identical to the tailed random primer; and
    wherein the second tail primer comprises a nucleic acid sequence identical to a portion of the first sequencing primer and is nested with respect to the first tail primer.
20. The method of any of paragraphs 18-19, further comprising a step of contacting the sample and products with RNase after extension of the initial target-specific primer.
21. The method of any of paragraphs 1-3, wherein the tailed random primer can form a hair-pin loop structure.
22. The method of any of paragraphs 1-4, wherein the initial target-specific primer and the first target-specific primer are identical.
23. The method of any of paragraphs 1-5, wherein the tailed random primer further comprises a barcode portion comprising 6-12 random nucleotides between the 5' nucleic acid sequence identical to a first sequencing primer and the 3' nucleic acid sequence comprising 6-12 random nucleotides. 7. A method of determining the nucleotide sequence contiguous to a known target nucleotide sequence, the method comprising;

(a) contacting a target nucleic acid molecule comprising the known target nucleotide sequence with a population of tailed random primers under hybridization conditions;

(b) performing a template-dependent extension reaction that is primed by a hybridized tailed random primer and that uses the portion of the target nucleic acid molecule downstream of the site of hybridization as a template;

(c) amplifying a portion of the target nucleic acid molecule and the tailed random primer sequence with a first tail primer and a first target-specific primer;

(d) amplifying a portion of the amplicon resulting from step (c) with a second tail primer and a second target-specific primer;

(e) sequencing the amplified portion from step (d) using a first and second sequencing primer;

wherein the population of tailed random primers comprises single-stranded oligonucleotide molecules having a 5' nucleic acid sequence identical to a first sequencing primer; a middle barcode portion comprising; and a 3' nucleic acid sequence comprising from about 6 to about 12 random nucleotides;

wherein the first target-specific primer comprises a nucleic acid sequence that can specifically anneal to the known target nucleotide sequence of the target nucleic acid at the annealing temperature;

wherein the second target-specific primer comprises a 3' portion comprising a nucleic acid sequence that can specifically anneal to a portion of the known target nucleotide sequence comprised by the amplicon resulting from step (c), and a 5' portion comprising a nucleic acid sequence that is identical to a second sequencing primer and the second target-specific primer is nested with respect to the first target-specific primer;

wherein the first tail primer comprises a nucleic acid sequence identical to the tailed random primer; and wherein the second tail primer comprises a nucleic acid sequence identical to a portion of the first sequencing primer and is nested with respect to the first tail primer.

24. The method of paragraph 23, wherein the each tailed random primer further comprises a spacer nucleic acid sequence between the 5' nucleic acid sequence identical to a first sequencing primer and the 3' nucleic acid sequence comprising about 6 to about 12 random nucleotides.

25. The method of paragraph 23 or 24, wherein the unhybridized primers are removed from the reaction after an extension step.

26. The method of any of paragraphs 23-25, wherein the second tail primer is nested with respect to the first tail primer by at least 3 nucleotides.

27. The method of any of paragraphs 23-26, wherein the first target-specific primer further comprises a 5' tag sequence portion comprising a nucleic acid sequence of high GC content which is not substantially complementary to or substantially identical to any other portion of any of the primers.

28. The method of any of paragraphs 23-27, wherein the second tail primer is identical to the full-length first sequencing primer.

29. The method of any of paragraphs 23-28, wherein the portions of the target-specific primers that specifically anneal to the known target will anneal specifically at a temperature of about 65° C. in a PCR buffer.

30. The method of any of paragraphs 23-29, wherein the sample comprises genomic DNA.

31. The method of any of paragraphs 23-30, wherein the sample comprises RNA and the method further comprises a first step of subjecting the sample to a reverse transcriptase regimen.

32. The method of any of paragraphs 23-31, wherein the nucleic acids present in the sample have not been subjected to shearing or digestion or wherein the sample comprises single-stranded gDNA or cDNA.

33. The method of any of paragraphs 23-32, wherein the reverse transcriptase regimen comprises the use of random hexamers.

34. The method of any of paragraphs 23-33, wherein a gene rearrangement comprises the known target sequence.

35. The method of paragraph 34, wherein the gene rearrangement is present in a nucleic acid selected from the group consisting of: genomic DNA; RNA; and cDNA.

36. The method of any of paragraphs 34-35, wherein the gene rearrangement comprises an oncogene.

37. The method of paragraph 36, wherein the gene rearrangement comprises a fusion oncogene.

38. The method of any of paragraphs 23-37, wherein the nucleic acid product is sequenced by a next-generation sequencing method.

39. The method of paragraph 38, wherein the next-generation sequencing method comprises a method selected from the group consisting of:

Ion Torrent, Illumina, SOLiD, 454; Massively Parallel Signature Sequencing solid-phase, reversible dye-terminator sequencing; and DNA nanoball sequencing.

40. The method of any of paragraphs 23-39, wherein the first and second sequencing primers are compatible with the selected next-generation sequencing method.

41. The method of any of paragraphs 23-40, wherein the method comprises contacting the sample, or separate portions of the sample, with a plurality of sets of first and second target-specific primers.

42. The method of any of paragraphs 23-41, wherein the method comprises contacting a single reaction mixture comprising the sample with a plurality of sets of first and second target-specific primers.

43. The method of any of paragraphs 23-42, wherein the plurality of sets of first and second target-specific primers specifically anneal to known target nucleotide sequences comprised by separate genes.

44. The method of any of paragraphs 23-43, wherein at least two sets of first and second target-specific primers specifically anneal to different portions of a known target nucleotide sequence.

45. The method of any of paragraphs 23-44, wherein at least two sets of first and second target-specific primers specifically anneal to different portions of a single gene comprising a known target nucleotide sequence.

46. The method of any of paragraphs 23-45, wherein at least two sets of first and second target-specific primers specifically anneal to different exons of a gene comprising a known nucleotide target sequence.

47. The method of any of paragraphs 23-46, wherein the plurality of first target-specific primers comprise identical 5' tag sequence portions.

48. The method of any of paragraphs 23-47, wherein each tailed random primer in a population of tailed random primers further comprises an identical sample barcoding portion.

49. The method of paragraph 48, wherein multiple samples are each contacted with a separate population of tailed random primers with a sample barcoding portion; wherein each population of tailed random primers has a distinct sample barcoding portion; and wherein the samples are pooled after step (b).
50. The method of any of paragraphs 23-49, wherein each amplification step comprises a set of cycles of a PCR amplification regimen from 5 cycles to 20 cycles in length.
51. The method of any of paragraphs 23-50, wherein the target-specific primers and the tail primers are designed such that they will specifically anneal to their complementary sequences at an annealing temperature of from about 61 to 72° C.
52. The method of any of paragraphs 23-51, wherein the target-specific primers and the tail primers are designed such that they will specifically anneal to their complementary sequences at an annealing temperature of about 65° C.
53. The method of any of paragraphs 23-52, wherein the target nucleic acid molecule is from a sample, optionally which is a biological sample obtained from a subject.
54. The method of paragraph 53, wherein the sample is obtained from a subject in need of treatment for a disease associated with a genetic alteration.
55. The method of paragraph 54, wherein the disease is cancer.
56. The method of paragraph 53, wherein the sample comprises a population of tumor cells.
57. The method of paragraph 53, wherein the sample is a tumor biopsy.
58. The method paragraph 55, wherein the cancer is lung cancer.
59. The method of any of paragraphs 23-58, wherein a disease-associated gene comprises the known target sequence.
60. The method of 53, wherein a gene rearrangement product in the sample comprises the known target sequence.
61. The method of paragraph 60, wherein the gene rearrangement product is an oncogene.

EXAMPLES

Example 1: A Method Using Reverse Transcriptase with Tailed Random Oligonucleotides and Gene-Specific Oligonucleotides to Amplify 3'Fusion Events First Strand Synthesis As a first step towards amplifying 3' fusion events for sequence analysis, RNA was obtained from a sample isolated from a subject. The following reaction was assembled on ice to synthesize the first cDNA strand:
12 μL purified RNA and H2O
2 μL 1.2 μg/μL random primer #1 (9mer)
2 μL dNTP
The reaction was transferred to a thermocycler and incubated at 65° C. for 5 minutes. Then, the reaction was centrifuged and incubated on ice for at least one minute.
To the reaction above, the following was prepared on ice:
2 μL 10× M-MuLV reverse transcriptase buffer
1 μL 40 U/μL RNase inhibitor
1 μL 200 U/μL M-MuLV enzyme
The reaction was mixed and centrifuged briefly to collect the reaction contents at the bottom of the tube, then placed back on ice. The reaction was then incubated at 42° C. for 60 minutes, followed by 4° C.

ExoI Treatment

The following was added to the reaction above,
1 μL 20 U/μL Exonuclease I
The reaction was mixed and centrifuged briefly to collect the contents at the bottom of the tube, then incubated at 37° C. for 10 minutes. Next, 1.28 μL of 1N NaOH was added and mixed by pipetting up and down then centrifuged to collect the contents. The reaction was incubated at 80° C. for 10 minutes, then 4 μL 10 mM Tris pH 8.3 was added ad mixed by pipetting up and down. 20 μL of the Exonuclease-treated DNA solution was transferred to a fresh 200 μL PCR tube on ice.

Second Strand cDNA Synthesis

The following reaction was prepared:
20 μL DNA solution, from above
11 μL nuclease-free $H_2O$
4 μL 10×PCR Buffer II
4 μL 3 μM gene-specific primer #1
1 μL 0.5 mM dNTP
The reaction was mixed by pipetting up and down then centrifuged briefly to collect the contents and placed on ice. The reaction was then incubated at 95° C. for 3 minutes, then 22° C. for 10 seconds followed by 4° C. until proceeding to the next step. The reaction was incubated on ice for at least one minutes.
The following was added to the reaction:
1 μL 400 U/μL Manta 1.0 DNA Polymerase (high concentration)
The reaction was incubated at 25° C. for 10 seconds, then 70° C. for 10 minutes and maintained at 4° C. until proceeding to the next step.

DNA Purification with AMPure Beads #1

The following was added to the reaction above,
88.4 μL AMPure beads
The suspension was mixed well and incubated for 5 minutes at room temperature. A magnet was used 2-4 minutes to collect the beads and the solution appeared clear. The supernatant was discarded and the beads were washed twice times with 200 μL 70% ethanol on the magnet. After the second wash, the beads were dried at room temperature for 5 minutes. Finally, the DNA was eluted by removing the tubes from the magnet and resuspending the beads in 12 μL 10 mM Tris-HCl pH 8.3 elution buffer included in the AMPure kit. The RNA-bead solution was placed on the magnet for 2 minutes. Then, the DNA solution was transferred to a fresh PCR tube, being sure to avoid transferring beads to the fresh tube.

It should be appreciated that in some embodiments the ratio of beads to reaction mix can effect the size of fragments returned. In some embodiments, for fusion detection, all or substantially all fragments are longer than 60 nt (e.g., 30 nt on either side of a fusion break point or junction) so each gene can be easily identified.

Amplification #1

The following reaction was prepared:
10 μL purified DNA, from Purification #1 above
4 μL 5×Phoenix Hot Start Buffer
2 μL 2 mM dNTP
2 μL 10 μM P5_barcode primer
2 μL 3 μM gene-specific primer #1
0.5 to 2 Units polymerase (e.g., Pheonix Hot Start Taq, VeraSeq)

The reaction was incubated as follows:
Step 1: 95° C. for 3 minutes
Step 2: 95° C. for 30 seconds
Step 3: 65° C. for 5 minutes, return to step 2 for 14 cycles
Step 4: 72° C. for 2 minutes
Step 5: 4° C., until proceeding with the protocol
DNA Purification with AMPure Beads #2
The following was added to the reaction above,
36.4 µL AMPure beads The suspension was mixed well and incubated for 5 minutes at room temperature. A magnet was used 2-4 minutes to collect the beads and the solution appeared clear. The supernatant was discarded and the beads were washed twice times with 200 µL 70% ethanol on the magnet. After the second wash, the beads were dried at room temperature for 5 minutes. Finally, the DNA was eluted by removing the tubes from the magnet and resuspending the beads in 9 µL 10 mM Tris-HCl pH 8.3 elution buffer included in the AMPure kit. The RNA-bead solution was placed on the magnet for 2 minutes. Then, the DNA solution was transferred to a fresh PCR tube, being sure to avoid transferring beads to the fresh tube.

Amplification #2
The following reaction was prepared:
8.5 µL purified DNA, from Purification #2 above
4 µL 5×Phoenix Hot Start Buffer
2 µL 2 mM dNTP
2 µL 10 µM P5_29 bp primer
2 µL 10 µM P7 barcode primer
2 µL 3 µM gene-specific primer #2
0.2 µL 5 U/µL Phoenix Hot Start Taq polymerase
2 µL 10 µM P7 barcode primer The reaction was incubated as follows:
Step 1: 95° C. for 3 minutes
Step 2: 95° C. for 30 seconds
Step 3: 65° C. for 5 minutes, return to step 2 for 14 cycles
Step 4: 72° C. for 2 minutes
Step 5: 4° C., until proceeding with the protocol
DNA Purification with AMPure Beads #3
The following was added to the reaction above,
37.3 µL AMPure beads The suspension was mixed well and incubated for 5 minutes at room temperature. A magnet was used 2-4 minutes to collect the beads and the solution appeared clear. The supernatant was discarded and the beads were washed twice times with 200 µL 70% ethanol on the magnet. After the second wash, the beads were dried at room temperature for 5 minutes. Finally, the DNA was eluted by removing the tubes from the magnet and resuspending the beads in 20 µL 10 mM Tris-HCl pH 8.3 elution buffer included in the AMPure kit. The RNA-bead solution was placed on the magnet for 2 minutes. Then, the DNA solution was transferred to a fresh PCR tube, being sure to avoid transferring beads to the fresh tube.

Quantification of Library Concentration
The Kapa Biosystems qPCR kit for Illumina was used to quantitate the concentration of each library prepared using the protocol above. The barcoded libraries were pooled at equimolar concentrations. Then the library was loaded on an Illumina MiSeq at XpM using the MiSeq v2 300 cycle reagent kit following the manufacturer's instruction. The samples were sequenced using 2×150 bp reads with 7 base encoded index reads.

Example 2: A Method Using Reverse Transcriptase with Gene-Specific Oligonucleotides and Tailed Random Oligonucleotides to Amplify 5'Fusion Events First Strand Synthesis
As a first step towards amplifying 5' fusion events for sequence analysis, RNA was obtained from a sample isolated from a subject. The following reaction was assembled on ice to synthesize the first cDNA strand:
12 µL purified RNA and H$_2$O
2 µL gene-specific primer #1
2 µL dNTP The reaction was transferred to a thermocycler and incubated at 65° C. for 5 minutes. Then, the reaction was centrifuged and incubated on ice for at least one minute.

To the reaction above, the following was prepared on ice:
2 µL 10×M-MuLV reverse transcriptase buffer
1 µL 40 U/µL RNase inhibitor
1 µL 200 U/µL M-MuLV enzyme The reaction was mixed and centrifuged briefly to collect the reaction contents at the bottom of the tube, then placed back on ice. The reaction was then incubated at 42° C. for 60 minutes, followed by 4° C.

ExoI Treatment
The following was added to the reaction above,
1 µL 20 U/µL Exonuclease I The reaction was mixed and centrifuged briefly to collect the contents at the bottom of the tube, then incubated at 37° C. for 10 minutes. Next, 1.28 µL of 1N NaOH was added and mixed by pipetting up and down then centrifuged to collect the contents. The reaction was incubated at 80° C. for 10 minutes, then 4 µL 10 mM Tris pH 8.3 was added ad mixed by pipetting up and down. 20 µL of the Exonuclease-treated DNA solution was transferred to a fresh 200 µL PCR tube on ice.

Second Strand cDNA Synthesis
The following reaction was prepared:
20 µL DNA solution, from above
11 µL nuclease-free H$_2$O
4 µL 10×PCR Buffer II
4 µL 1.2 µg/µL random primer (9mer)
1 µL 0.5 mM dNTP The reaction was mixed by pipetting up and down then centrifuged briefly to collect the contents and placed on ice. The reaction was then incubated at 95° C. for 3 minutes, then 22° C. for 10 seconds followed by 4° C. until proceeding to the next step. The reaction was incubated on ice for at least one minutes.

The following was added to the reaction:
1 µL 400 U/µL Manta 1.0 DNA Polymerase (high concentration)

The reaction was incubated at 25° C. for 10 seconds, then 70° C. for 10 minutes and maintained at 4° C. until proceeding to the next step.

DNA Purification with AMPure Beads #1
The following was added to the reaction above,
88.4 µL AMPure beads The suspension was mixed well and incubated for 5 minutes at room temperature. A magnet was used 2-4 minutes to collect the beads and the solution appeared clear. The supernatant was discarded and the beads were washed twice times with 200 µL 70% ethanol on the magnet. After the second wash, the beads were dried at room temperature for 5 minutes. Finally, the DNA was eluted by removing the tubes from the magnet and resuspending the beads in 12 µL 10 mM Tris-HCl pH 8.3 elution buffer included in the AMPure kit. The RNA-bead solution was placed on the magnet for 2 minutes. Then, the DNA solution was transferred to a fresh PCR tube, being sure to avoid transferring beads to the fresh tube.

Amplification #1
The following reaction was prepared:
10 µL purified DNA, from Purification #1 above
4 µL 5× Phoenix Hot Start Buffer
2 µL 2 mM dNTP
2 µL 10 µM P5_barcode primer
2 µL 3 µM gene-specific primer #1
0.5 to 2 Units polymerase (e.g., Pheonix Hot Start Taq, VeraSeq)
The reaction was incubated as follows:
Step 1: 95° C. for 3 minutes
Step 2: 95° C. for 30 seconds
Step 3: 65° C. for 5 minutes, return to step 2 for 14 cycles
Step 4: 72° C. for 2 minutes
Step 5: 4° C., until proceeding with the protocol
DNA Purification with AMPure beads #2
The following was added to the reaction above,
36.4 µL AMPure beads
The suspension was mixed well and incubated for 5 minutes at room temperature. A magnet was used 2-4 minutes to collect the beads and the solution appeared clear. The supernatant was discarded and the beads were washed twice times with 200 µL 70% ethanol on the magnet. After the second wash, the beads were dried at room temperature for 5 minutes. Finally, the DNA was eluted by removing the tubes from the magnet and resuspending the beads in 9 µL 10 mM Tris-HCl pH 8.3 elution buffer included in the AMPure kit. The RNA-bead solution was placed on the magnet for 2 minutes. Then, the DNA solution was transferred to a fresh PCR tube, being sure to avoid transferring beads to the fresh tube.

Amplification #2
The following reaction was prepared:
8.5 µL purified DNA, from Purification #2 above
4 µL 5× Phoenix Hot Start Buffer
2 µL 2 mM dNTP
2 µL 10 µM P5_29 bp primer
2 µL 10 µM P7 barcode primer
2 µL 3 µM gene-specific primer #2
0.2 µL 5 U/µL Phoenix Hot Start Taq polymerase
2 µL 10 µM P7 barcode primer
The reaction was incubated as follows:
Step 1: 95° C. for 3 minutes
Step 2: 95° C. for 30 seconds
Step 3: 65° C. for 5 minutes, return to step 2 for 14 cycles
Step 4: 72° C. for 2 minutes
Step 5: 4° C., until proceeding with the protocol
DNA Purification with AMPure Beads #3
The following was added to the reaction above,
37.3 µL AMPure beads
The suspension was mixed well and incubated for 5 minutes at room temperature. A magnet was used 2-4 minutes to collect the beads and the solution appeared clear. The supernatant was discarded and the beads were washed twice times with 200 µL 70% ethanol on the magnet. After the second wash, the beads were dried at room temperature for 5 minutes. Finally, the DNA was eluted by removing the tubes from the magnet and resuspending the beads in 20 µL 10 mM Tris-HCl pH 8.3 elution buffer included in the AMPure kit. The RNA-bead solution was placed on the magnet for 2 minutes. Then, the DNA solution was transferred to a fresh PCR tube, being sure to avoid transferring beads to the fresh tube.

Quantification of Library Concentration

The Kapa Biosystems qPCR kit for Illumina was used to quantitate the concentration of each library prepared using the protocol above. The barcoded libraries were pooled at equimolar concentrations. Then the library was loaded on an Illumina MiSeq at XpM using the MiSeq v2 300 cycle reagent kit following the manufacturer's instruction. The samples were sequenced using 2×150 bp reads with 7 base encoded index reads.

What is claimed herein is:

1. A method of preparing nucleic acids for analysis, the method comprising:
   (a) contacting a first nucleic acid template comprising a sequence of a first strand of a double-stranded target nucleic acid with a complementary target-specific primer that comprises a target-specific hybridization sequence, under conditions to promote template-specific hybridization and extension of the target-specific primer;
   (b) contacting a second nucleic acid template comprising a sequence of a second strand that is complementary to the sequence of the first strand of the double-stranded target nucleic acid with a plurality of different primers that share a common sequence that is 5' to different hybridization sequences, under conditions to promote template-specific hybridization and extension of at least one of the plurality of different primers, wherein the different hybridization sequences have different 3' ends, and wherein each primer of the plurality of different primers does not anneal to the same sequence of the double-stranded target nucleic acid as any other primer of the plurality of different primers,
   wherein, following (a) and (b), an extension product is generated to contain both a sequence that is characteristic of the target-specific primer and a sequence that is characteristic of the at least one of the plurality of different primers; and
   (c) subjecting the extension product to an amplification reaction comprising successive rounds of polymerase extension of i) a tail primer that comprises a 3' sequence that specifically anneals to the complement of the common sequence and that comprises a 5' tail sequence, and ii) a primer that specifically anneals to the complement of the target-specific hybridization sequence.

2. The method of claim 1, wherein the first strand or the second strand of the double-stranded target nucleic acid is a ribonucleic acid.

3. The method of claim 1, wherein the first strand or the second strand of the double-stranded target nucleic acid is a deoxyribonucleic acid.

4. The method of claim 1, wherein steps (a) and (b) are performed sequentially.

5. The method of claim 1, wherein the first nucleic acid template comprises an extension product resulting from the hybridization and extension of the at least one of the plurality of different primers in step (b).

6. The method of claim 1, wherein the second nucleic acid template comprises an extension product resulting from the hybridization and extension of the target-specific primer in step (a).

7. The method of claim 2, wherein the ribonucleic acid is a messenger RNA encoded from a chromosomal segment that comprises a genetic rearrangement.

8. The method of claim 3, wherein the double-stranded target nucleic acid is a chromosomal segment that comprises a portion of a genetic rearrangement.

9. The method of claim 8, wherein the genetic rearrangement is an inversion, deletion, or translocation.

10. The method of claim 1, further comprising contacting the extension product or amplified extension product with an immobilized oligonucleotide under conditions in which hybridization occurs between the extension product and immobilized oligonucleotide.

11. The method of claim 1, wherein the double-stranded target nucleic acid comprises a target portion having a known sequence and a flanking portion having an unknown sequence.

12. The method of claim 11, wherein different hybridization sequences are complementary to the flanking portion.

13. The method of claim 11, wherein the target-specific hybridization sequence is complementary to the target portion.

14. The method of claim 1, wherein the target-specific primer further comprises, 5' to the target-specific hybridization sequence, at least one of an index sequence, a barcode sequence and an adaptor sequence.

15. The method of claim 1, wherein the common sequence comprises at least one of an index sequence, barcode sequence and an adaptor sequence.

16. The method of claim 14, wherein the adaptor sequence is a cleavable adaptor sequence for immobilizing oligonucleotides in a flow cell.

17. The method of claim 1, wherein the tail primer comprises a nucleic acid sequence identical to the common sequence.

18. The method of claim 1, wherein the 5' tail sequence comprises at least one of an index sequence, a barcode sequence, an adaptor sequence, and a sequencing primer hybridization sequence.

19. The method of claim 1, wherein the primer that specifically anneals to the complement of the target-specific hybridization sequence comprises a sequence identical to the target-specific primer.

20. The method of claim 1, wherein the primer that specifically anneals to the complement of the target-specific hybridization sequence comprises at least one modified internucleoside linkage.

21. The method of claim 1, wherein the target-specific primer comprises at least one modified internucleoside linkage.

22. The method of claim 1 further comprising purifying the extension product prior to (c).

23. The method of claim 1 further comprising purifying the amplified product of (c).

24. The method of claim 1, wherein the plurality of different primers can specifically anneal to sequences comprised by separate genes.

25. The method of claim 1, wherein the plurality of different primers can specifically anneal to different portions of the first strand or the second strand of the double-stranded target nucleic acid comprised by a single gene.

26. The method of claim 1, wherein the plurality of different primers can specifically anneal to different exons of a gene comprising the first strand or the second strand of the double-stranded target nucleic acid.

27. The method of claim 1, wherein the first strand or the second strand of the double-stranded target nucleic acid is derived from a biological sample.

28. The method of claim 27, wherein the first strand or the second strand of the double-stranded target nucleic acid is a cDNA produced from RNA in the biological sample.

29. The method of claim 1, wherein the double-stranded target nucleic acid is derived from a sample comprising nucleic acids that have been ligated to an oligonucleotide comprising a barcode sequence.

* * * * *

SEQUENCE LISTING

<160> NUMBER OF SEQ ID NOS: 5

<210> SEQ ID NO 1
<211> LENGTH: 7368
<212> TYPE: DNA
<213> ORGANISM: Homo sapiens

<400> SEQUENCE: 1

```
caagctttca agcattcaaa ggtctaaatg aaaaaggcta agtattattt caaaaggcaa      60
gtatatccta atatagcaaa acaaacaaag caaaatccat cagctactcc tccaattgaa     120
gtgatgaagc ccaaataatt catatagcaa aatggagaaa attagaccgg ccatctaaaa     180
atctgccatt ggtgaagtga tgaagaacat ttactgtctt attccgaagc ttgtcaattt     240
tgcaactctt ggctgcctat ggatttctgt ggtgcagtgt acagttttaa atagctgcct     300
aaagtcgtgt gtaactaatc tgggccagca gcttgacctt ggcacaccac ataatctgag     360
tgaaccgtgt atccaaggat gtcacttttg gaactctgta gatcagaaaa actgtgcttt     420
aaagtgtcgg gagtcgtgtg aggttggctg tagcagcgcg gaaggtgcat atgaagagga     480
agtactggaa aatgcagacc taccaactgc tccctttgct tcttccattg gaagccacaa     540
tatgacatta cgatggaaat ctgcaaactt ctctggagta aaatacatca ttcagtggaa     600
atatgcacaa cttctgggaa gctggactta tactaagact gtgtccagac cgtcctatgt     660
ggtcaagccc ctgcacccct tcactgagta cattttccga gtggtttgga tcttcacagc     720
```

```
gcagctgcag ctctactccc ctccaagtcc cagttacagg actcatcctc atggagttcc      780
tgaaactgca cctttgatta ggaatattga gagctcaagt cccgacactg tggaagtcag      840
ctgggatcca cctcaattcc caggtggacc tattttgggt tataacttaa ggctgatcag      900
caaaaatcaa aaattagatg cagggacaca gagaaccagt ttccagtttt actccacttt      960
accaaatact atctacaggt tttctattgc agcagtaaat gaagttggtg agggtccaga     1020
agcagaatct agtattacca cttcatcttc agcagttcaa caagaggaac agtggctctt     1080
tttatccaga aaaacttctc taagaaagag atctttaaaa catttagtag atgaagcaca     1140
ttgccttcgg ttggatgcta tataccataa tattacagga atatctgttg atgtccacca     1200
gcaaattgtt tatttctctg aaggaactct catatgggcg aagaaggctg ccaacatgtc     1260
tgatgtatct gacctgagaa ttttttacag aggttcagga ttaatttctt ctatctccat     1320
agattggctt tatcaaagaa tgtatttcat catggatgaa ctggtatgtg tctgtgattt     1380
agagaactgc tcaaacatcg aggaaattac tccaccctct attagtgcac ctcaaaaaat     1440
tgtggctgat tcatacaatg ggtatgtctt ttacctcctg agagatggca tttatagagc     1500
agaccttcct gtaccatctg ccggtgtgc agaagctgtg cgtattgtgg agagttgcac      1560
gttaaaggac tttgcaatca agccacaagc caagcgaatc atttacttca atgacactgc     1620
ccaagtcttc atgtcaacat ttctggatgg ctctgcttcc catctcatcc tacctcgcat     1680
cccctttgct gatgtgaaaa gttttgcttg tgaaaacaat gactttcttg tcacagatgg     1740
caaggtcatt ttccaacagg atgctttgtc ttttaatgaa ttcatcgtgg atgtgacct      1800
gagtcacata aagaatttg ggtttggtaa cttggtcatc tttggctcat cctcccagct     1860
gcaccctctg ccaggccgcc cgcaggagct ttcggtgctg tttggctctc accaggctct     1920
tgttcaatgg aagcctcctg cccttgccat aggagccaat gtcatcctga tcagtgatat     1980
tattgaactc tttgaattag gcccttctgc ctggcagaac tggacctatg aggtgaaagt     2040
atccacccaa gaccctcctg aagtcactca tattttcttg aacataagtg gaaccatgct     2100
gaatgtacct gagctgcaga gtgctatgaa atacaaggtt tctgtgagag caagttctcc     2160
aaagaggcca ggcccctggt cagagccctc agtgggtact accctggtgc cagctagtga     2220
accaccattt atcatggctg tgaaagaaga tgggctttgg agtaaaccat taaatagctt     2280
tggcccagga gagttcttat cctctgatat aggaaatgtg tcagacatgg attggtataa     2340
caacagcctc tactacagtg acacgaaagg cgacgttttt gtgtggctgc tgaatgggac     2400
ggatatctca gagaattatc acctacccag cattgcagga gcaggggctt tagcttttga     2460
gtggctgggt cactttctct actgggctgg aaagacatat gtgatacaaa ggcagtctgt     2520
gttgacggga cacacagaca ttgttaccca cgtgaagcta ttggtgaatg acatggtggt     2580
ggattcagtt ggtggatatc tctactggac cacactctat tcagtggaaa gcaccagact     2640
aaatggggaa agttcccttg tactacagac acagccttgg ttttctggga aaaggtaat      2700
tgctctaact ttagacctca gtgatgggct cctgtattgg ttggttcaag acagtcaatg     2760
tattcacctg tacacagctg ttcttcgggg acagagcact ggggatacca ccatcacaga     2820
atttgcagcc tggagtactt ctgaaatttc ccagaatgca ctgatgtact atagtggtcg     2880
gctgttctgg atcaatggct ttaggattat cacaactcaa gaaataggtc agaaaaccag     2940
tgtctctgtt ttggaaccag ccagatttaa tcagttcaca attattcaga catcccttaa     3000
gccctgcca gggaactttt cctttacccc taaggttatt ccagattctg ttcaagagtc      3060
```

```
ttcatttagg attgaaggaa atgcttcaag ttttcaaatc ctgtggaatg gtcccctgc    3120
ggtagactgg ggtgtagttt tctacagtgt agaatttagt gctcattcta agttcttggc    3180
tagtgaacaa cactctttac ctgtatttac tgtggaagga ctggaacctt atgccttatt    3240
taatctttct gtcactcctt atacctactg gggaaagggc cccaaaacat ctctgtcact    3300
tcgagcacct gaaacagttc catcagcacc agagaacccc agaatattta tattaccaag    3360
tggaaaatgc tgcaacaaga atgaagttgt ggtggaattt aggtgaaca aacctaagca    3420
tgaaaatggg gtgttaacaa aatttgaaat tttctacaat atatccaatc aaagtattac    3480
aaacaaaaca tgtgaagact ggattgctgt caatgtcact ccctcagtga tgtcttttca    3540
acttgaaggc atgagtccca gatgctttat tgccttccag gttagggcct ttacatctaa    3600
ggggccagga ccatatgctg acgttgtaaa gtctacaaca tcagaaatca acccatttcc    3660
tcacctcata actcttcttg gtaacaagat agttttttta gatatggatc aaaatcaagt    3720
tgtgtggacg ttttcagcag aaagagttat cagtgccgtt tgctacacag ctgataatga    3780
gatgggatat tatgctgaag gggactcact ctttcttctg cacttgcaca atcgctctag    3840
ctctgagctt ttccaagatt cactggtttt tgatatcaca gttattacaa ttgactggat    3900
ttcaaggcac ctctactttg cactgaaaga atcacaaaat ggaatgcaag tatttgatgt    3960
tgatcttgaa cacaaggtga aatatcccag agaggtgaag attcacaata ggaattcaac    4020
aataatttct ttttctgtat atcctctttt aagtcgcttg tattggacag aagtttccaa    4080
ttttggctac cagatgttct actacagtat tatcagtcac accttgcacc gaattctgca    4140
acccacagct acaaaccaac aaaacaaaag gaatcaatgt tcttgtaatg tgactgaatt    4200
tgagttaagt ggagcaatgg ctattgatac ctctaaccta gagaaaccat tgatatactt    4260
tgccaaagca caagagatct gggcaatgga tctggaaggc tgtcagtgtt ggagagttat    4320
cacagtacct gctatgctcg caggaaaaac ccttgttagc ttaactgtgg atggagatct    4380
tatatactgg atcatcacag caaaggacag cacacagatt tatcaggcaa agaaaggaaa    4440
tggggccatc gtttcccagg tgaaggccct aaggagtagg catatcttgg cttacagttc    4500
agttatgcag ccttttccag ataaagcgtt tctgtctcta gcttcagaca ctgtggaacc    4560
aactatactt aatgccacta acactagcct cacaatcaga ttacctctgg ccaagacaaa    4620
cctcacatgg tatggcatca ccagccctac tccaacatac ctggtttatt atgcagaagt    4680
taatgacagg aaaaacagct ctgacttgaa atatagaatt ctggaatttc aggacagtat    4740
agctcttatt gaagatttac aaccatttc aacatacatg atacagatag ctgtaaaaaa    4800
ttattattca gatcctttgg aacatttacc accaggaaaa gagatttggg gaaaaactaa    4860
aaatggagta ccagaggcag tgcagctcat taatacaact gtgcggtcag acaccagcct    4920
cattatatct tggagagaat ctcacaagcc aaatggacct aaagaatcag tccgttatca    4980
gttggcaatc tcacacctgg ccctaattcc tgaaactcct ctaagacaaa gtgaatttcc    5040
aaatggaagg ctcactctcc ttgttactag actgtctggt ggaaatatt atgtgttaaa    5100
ggttcttgcc tgccactctg aggaaatgtg gtgtacagag agtcatcctg tcactgtgga    5160
aatgtttaac acaccagaga aaccttattc cttggttcca gagaacacta gtttgcaatt    5220
taattggaag gctccattga atgttaacct catcagattt tgggttgagc tacagaagtg    5280
gaaatacaat gagttttacc atgttaaaac ttcatgcagc caaggtcctg cttatgtctg    5340
taatatcaca aatctacaac cttatacttc atataatgtc agagtagtgg tggtttataa    5400
gacgggagaa aatagcacct cacttccaga aagctttaag acaaaagctg gagtcccaaa    5460
```

```
taaaccaggc attcccaaat tactagaagg gagtaaaaat tcaatacagt gggagaaagc    5520
tgaagataat ggatgtagaa ttacatacta tatccttgag ataagaaaga gcacttcaaa    5580
taatttacag aaccagaatt taaggtggaa gatgacattt aatggatcct gcagtagtgt    5640
ttgcacatgg aagtccaaaa acctgaaagg aatatttcag ttcagagtag tagctgcaaa    5700
taatctaggg tttggtgaat atagtggaat cagtgagaat attatattag ttggagatga    5760
tttttggata ccagaaacaa gtttcatact tactattata gttggaatat ttctggttgt    5820
tacaatccca ctgacctttg tctggcatag aagattaaag aatcaaaaaa gtgccaagga    5880
aggggtgaca gtgcttataa acgaagacaa agagttggct gagctgcgag gtctggcagc    5940
cggagtaggc ctggctaatg cctgctatgc aatacatact cttccaaccc aagaggagat    6000
tgaaaatctt cctgccttcc ctcgggaaaa actgactctg cgtctcttgc tgggaagtgg    6060
agcctttgga gaagtgtatg aaggaacagc agtggacatc ttaggagttg aagtggaga    6120 aatcaaagta gcagtgaaga ctttgaagaa gggttccaca gaccaggaga agattgaatt    6180
cctgaaggag gcacatctga tgagcaaatt taatcatccc aacattctga agcagcttgg    6240
agtttgtctg ctgaatgaac cccaatacat tatcctggaa ctgatggagg gaggagacct    6300
tcttacttat ttgcgtaaag cccggatggc aacgttttat ggtcctttac tcaccttggt    6360
tgaccttgta gacctgtgtg tagatatttc aaaaggctgt gtctacttgg aacggatgca    6420
tttcattcac agggatctgg cagctagaaa ttgccttgtt tccgtgaaag actataccag    6480
tccacggata gtgaagattg gagactttgg actcgccaga gacatctata aaaatgatta    6540
ctatagaaag agaggggaag gcctgctccc agttcggtgg atggctccag aaagtttgat    6600
ggatggaatc ttcactactc aatctgatgt atggtctttt ggaattctga tttgggagat    6660
tttaactctt ggtcatcagc cttatccagc tcattccaac cttgatgtgt taaactatgt    6720
gcaaacagga gggagactgg agccaccaag aaattgtcct gatgatctgt ggaatttaat    6780
gacccagtgc tgggctcaag aacccgacca aagacctact tttcatagaa ttcaggacca    6840
acttcagtta ttcagaaatt ttttcttaaa tagcatttat aagtccagag atgaagcaaa    6900
caacagtgga gtcataaatg aaagctttga aggtgaagat ggcgatgtga tttgtttgaa    6960
ttcagatgac attatgccag ttgctttaat ggaaacgaag aaccgagaag ggttaaacta    7020
tatggtactt gctacagaat gtggccaagg tgaagaaaag tctgagggtc tctaggctc    7080 ccaggaatct gaatcttgtg gtctgaggaa agaagagaag gaaccacatg cagacaaaga    7140
tttctgccaa gaaaaacaag tggcttactg cccttctggc aagcctgaag gcctgaacta    7200
tgcctgtctc actcacagtg gatatggaga tgggtctgat taatagcgtt gtttgggaaa    7260
tagagagttg agataaacac tctcattcag tagttactga aagaaaactc tgctagaatg    7320
ataaatgtca tggtggtcta taactccaaa taaacaatgc aacgttcc                 7368
```

<210> SEQ ID NO 2
<211> LENGTH: 6267
<212> TYPE: DNA
<213> ORGANISM: Homo sapiens

<400> SEQUENCE: 2

```
agctgcaagt ggcgggcgcc caggcagatg cgatccagcg gctctggggg cggcagcggt     60
ggtagcagct ggtacctccc gccgcctctg ttcggagggt cgcggggcac cgaggtgctt    120
tccggccgcc ctctggtcgg ccacccaaag ccgcgggcgc tgatgatggg tgaggagggg    180
```

```
gcggcaagat tcgggcgcc cctgccctga acgccctcag ctgctgccgc cggggccgct    240
ccagtgcctg cgaactctga ggagccgagg cgccggtgag agcaaggacg ctgcaaactt    300
gcgcagcgcg ggggctggga ttcacgccca gaagttcagc aggcagacag tccgaagcct    360
tcccgcagcg gagagatagc ttgagggtgc gcaagacggc agcctccgcc ctcggttccc    420
gcccagaccg ggcagaagag cttggaggag ccaaaaggaa cgcaaaaggc ggccaggaca    480
gcgtgcagca gctgggagcc gccgttctca gccttaaaag ttgcagagat tggaggctgc    540
cccgagaggg gacagacccc agctccgact gcggggggca ggagaggacg gtacccaact    600
gccacctccc ttcaaccata gtagttcctc tgtaccgagc gcagcgagct acagacgggg    660
gcgcggcact cggcgcggag agcgggaggc tcaaggtccc agccagtgag cccagtgtgc    720
ttgagtgtct ctggactcgc ccctgagctt ccaggtctgt ttcatttaga ctcctgctcg    780
cctccgtgca gttgggggaa agcaagagac ttgcgcgcac gcacagtcct ctggagatca    840
ggtggaagga gccgctgggt accaaggact gttcagagcc tcttcccatc tcggggagag    900
cgaagggtga ggctgggccc ggagagcagt gtaaacggcc tcctccggcg ggatgggagc    960
catcgggctc ctgtggctcc tgccgctgct gctttccacg gcagctgtgg gctccgggat   1020
ggggaccggc cagcgcgcgg gctcccagc tgcggggccg ccgctgcagc cccggagcc   1080 actcagctac tcgcgcctgc agaggaagag tctggcagtt gacttcgtgg tgccctcgct   1140
cttccgtgtc tacgcccggg acctactgct gccaccatcc tcctcggagc tgaaggctgg   1200
caggcccgag gcccgcggct cgctagctct ggactgcgcc ccgctgctca ggttgctggg   1260
gccggcgccc ggggtctcct ggaccgccgg ttcaccagcc ccggcagagg cccggacgct   1320
gtccagggtg ctgaagggcg gctccgtgcg caagctccgg cgtgccaagc agttggtgct   1380
ggagctgggc gaggaggcga tcttggaggg ttgcgtcggg cccccgggg aggcggctgt   1440 ggggctgctc cagttcaatc tcagcgagct gttcagttgg tggattcgcc aaggcgaagg   1500
gcgactgagg atccgcctga tgcccgagaa gaaggcgtcg gaagtgggca gagagggaag   1560
gctgtccgcg gcaattcgcg cctcccagcc ccgccttctc ttccagatct cgggactgg   1620 tcatagctct ttggaatcac caacaaacat gccttctcct tctcctgatt attttacatg   1680
gaatctcacc tggataatga aagactcctt cccttttcctg tctcatcgca gccgatatgg   1740
tctggagtgc agctttgact tcccctgtga gctggagtat tccccctccac tgcatgacct   1800 caggaaccag agctggtcct ggcgccgcat cccctccgag gaggcctccc agatggactt   1860
gctggatggg cctggggcag agcgttctaa ggagatgccc agaggctcct ttctccttct   1920
caacacctca gctgactcca agcacaccat cctgagtccg tggatgagga gcagcagtga   1980
gcactgcaca ctggccgtct cggtgcacag gcacctgcag ccctctggaa ggtacattgc   2040
ccagctgctg ccccacaacg aggctgcaag agagatcctc ctgatgccca ctccagggaa   2100
gcatggttgg acagtgctcc agggaagaat cgggcgtcca gacaacccat ttcgagtggc   2160
cctggaatac atctccagtg gaaaccgcag cttgtctgca gtggacttct ttgccctgaa   2220
gaactgcagt gaaggaacat ccccaggctc caagatggcc ctgcagagct ccttcacttg   2280
ttggaatggg acagtcctcc agcttgggca ggcctgtgac ttccaccagg actgtgccca   2340
gggagaagat gagagccaga tgtgccggaa actgcctgtg ggtttttact gcaactttga   2400
agatggcttc tgtggctgga cccaaggcac actgtcaccc cacactcctc aatggcaggt   2460
caggacccta aaggatgccc ggttccagga ccaccaagac catgctctat tgctcagtac   2520
cactgatgtc cccgcttctg aaagtgctac agtgaccagt gctacgtttc ctgcaccgat   2580
```

```
caagagctct ccatgtgagc tccgaatgtc ctggctcatt cgtggagtct tgagggaaaa    2640
cgtgtccttg gtgctagtgg agaacaaaac cgggaaggag caaggcagga tggtctggca    2700
tgtcgccgcc tatgaaggct tgagcctgtg gcagtggatg gtgttgcctc tcctcgatgt    2760
gtctgacagg ttctggctgc agatggtcgc atggtgggga caaggatcca gagccatcgt    2820
ggcttttgac aatatctcca tcagcctgga ctgctacctc accattagcg agaggacaa     2880 gatcctgcag aatacagcac ccaaatcaag aaacctgttt gagagaaacc caaacaagga    2940
gctgaaaccc ggggaaaatt caccaagaca daccccccatc tttgacccta cagttcattg   3000
gctgttcacc acatgtgggg ccagcgggcc ccatggcccc acccaggcac agtgcaacaa    3060
cgcctaccag aactccaacc tgagcgtgga ggtggggagc gagggccccc tgaaaggcat    3120
ccagatctgg aaggtgccag ccaccgacac ctacagcatc tcgggctacg agctgctgg     3180 cgggaaaggc gggaagaaca ccatgatgcg gtcccacggc gtgtctgtgc tgggcatctt    3240
caacctggag aaggatgaca tgctgtacat cctggttggg cagcagggag aggacgcctg    3300
ccccagtaca aaccagttaa tccagaaagt ctgcattgga gagaacaatg tgatagaaga    3360
agaaatccgt gtgaacagaa gcgtgcatga gtgggcagga ggcggaggag gaggggtgg     3420 agccacctac gtatttaaga tgaaggatgg agtgccggtg cccctgatca ttgcagccgg    3480
aggtggtggc agggcctacg gggccaagac agacacgttc cacccagaga gactggagaa    3540
taactcctcg gttctagggc taaacggcaa ttccggagcc gcaggtggtg gaggtggctg    3600
gaatgataac acttccttgc tctgggccgg aaaatctttg caggagggtg ccaccggagg    3660
acattcctgc ccccaggcca tgaagaagtg ggggtgggag acaagagggg gtttcggagg    3720
gggtggaggg gggtgctcct caggtggagg aggcggagga tatataggcg gcaatgcagc    3780
ctcaaacaat gaccccgaaa tggatgggga agatggggtt tccttcatca gtccactggg    3840
catcctgtac accccagctt taaaagtgat ggaaggccac ggggaagtga atattaagca    3900
ttatctaaac tgcagtcact gtgaggtaga cgaatgtcac atggaccctg aaagccacaa    3960
ggtcatctgc ttctgtgacc acgggacggt gctggctgag gatggcgtct cctgcattgt    4020
gtcacccacc ccggagccac acctgccact ctcgctgatc ctctctgtgg tgacctctgc    4080
cctcgtggcc gccctggtcc tggctttctc cggcatcatg attgtgtacc gccggaagca    4140
ccaggagctg caagccatgc agatggagct gcagagccct gagtacaagc tgagcaagct    4200
ccgcacctcg accatcatga ccgactacaa ccccaactac tgctttgctg caagacctc    4260 ctccatcagt gacctgaagg aggtgccgcg gaaaaacatc accctcattc ggggtctggg    4320
ccatggcgcc tttggggagg tgtatgaagg ccaggtgtcc ggaatgccca acgacccaag    4380
ccccctgcaa gtggctgtga agacgctgcc tgaagtgtgc tctgaacagg acgaactgga    4440
tttcctcatg gaagccctga tcatcagcaa attcaaccac cagaacattg ttcgctgcat    4500 tgggggtgagc ctgcaatccc tgccccggtt catcctgctg gagctcatgg cgggggagag  4560
cctcaagtcc ttcctccgag agacccgccc tcgcccgagc cagccctcct ccctggccat    4620
gctggacctt ctgcacgtgg ctcgggacat tgcctgtggc tgtcagtatt tggaggaaaa    4680
ccacttcatc caccgagaca ttgctgccag aaactgcctc ttgacctgtc caggccctgg    4740
aagagtggcc aagattggag acttcgggat ggcccgagac atctacaggg cgagctacta    4800
tagaaaggga ggctgtgcca tgctgccagt taagtggatg ccccagagg ccttcatgga     4860 aggaatattc acttctaaaa cagacacatg gtcctttgga gtgctgctat gggaaatctt    4920
```

```
ttctcttgga tatatgccat accccagcaa aagcaaccag gaagttctgg agtttgtcac   4980
cagtggaggc cggatggacc cacccaagaa ctgccctggg cctgtatacc ggataatgac   5040
tcagtgctgg caacatcagc ctgaagacag gcccaacttt gccatcattt tggagaggat   5100
tgaatactgc acccaggacc cggatgtaat caacaccgct ttgccgatag aatatggtcc   5160
acttgtggaa gaggaagaga agtgcctgt gaggcccaag gaccctgagg gggttcctcc   5220
tctcctggtc tctcaacagg caaaacggga ggaggagcgc agcccagctg ccccaccacc   5280
tctgcctacc acctcctctg gcaaggctgc aaagaaaccc acagctgcag agatctctgt   5340
tcgagtccct agagggccgg ccgtggaagg gggacacgtg aatatggcat tctctcagtc   5400
caaccctcct tcggagttgc acaaggtcca cggatccaga aacaagccca ccagcttgtg   5460
gaacccaacg tacggctcct ggtttacaga gaaacccacc aaaaagaata atcctatagc   5520
aaagaaggag ccacacgaca ggggtaacct ggggctggag ggaagctgta ctgtcccacc   5580
taacgttgca actgggagac ttccgggggc ctcactgctc ctagagccct cttcgctgac   5640
tgccaatatg aaggaggtac tctgttcag gctacgtcac ttcccttgtg ggaatgtcaa   5700
ttacggctac cagcaacagg gcttgcccct agaagccgct actgccctg gagctggtca   5760 ttacgaggat accattctga aaagcaagaa tagcatgaac cagcctgggc cctgagctcg   5820
gtcgcacact cacttctctt ccttgggatc cctaagaccg tggaggagag agaggcaatg   5880
gctccttcac aaaccagaga ccaaatgtca cgttttgttt tgtgccaacc tattttgaag   5940
taccaccaaa aaagctgtat tttgaaaatg ctttagaaag gttttgagca tgggttcatc   6000
ctattctttc gaaagaagaa aatatcataa aaatgagtga taaatacaag gcccagatgt   6060
ggttgcataa ggttttatg catgtttgtt gtatacttcc ttatgcttct ttcaaattgt   6120
gtgtgctctg cttcaatgta gtcagaatta gctgcttcta tgtttcatag ttggggtcat   6180
agatgtttcc ttgccttgtt gatgtggaca tgagccattt gaggggagag ggaacggaaa   6240
taaaggagtt atttgtaatg actaaaa                                       6267

<210> SEQ ID NO 3
<211> LENGTH: 4174
<212> TYPE: DNA
<213> ORGANISM: Homo sapiens

<400> SEQUENCE: 3
agtcccgcga ccgaagcagg gcgcgcagca gcgctgagtg ccccggaacg tgcgtcgcgc     60
ccccagtgtc cgtcgcgtcc gccgcgcccc gggcggggat ggggcggcca gactgagcgc    120
cgcacccgcc atccagaccc gccggcccta gccgcagtcc ctccagccgt ggccccagcg    180
cgcacgggcg atggcgaagg cgacgtccgg tgccgcgggg ctgcgtctgc tgttgctgct    240
gctgctgccg ctgctaggca agtggcatt gggcctctac ttctcgaggg atgcttactg    300
ggagaagctg tatgtggacc aggcggccgg cacgcccttg ctgtacgtcc atgcctgcg    360 ggacgcccct gaggaggtgc ccagcttccg cctgggccag catctctacg cacgtaccg    420 cacacggctg catgagaaca actggatctg catccaggag gacaccggcc tcctctacct    480
taaccggagc ctggaccata gctcctggga gaagctcagt gtccgcaacc gcggctttcc    540
cctgctcacc gtctacctca aggtcttcct gtcacccaca tcccttcgtg agggcgagtg    600
ccagtggcca ggctgtgccc gcgtatactc ctccttcttc aacacctcct ttccagcctg    660
cagctcccct aagccccggg agctctgctt cccagagaca aggcccctcct tccgcattcg    720 ggagaaccga ccccaggca ccttccacca gttccgcctg ctgcctgtgc agttcttgtg    780
```

```
ccccaacatc agcgtggcct acaggctcct ggagggtgag ggtctgccct tccgctgcgc    840
cccggacagc ctggaggtga gcacgcgctg ggccctggac cgcgagcagc gggagaagta    900
cgagctggtg gccgtgtgca ccgtgcacgc cggcgcgcgc gaggaggtgg tgatggtgcc    960
cttcccggtg accgtgtacg acgaggacga ctcggcgccc accttccccg cgggcgtcga   1020
caccgccagc gccgtggtgg agttcaagcg gaaggaggac accgtggtgg ccacgctgcg   1080
tgtcttcgat gcagacgtgg tacctgcatc aggggagctg gtgaggcggt acacaagcac   1140
gctgctcccc ggggacacct gggcccagca gaccttccgg gtggaacact ggcccaacga   1200
gacctcggtc caggccaacg gcagcttcgt gcgggcgacc gtacatgact ataggctggt   1260
tctcaaccgg aacctctcca tctcggagaa ccgcaccatg cagctggcgg tgctggtcaa   1320
tgactcagac ttccagggcc caggagcggg cgtcctcttg ctccacttca acgtgtcggt   1380
gctgccggtc agcctgcacc tgcccagtac ctactccctc tccgtgagca ggagggctcg   1440
ccgatttgcc cagatcggga aagtctgtgt ggaaaactgc caggcattca gtggcatcaa   1500
cgtccagtac aagctgcatt cctctggtgc caactgcagc acgctagggg tggtcacctc   1560
agccgaggac acctcgggga tcctgtttgt gaatgacacc aaggccctgc ggcggcccaa   1620
gtgtgccgaa cttcactaca tggtggtggc caccgaccag cagacctcta ggcaggccca   1680
ggcccagctg cttgtaacag tggaggggtc atatgtggcc gaggaggcgg gctgccccct   1740
gtcctgtgca gtcagcaaga cggctgga gtgtgaggag tgtggcggcc tgggctcccc   1800
aacaggcagg tgtgagtgga ggcaaggaga tggcaaaggg atcaccagga acttctccac   1860
ctgctctccc agcaccaaga cctgccccga cggccactgc gatgttgtgg agacccaaga   1920
catcaacatt tgccctcagg actgcctccg gggcagcatt gttggggac acgagcctgg   1980 ggagccccgg gggattaaag ctggctatgg cacctgcaac tgcttccctg aggaggagaa   2040
gtgcttctgc gagcccgaag acatccagga tccactgtgc gacgagctgt gccgcacggt   2100
gatcgcagcc gctgtcctct tctccttcat cgtctcggtg ctgctgtctg ccttctgcat   2160
ccactgctac cacaagtttg cccacaagcc acccatctcc tcagctgaga tgaccttccg   2220
gaggcccgcc caggccttcc cggtcagcta ctcctcttcc ggtgcccgcc ggccctcgct   2280
ggactccatg gagaaccagg tctccgtgga tgccttcaag atcctggagg atcccaaagtg   2340 ggaattccct cggaagaact tggttcttgg aaaaactcta ggagaaggcg aatttggaaa   2400
agtggtcaag gcaacggcct tccatctgaa aggcagagca gggtacacca cggtggccgt   2460
gaagatgctg aaagagaacg cctccccgag tgagcttcga gacctgctgt cagagttcaa   2520
cgtcctgaag caggtcaacc acccacatgt catcaaattg tatgggcct gcagccagga   2580 tggcccgctc ctcctcatcg tggagtacgc caaatacggc tccctgcggg gcttcctccg   2640
cgagagccgc aaagtggggc ctggctacct gggcagtgga ggcagccgca actccagctc   2700
cctggaccac ccggatgagc gggccctcac catgggcgac ctcatctcat ttgcctggca   2760
gatctcacag gggatgcagt atctggccga gatgaagctc gttcatcggg acttggcagc   2820
cagaaacatc ctggtagctg aggggcggaa gatgaagatt tcggatttcg gcttgtcccg   2880
agatgtttat gaagaggatt cctacgtgaa gaggagccag ggtcggattc cagttaaatg   2940
gatggcaatt gaatcccttt ttgatcatat ctacaccacg caaagtgatg tatggtcttt   3000
tggtgtcctg ctgtgggaga tcgtgaccct agggggaaac ccctatcctg ggattcctcc   3060
tgagcggctc ttcaaccttc tgaagaccgg ccaccggatg gagaggccag acaactgcag   3120
```

| | |
|---|---:|
| cgaggagatg taccgcctga tgctgcaatg ctggaagcag gagccggaca aaaggccggt | 3180 |
| gtttgcggac atcagcaaag acctggagaa gatgatggtt aagaggagag actacttgga | 3240 |
| ccttgcggcg tccactccat ctgactccct gatttatgac gacggcctct cagaggagga | 3300 |
| gacaccgctg gtggactgta ataatgcccc cctccctcga gccctcccct tccacatggat | 3360 |
| tgaaaacaaa ctctatggta gaatttccca tgcatttact agattctagc accgctgtcc | 3420 |
| cctctgcact atccttcctc tctgtgatgc ttttttaaaaa tgtttctggt ctgaacaaaa | 3480 |
| ccaaagtctg ctctgaacct ttttatttgt aaatgtctga ctttgcatcc agtttacatt | 3540 |
| taggcattat tgcaactatg ttttttctaaa aggaagtgaa aataagtgta attaccacat | 3600 |
| tgcccagcaa cttaggatgg tagaggaaaa aacagatcag ggcggaactc tcaggggaga | 3660 |
| ccaagaacag gttgaataag gcgcttctgg ggtgggaatc aagtcatagt acttctactt | 3720 |
| taactaagtg gataaatata caaatctggg gaggtattca gttgagaaag gagccaccag | 3780 |
| caccactcag cctgcactgg gagcacagcc aggttccccc agaccctcc tgggcaggca | 3840 |
| ggtgcctctc agaggccacc cggcactggc gagcagccac tggccaagcc tcagcccag | 3900 |
| tcccagccac atgtcctcca tcaggggtag cgaggttgca ggagctggct ggccctggga | 3960 |
| ggacgcaccc ccactgctgt tttcacatcc tttcccttac ccaccttcag gacggttgtc | 4020 |
| acttatgaag tcagtgctaa agctggagca gttgcttttt gaaagaacat ggtctgtggt | 4080 |
| gctgtggtct tacaatggac agtaaatatg gttcttgcca aaactccttc ttttgtcttt | 4140 |
| gattaaatac tagaaattta aaaaaaaaaa aaaa | 4174 |

<210> SEQ ID NO 4
<211> LENGTH: 5629
<212> TYPE: DNA
<213> ORGANISM: Homo sapiens

<400> SEQUENCE: 4

| | |
|---|---:|
| agtcccgcga ccgaagcagg gcgcgcagca gcgctgagtg ccccggaacg tgcgtcgcgc | 60 |
| ccccagtgtc cgtcgcgtcc gccgcgcccc gggcggggat ggggcggcca gactgagcgc | 120 |
| cgcacccgcc atccagaccc gccggcccta gccgcagtcc ctccagccgt ggccccagcg | 180 |
| cgcacgggcg atggcgaagg cgacgtccgg tgccgcgggg ctgcgtctgc tgttgctgct | 240 |
| gctgctgccg ctgctaggca aagtggcatt gggcctctac ttctcgaggg atgcttactg | 300 |
| ggagaagctg tatgtggacc aggcggccgg cacgcccttg ctgtacgtcc atgccctgcg | 360 |
| ggacgcccct gaggaggtgc ccagcttccg cctgggccag catctctacg gcacgtaccg | 420 |
| cacgcggctg catgagaaca actggatctg catccaggag gacaccggcc tcctctacct | 480 |
| taaccggagc ctggaccata gctcctggga gaagctcagt gtccgcaacc gcggctttcc | 540 |
| cctgctcacc gtctacctca aggtcttcct gtcacccaca tcccttcgtg agggcgagtg | 600 |
| ccagtggcca ggctgtgccc gcgtatactt ctccttcttc aacacctcct ttccagcctg | 660 |
| cagctcccctc aagccccggg agctctgctt cccagagaca aggcccctcct tccgcattcg | 720 |
| ggagaaccga ccccccaggca ccttccacca gttccgcctg ctgcctgtgc agttcttgtg | 780 |
| ccccaacatc agcgtggcct acaggctcct ggagggtgag ggtctgccct tccgctgcgc | 840 |
| cccggacagc ctggaggtga gcacgcgctg ggccctggac cgcgagcagc gggagaagta | 900 |
| cgagctggtg gccgtgtgca ccgtgcacgc cggcgcgcgc gaggaggtgg tgatggtgcc | 960 |
| cttccccggtg accgtgtacg acgaggacga ctcggcgccc accttccccg cgggcgtcga | 1020 |
| caccgccagc gccgtggtgg agttcaagcg gaaggaggac accgtggtgg ccacgctgcg | 1080 |

```
tgtcttcgat gcagacgtgg tacctgcatc aggggagctg gtgaggcggt acacaagcac   1140
gctgctcccc ggggacacct gggcccagca gaccttccgg gtggaacact ggcccaacga   1200
gacctcggtc caggccaacg gcagcttcgt gcgggcgacc gtacatgact ataggctggt   1260
tctcaaccgg aacctctcca tctcggagaa ccgcaccatg cagctggcgg tgctggtcaa   1320
tgactcagac ttccagggcc caggagcggg cgtcctcttg ctccacttca acgtgtcggt   1380
gctgccggtc agcctgcacc tgcccagtac ctactccctc tccgtgagca ggagggctcg   1440
ccgatttgcc cagatcggga aagtctgtgt ggaaaactgc caggcattca gtggcatcaa   1500
cgtccagtac aagctgcatt cctctggtgc caactgcagc acgctagggg tggtcacctc   1560
agccgaggac acctcgggga tcctgtttgt gaatgacacc aaggccctgc ggcggcccaa   1620
gtgtgccgaa cttcactaca tggtggtggc caccgaccag cagacctcta ggcaggccca   1680
ggcccagctg cttgtaacag tggaggggtc atatgtggcc gaggaggcgg gctgccccct   1740
gtcctgtgca gtcagcaaga gacggctgga gtgtgaggag tgtggcggcc tgggctcccc   1800
aacaggcagg tgtgagtgga ggcaaggaga tggcaaaggg atcaccagga acttctccac   1860
ctgctctccc agcaccaaga cctgcccccga cggccactgc gatgttgtgg agacccaaga   1920
catcaacatt tgccctcagg actgcctccg gggcagcatt gttggggac acgagcctgg   1980 ggagccccgg gggattaaag ctggctatgg cacctgcaac tgcttccctg aggaggagaa   2040
gtgcttctgc gagcccgaag acatccagga tccactgtgc gacgagctgt gccgcacggt   2100
gatcgcagcc gctgtcctct tctccttcat cgtctcggtg ctgctgtctg ccttctgcat   2160
ccactgctac cacaagtttg cccacaagcc acccatctcc tcagctgaga tgaccttccg   2220
gaggcccgcc caggccttcc cggtcagcta ctcctcttcc ggtgcccgcc ggccctcgct   2280
ggactccatg gagaaccagg tctccgtgga tgccttcaag atcctggagg atccaaagtg   2340
ggaattccct cggaagaact tggttcttgg aaaaactcta ggagaaggcg aatttggaaa   2400
agtggtcaag gcaacggcct tccatctgaa aggcagagca gggtacacca cggtggccgt   2460
gaagatgctg aaagagaacg cctcccccgag tgagcttcga cctgctgtg cagagttcaa   2520 cgtcctgaag caggtcaacc acccacatgt catcaaattg tatgggcct gcagccagga   2580 tggcccgctc ctcctcatcg tggagtacgc caaatacggc tccctgcggg gcttcctccg   2640
cgagagccgc aaagtggggc ctggctacct gggcagtgga ggcagccgca actccagctc   2700
cctggaccac ccggatgagc gggccctcac catgggcgac ctcatctcat ttgcctggca   2760
gatctcacag gggatgcagt atctggccga gatgaagctc gttcatcggg acttggcagc   2820
cagaaacatc ctggtagctg aggggcggaa gatgaagatt tcggatttcg gcttgtcccg   2880
agatgtttat gaagaggatt cctacgtgaa gaggagccag ggtcggattc cagttaaatg   2940
gatggcaatt gaatcccttt ttgatcatat ctacaccacg caaagtgatg tatggtcttt   3000
tggtgtcctg ctgtgggaga tcgtgaccct aggggaaac ccctatcctg ggattcctcc   3060
tgagcggctc ttcaaccttc tgaagaccgg ccaccggatg gagaggccag acaactgcag   3120
cgaggagatg taccgcctga tgctgcaatg ctggaagcag gagccggaca aaaggccggt   3180
gtttgcggac atcagcaaag acctggagaa gatgatggtt aagaggagag actacttgga   3240
ccttgcggcg tccactccat ctgactccct gatttatgac acggcctct cagaggagga   3300 gacaccgctg gtggactgta ataatgcccc cctcccctcga gccctcccttt ccacatggat   3360 tgaaaacaaa ctctatggca tgtcagaccc gaactggcct ggagagagtc ctgtaccact   3420
```

```
cacgagagct gatggcacta acactgggtt ccaagatat ccaaatgata gtgtatatgc   3480
taactggatg cttctcaccct cagcggcaaa attaatggac acgtttgata gttaacattt   3540
ctttgtgaaa ggtaatggac tcacaagggg aagaaacatg ctgagaatgg aaagtctacc   3600
ggccctttct tgtgaacgt cacattggcc gagccgtgtt cagttccag gtggcagact   3660 cgttttggt agtttgtttt aacttccaag gtggttttac ttctgatagc cggtgatttt   3720
ccctcctagc agacatgcca caccgggtaa gagctctgag tcttagtggt taagcattcc   3780
tttctcttca gtgcccagca gcacccagtg ttggtctgtg tccatcagtg accaccaaca   3840
ttctgtgttc acatgtgtgg gtccaacact tactacctgg tgtatgaaat tggacctgaa   3900
ctgttggatt tttctagttg ccgccaaaca aggcaaaaaa atttaaacat gaagcacaca   3960
cacaaaaaag gcagtaggaa aaatgctggc cctgatgacc tgtccttatt cagaatgaga   4020
gactgcgggg ggggcctggg ggtagtgtca atgcccctcc agggctggag gggaagaggg   4080
gccccgagga tgggcctggg ctcagcattc gagatcttga gaatgatttt tttttaatca   4140
tgcaaccttt ccttaggaag acatttggtt ttcatcatga ttaagatgat tcctagattt   4200
agcacaatgg agagattcca tgccatcttt actatgtgga tggtggtatc agggaagagg   4260
gctcacaaga cacatttgtc ccccgggccc accacatcat cctcacgtgt tcggtactga   4320
gcagccacta cccctgatga gaacagtatg aagaagggg gctgttggag tcccagaatt   4380
gctgacagca gaggctttgc tgctgtgaat cccacctgcc accagcctgc agcacacccc   4440
acagccaagt agaggcgaaa gcagtggctc atcctacctg ttaggagcag gtagggcttg   4500
tactcacttt aatttgaatc ttatcaactt actcataaag ggacaggcta gctagctgtg   4560
ttagaagtag caatgacaat gaccaaggac tgctacacct ctgattacaa ttctgatgtg   4620
aaaaagatgg tgtttggctc ttatagagcc tgtgtgaaag gcccatggat cagctcttcc   4680
tgtgtttgta atttaatgct gctacaagat gtttctgttt cttagattct gaccatgact   4740
cataagcttc ttgtcattct tcattgcttg tttgtggtca cagatgcaca acactcctcc   4800
agtcttgtgg gggcagcttt tgggaagtct cagcagctct tctggctgtg ttgtcagcac   4860
tgtaacttcg cagaaaagag tcggattacc aaaacactgc ctgctcttca gacttaaagc   4920
actgatagga cttaaaatag tctcattcaa atactgtatt ttatataggc atttcacaaa   4980
aacagcaaaa ttgtggcatt ttgtgaggcc aaggcttgga tgcgtgtgta atagagcctt   5040
gtggtgtgtg cgcacacacc cagagggaga gtttgaaaaa tgcttattgg acacgtaacc   5100
tggctctaat ttgggctgtt tttcagatac actgtgataa gttcttttac aaatatctat   5160
agacatggta aacttttggt tttcagatat gcttaatgat agtcttacta aatgcagaaa   5220
taagaataaa cttctcaaa ttattaaaaa tgcctacaca gtaagtgtga attgctgcaa   5280
caggtttgtt ctcaggaggg taagaactcc aggtctaaac agctgaccca gtgatgggga   5340 attatcctt gaccaattta tccttgacca ataacctaat tgtctattcc tgagttataa   5400
aagtccccat ccttattagc tctactggaa ttttcataca cgtaaatgca gaagttacta   5460
agtattaagt attactgagt attaagtagt aatctgtcag ttattaaaat ttgtaaaatc   5520
tatttatgaa aggtcattaa accagatcat gttccttttt ttgtaatcaa ggtgactaag   5580
aaaatcagtt gtgtaaataa aatcatgtat cataaaaaaa aaaaaaaa              5629
```

<210> SEQ ID NO 5
<211> LENGTH: 10
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 5
tttttttttt                                                                10
```